US011104885B2

(12) United States Patent
Vandenberghe et al.

(10) Patent No.: US 11,104,885 B2
(45) Date of Patent: Aug. 31, 2021

(54) METHODS OF PREDICTING ANCESTRAL VIRUS SEQUENCES AND USES THEREOF

(71) Applicants: Massachusetts Eye & Ear Infirmary, Boston, MA (US); The Schepens Eye Research Institute, Inc., Boston, MA (US)

(72) Inventors: Luk H. Vandenberghe, Weston, MA (US); Eric Zinn, Lynn, MA (US)

(73) Assignees: The Schepens Eye Research Institute, Inc., Boston, MA (US); Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 16/717,942

(22) Filed: Dec. 17, 2019

(65) Prior Publication Data

US 2020/0123504 A1 Apr. 23, 2020

Related U.S. Application Data

(60) Division of application No. 16/179,524, filed on Nov. 2, 2018, now Pat. No. 10,526,584, which is a division (Continued)

(51) Int. Cl.
*C12N 7/00* (2006.01)
*C12N 1/00* (2006.01)
(Continued)

(52) U.S. Cl.
CPC ................ *C12N 7/00* (2013.01); *A61K 39/00* (2013.01); *C07K 14/00* (2013.01); *C07K 14/005* (2013.01); *C07K 16/22* (2013.01); *C12N 15/86* (2013.01); *A61K 2039/525* (2013.01); *A61K 2039/6075* (2013.01); *C07K 2317/24* (2013.01); *C07K 2317/76* (2013.01); *C12N 2750/14121* (2013.01); *C12N 2750/14122* (2013.01);

(Continued)

(58) Field of Classification Search
None
See application file for complete search history.

(56) References Cited

U.S. PATENT DOCUMENTS 5,037,384 A 8/1991 Chang
5,817,075 A 10/1998 Giungo (Continued)

FOREIGN PATENT DOCUMENTS

CA 2193802 1/1996
JP 2007-500518 1/2007

(Continued)

OTHER PUBLICATIONS

AU Office Action in Australian Appln. No. 2019201986, dated Mar. 13, 2020, 7 pages.

(Continued)

*Primary Examiner* — M Franco G Salvoza
(74) *Attorney, Agent, or Firm* — Fish & Richardson P.C.

(57) ABSTRACT

Methods are described for predicting ancestral sequences for viruses or portions thereof. Also described are predicted ancestral sequences for adeno-associated virus (AAV) capsid polypeptides. The disclosure also provides methods of gene transfer and methods of vaccinating subjects by administering a target antigen operably linked to the AAV capsid polypeptides.

9 Claims, 23 Drawing Sheets

Specification includes a Sequence Listing.

Related U.S. Application Data of application No. 15/633,292, filed on Jun. 26, 2017, now Pat. No. 10,119,125, which is a division of application No. 15/291,470, filed on Oct. 12, 2016, now Pat. No. 9,719,070, which is a division of application No. 15/095,856, filed on Apr. 11, 2016, now Pat. No. 9,695,220, which is a continuation-in-part of application No. PCT/US2014/060163, filed on Oct. 10, 2014.

(60) Provisional application No. 61/889,827, filed on Oct. 11, 2013.

(51) Int. Cl.
*C07K 14/00* (2006.01)
*C12N 15/86* (2006.01)
*A61K 39/00* (2006.01)
*C07K 14/005* (2006.01)
*C07K 16/22* (2006.01)

(52) U.S. Cl.
CPC .............. *C12N 2750/14123* (2013.01); *C12N 2750/14141* (2013.01); *C12N 2750/14142* (2013.01); *C12N 2750/14143* (2013.01); *C12N 2750/14171* (2013.01)

(56) References Cited

U.S. PATENT DOCUMENTS

| | | | |
|---|---|---|---|
| 7,906,111 | B2 | 3/2011 | Wilson et al. |
| 9,782,232 | B1 | 10/2017 | Papac |
| 2001/0014788 | A1 | 8/2001 | Morris |
| 2004/0216750 | A1 | 11/2004 | Snyder et al. |
| 2007/0028928 | A1 | 2/2007 | Peyman |
| 2007/0225727 | A1 | 9/2007 | Matsuhisa |
| 2008/0090914 | A1 | 4/2008 | Enaida et al. |
| 2009/0226531 | A1 | 9/2009 | Lyons |
| 2011/0098536 | A1 | 4/2011 | Corcosteugi |
| 2012/0093772 | A1 | 4/2012 | Horsager et al. |
| 2014/0248231 | A1 | 9/2014 | Askari |
| 2015/0182756 | A1 | 7/2015 | Peyman |
| 2015/0283265 | A1 | 10/2015 | Peyman |
| 2015/0374543 | A1 | 12/2015 | Shapiro |
| 2016/0296221 | A1 | 10/2016 | Morris |
| 2019/0254870 | A1 | 8/2019 | Hopkins |

FOREIGN PATENT DOCUMENTS

| | | |
|---|---|---|
| WO | WO 2005/033321 | 4/2005 |
| WO | WO 2006/110689 | 10/2006 |
| WO | WO 2014/160092 | 10/2014 |
| WO | WO 2015/054653 | 4/2015 |

OTHER PUBLICATIONS

CA Office Action in Canadian Application No. 2,927,077, dated Jul. 2, 2020, 3 pages.
IN Office Actoin in Indian Appln. No. 201637014659, dated May 28, 2020, 8 pages.
JP Office Action in Japanese Application No. 2018-504699 dated Jun. 9, 2020, 6 pages (with English translation).
Sen et al., "Improved adeno-associated virus (AAV) serotype 1 and 5 vectors for gene therapy", Scientific Reports, May 2013, 3(1):1-6.
Adachi et al., "MOLPHY: Programs for Molecular Phylogenetics based on Maximum Likelihood," Tokyo Institute of Statistical Mathematics, 1996, ed.
Altschul et al., "Gapped BLAST and PSI-BLAST: A new generation of protein database search programs," Nucleic Acids Res., 1997, 25:3389 3402.
American Society of Gene & Cell Therapy 17th Annual Meeting, Molecular Therapy, May 1, 2014, 22(Supplement 1): S1-S305.
Anisimova et al., "Approximate likelihood-ratio test for branches: A fast, accurate, and powerful alternative," Systematic Biology, 2006, 55:539-52.
Balazs et al., "Antibody-based protection against HIV infection by vectored immunoprophylaxis," Nature, 2012, 481:81-4.
Balazs et al., "Broad protection against influenza infection by vectored immunoprophylaxis in mice," Nat. Biotechnol., 2013, 31:647-52.
Bartel et al., "Directed evolution of novel adeno-associated viruses for therapeutic gene delivery," Gene Therapy, Mar. 2012, 19: 694-700.
Boutin et al., 2010, "Prevalence of serum IgG and neutralizing factors against AAV types 1, 2, 5, 6, 8 and 9 in the healthy population: implications for gene therapy using AAV vectors," Hum. Gene Ther., 21:704-12.
Calcedo et al. "Worldwide Epidemiology of Neutralizing Antibodies to Adeno-Associated Viruses," J. Infect. Dis., 2009, 199:381-90.
Cao et al., "Phylogenetic relationships among eutherian orders estimated from inferred sequences of mitochondrial proteins: instability of a tree based on a single gene," J. Mol. Evol., 1994, 39:519-27.
Carvalho et al., "Abstract #: 120: Retinal Tropism of In Silico Reconstructed Ancestral Adeno-Associated Viruses," Molecular Therapy, May 2014, 22(Supplement 1): S45.
Darriba et al., "ProTest3: Fast selection of best-fit models of protein evolution," Bioinformatics, 2011, 27(8):1164-5.
Dayhoff et al., "22 a model of evolutionary change in proteins." Atlas of protein sequence and structure. vol. 5. National Biomedical Research Foundation Silver Spring, 1978. 345-352.
Deal et al., "Vectored antibody gene delivery protects against plasmodium falciparum sporozoite challenge in mice," PNAS USA, 2014, 111:12528-32.
EBI Accession No. GSP:ANJ81137, "Adeno-associated viral capsid protein, AAV -8," Dec. 13, 2007.
Edgar, "MUSCLE: A multipole sequence alignment method with reduced time and space complexity," BMC Bioinform., 2004, 5:113.
EP European Search Report in Application No. 16790158.6, dated Jan. 3, 2019, 5 pages.
EP European Search Report in Application No. 18190809.6, dated Dec. 19, 2018, 5 pages.
EP Extended European Search Report in Application No. 16831443. 3, dated Nov. 26, 2018, 20 pages.
Eyewiki.aao.org [online], "Pars Plana Vitrectomy," Nov. 20, 2019, retrieved on Mar. 27, 2020, retrieved from URL<https://eyewiki.aao.org/Pars_Plana_Vitrectomy>, 7 pages.
Felsenstein, "Maximum Likelihood and Minimum-Steps Methods for Estimating Evolutionary Trees from Data on Discrete Characters," Systematic Biology, 1973, 22:240-9.
Fisher et al., "Recombinant adeno-associated virus for muscle directed gene therapy," 1997, Nature Med., 3:306-12.
Gao et al., "Adeno-associated viruses undergo substantial evolution in primates during natural infections," PNAS, 2003, 100:6081-6.
Gao et al., "Clades of Adeno-associated viruses are widely disseminated in human tissues," J. Virol., 2004, 78:6381-88.
Gao et al., "New recombinant serotypes of AAV vectors," Current Gene Ther., 2005, 5:285-97.
Gascuel, "BioNJ: An improved version of the NJ algorithm based on a simple model of sequence data," Mol. Biol. Evol., 1997, 14:685-95.
GenBank Accession No. AAC03780.1, "major coat protein VP1 [Adeno-associated virus—2]," Feb. 24, 1998, 1 page.
GenBank Accession No. AAD13756.1, "capsid protein [Adeno-associated virus—5]," Feb. 10, 1999, 1 page.
GenBank Accession No. AAD27757.1, "capsid protein [Adeno-associated virus—1]," Apr. 27, 1999, 1 page.
GenBank Accession No. AAN03857.1, "capsid protein [Adeno-associated virus—8]," Sep. 2, 2002, 1 page.
GenBank Accession No. AAO88201.1, "capsid protein [Non-human primate Adeno-associated virus]," Apr. 9, 2003, 1 page.
GenBank Accession No. AAS99264.1, "capsid protein VP1 [Adeno-associated virus 9]," May 25, 2004, 1 page.

(56) References Cited

OTHER PUBLICATIONS

GenBank Accession No. EU368910.1, "Adeno-associated virus isolate AAV6.2 capsid protein VP1 gene, partial cds," Jul. 31, 2008, 1 page.

GenBank Accession No. EU368926, "Adeno-associated virus isolate rh32.33 capsid protein VP1 gene, partial cds," Jul. 31, 2008, 1 page.

Guindon et al., "A simple, fast, and accurate algorithm to estimate large phylogenies by maximum likelihood," Systematic Biology, 2003, 52:696-704.

Henikoff at al., "Amino acid substitution matrices from protein blocks," PNAS, 1992, 89:10915-9.

Jones et al., "The rapid generation of mutation data matrices from protein sequences," 1992, Comp. Appl. Biosci., 8:275-82.

Katoh et al., "MAFFT version 5: Improvement in accuracy of multiple sequence alignment," Nuc. Acids Res., 2005, 33:511-8.

Koerber et al., "DNA Shuffling of Adeno-associated Virus Yields Functionally Diverse Viral Progeny," Molecular Therapy, Aug. 2008, 16: 1703-1709.

Lassmann et al., "Kalign, Kalignvu and Mumsa: Web servers for multiple sequence alignment," Nuc. Acids Res., 2006, 34:W596-99.

Limberis et al., "Intranasal antibody gene transfer in mice and ferrets elicits broad protection against pandemic influenza," Sci. Transl. Med., 2013, 5:187ra72.

Lock et al., "Rapid, simple, and versatile manufacturing of recombinant adeno-associated viral vectors at scale," Hum. Gene Ther., 2010, 21:1259-71.

Loytynoja et al., "An Algorithm for progressive multiple alignment of sequences with insertions," PNAS USA, 2005, 102:10557-62.

Loytynoja et al., "Phylogeny-Aware Gap Placement Prevents Errors in Sequence Alignment and Evolutionary Analysis," Science, 2008, 320:1632-5.

Maheshri et al., "Directed evolution of adeno-associated virus yields enhanced gene delivery vectors," Nature Biotechnology, Jan. 2006, 24: 198-204.

Manning et al., "Transient immunosuppression allows transgene expression following readministration of adeno-associated viral vectors," 1998, Human Gene Ther., 9:477-85.

Mao et al., "Persistent Suppression of Ocular Neovascularization with intravitreal administration of AAVrh.10 coding for Bevacizumab," Hum. Gene Ther., 2011, 22:1525-35.

Nakai et al., "A limited Number of transducible hepatocytes restricts a wide-range linear vector dose response in recombinant adeno-associated virus-mediated liver transduction," J. Virol., 2002, 76:11343-9.

Nakai et al., "Unrestricted hepatocyte transduction with adeno-associated virus serotype 8 vectors in mice," J. Virol., 2005, 79:214-24.

Ncbi.nlm.nih.gov [online], "Facts and Figures Concerning the Human Retina," Jul. 5, 2007, retrieved on Mar. 28, 2020, retrieved from URL<https://www.ncbi.nlm.nih.gov/books/NBK11556/>, 6 pages.

Paul et al., "Determination of hepatitis E virus seroprevalence by using recombinant fusion proteins and synthetic peptides," 1994, J. Infect. Dis., 169:801-6.

PCT International Preliminary Report on Patentability in International Application No. PCT/US2016/031218, dated Nov. 16, 2017, 7 pages.

PCT International Preliminary Report on Patentability in International Application No. PCT/US2016/044819, dated Feb. 8, 2018, 5 pages.

PCT International Search Report and Written Opinion in International Application No. PCT/US2014/060163, dated Jul. 13, 2015, 19 pages.

PCT International Search Report and Written Opinion in International Application No. PCT/US2016/031218, dated Aug. 8, 2016, 12 pages.

PCT International Search Report and Written Opinion in International Application No. PCT/US2016/044819, dated Oct. 31, 2016, 5 pages.

Reeves, "Heterogeneity in the substitution process of amino acid sites of proteins coded for by mitochondrial DNA," 1992, J. Mol. Evol., 35:17-31.

Sakhria et al., "Co-Circulation of Toscana Virus and Punique Virus in Northern Tunisia: A microneutralisation-based seroprevalence study," PLOS Negl. Trop. Dis., 2013, 7:e2429.

Santiago-Ortiz et al., "AAV ancestral reconstruction library enables selection of broadly infectious viral variants," gene Therapy, Jul. 2015, 22: 934-946.

Sarkar et al., Abstract #: 194: "Seroprevalence Assessment of Novel, Ancestrally Derived AAV Vectors," Molecular Therapy, May 2014, 22(Supplement 1): S74.

Sauerbrei et al. "Seroprevalence of herpes simplex virus type 1 and type 2 in Thuringia, Germany, 1999 to 2006," Euro Survell., 2011 ,16(44):3).

Schneider et al., "Empirical codon substitution matrix," BMC Bioinform., 2005, 6:134.

Schon et al., "Retinal gene delivery by adeno-associated virus (AAV) vectors: Strategies and applications," European Journal of Pharmaceutics and Biopharmaceutics, Jan. 2015, 95: 343-352.

Schuster et al., "Biodistribution of adeno-associated virus serotype 9 (AAV9) vector after intrathecal and intravenous delivery in mouse," Frontiers in Neuroanatomy, Jun. 2014, 8: 42 (14 pages).

Schwarz, "Estimating the Dimension of a Model," Ann. Statist. 1978, 6:461-4.

Wang et al., "Systematic Evaluation of AAV Vectors for Liver directed Gene Transfer in Murine Models," Mol. Ther., 2010, 18:118-25.

Watanabe et al., "AAVrh 10-mediated genetic delivery of bevacizumab to the pleura to provide local anti-VEGF to suppress growth of metastatic lung tumors," Gene Ther., 2010, 17:1042-51.

Whelan et al., "A general empirical model of protein evolution derived from multiple protein families using a maximum-likelihood approach," Mol. Biol. Evol., 2001, 18:691-9.

Xie et al., "AAV-mediated persistent bevacizumab therapy suppresses tumor growth of ovarian cancer," Gynecol. Oncol, 2014, 135: 325-32.

Xu et al., "Seroprevalence of herpes simplex virus types 1 and 2 in pregnant women in the United States," Am. J. Obstet. Gynecol., 2007, 196:43.e1-6.

Yang, "Maximum-likelihood estimation of phylogeny from DNA sequences when substitution rates differ over sites," Mol. Biol. Evol., 1993, 10:1396-1401.

Yang, "PAML: A program package for phylogenetic analysis by maximum likelihood," Comp. Applic. BioSci., 1997, 13:555-6.

Zinn and Vandenberghe, "Adeno-associated virus: fit to serve," Current Opinion in virology, Oct. 2014, 8: 90-97.

Zinn et al., "Abstract #: 237: In Silico, Ancestral Reconstruction of AAV Particles Circumvents Pre-Existing Immunity in Humans," Molecular Therapy, May 2014, 22(Supplement 1): S90.

Zinn et al., "In Silico Reconstruction of the Viral Evolutionary Lineage Yields a Potent Gene Therapy Vector," Cell reports, Aug. 2015, 12: 1056-1068.

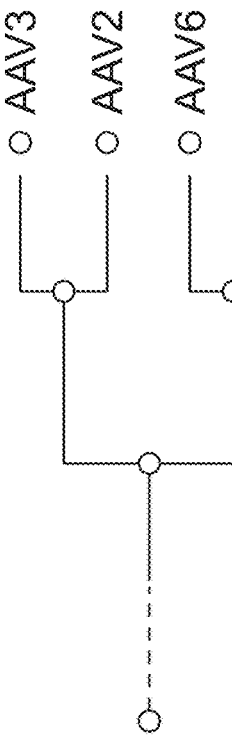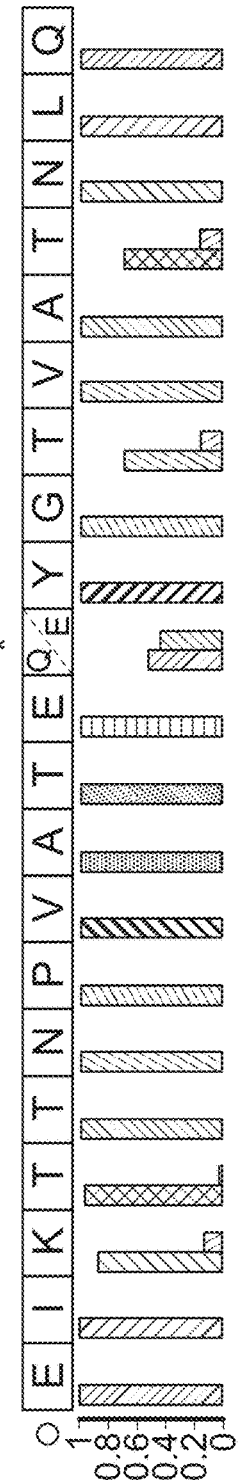

```
                10         20         30         40         50         60         70         80         90        100
         ....|....|....|....|....|....|....|....|....|....|....|....|....|....|....|....|....|....|....|....|
L0065    MAADGVLPDWLEDNLSEGIREWWDLKPGAPKPKANQQKPGAPKPKANQQKQDDGRGLVLPGYKYLGPFNGLDKGEPVNAADAAALEHDKAYDQQLKAGDNPYLRYNHADAEF
L0027    ....................................................................................................
L0033    ....................................................................................................
L0036    ....................................................................................................
L0044    ....................................................................................................
L0059    ....................................................................................................
L0060    ....................................................................................................
L0062    ....................................................................................................

110        120        130        140        150        160        170        180        190        200
         ....|....|....|....|....|....|....|....|....|....|....|....|....|....|....|....|....|....|....|....|
L0065    QERLQEDTSFGGNLGRAVFQAKKRVLEPLGIVEEGAKTAPGKKKRPVEQSPQEPDSSSGIGKKGQQPARKRLNFGQTGDSESVPDPQPLGEPPAAPSGGVGS
L0027    ....................................................................................................
L0033    ..........................................................K.......................................
L0036    ..........................................................K.......................................
L0044    ..........................................................K.......................................
L0059    ..........................................................K.......................................
L0060    ....................................................................................................
L0062    ....................................................................................................

210        220        230        240        250        260        270        280        290        300
         ....|....|....|....|....|....|....|....|....|....|....|....|....|....|....|....|....|....|....|....|
L0065    NTMAAGGAPMADNNEGADGVGNASGNWHCDSTWLGDRVITTSTRTWALPTYNNHLYKQISSQSGGSTNDNTYFGYSTPWGYFDFNRFHCHFSPRDWQRL
L0027    ...S................................................................................................
L0033    ...S................................................................................................
L0036    ...S................................................................................................
L0044    ....................................................................................................
L0059    ...S................................................................................................
L0060    .........................................................................A..........................
L0062    ....................................................................................................

310        320        330        340        350        360        370        380        390        400
         ....|....|....|....|....|....|....|....|....|....|....|....|....|....|....|....|....|....|....|....|
L0065    INNNWGFRPKKLNFKLFNIQVKEVTTNDGITTTIANNLTISTVQVFTDSEYQLPYVLGSAHQGCLPPFPADVFMIPQYGYLTLNNGSQAVGRSSFYCLEYFP
L0027    .........R..........................................................................................
L0033    ....................................................................................................
L0036    ....................................................................................................
L0044    .........R..........................................................................................
L0059    .........R..........................................................................................
L0060    ....................................................................................................
L0062    ....................................................................................................
```

| VP1 seq. Δ | AAV5 | AAV2 | AAV8 | rh10 | Anc80L65 | Anc80Lib |
|---|---|---|---|---|---|---|
| AAV5 | ID | 43.0% | 42.6% | 43.0% | 40.5% | 39.9-40.5% |
| AAV2 | 320 | ID | 17.1% | 15.9% | 12.2% | 12.0-12.8% |
| AAV8 | 317 | 127 | ID | 6.5% | 9.1% | 8.7-10.1% |
| rh10 | 320 | 118 | 48 | ID | 8.6% | 7.8-8.9% |
| L0065 | 301 | 91 | 68 | 64 | 0-11 | 0-1.5% |
| Anc80Lib | 297-302 | 89-95 | 65-75 | 58-66 | | ID |

FIG. 8

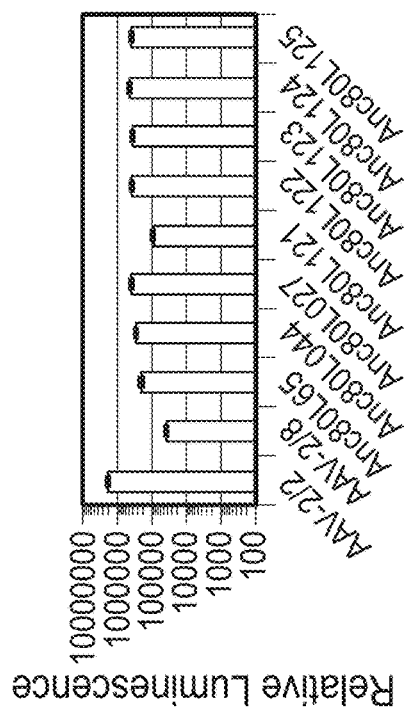
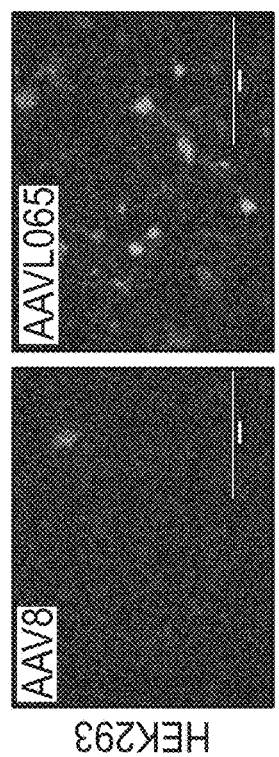
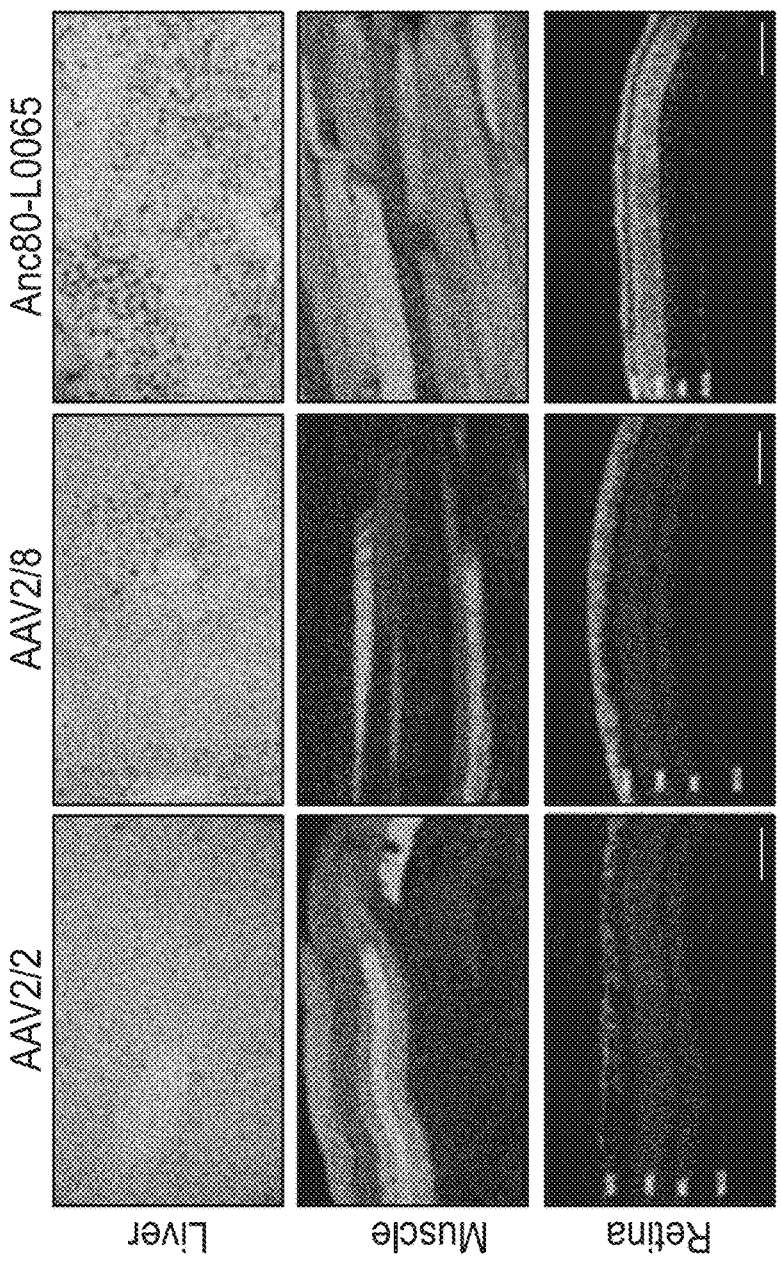
FIG. 10A
FIG. 10B
FIG. 10C

FIG. 11A

| | L0065 | Anc81 | Anc126 | Anc127 | Anc82 | Anc83 | Anc84 | Anc110 | AAV8 | Anc113 | AAV7 | AAV3 | AAV1 | AAV2 | AAV9 |
|---|---|---|---|---|---|---|---|---|---|---|---|---|---|---|---|
| L0065 | ID | 97.8% | 97.2% | 95.5% | 95.5% | 94.0% | 92.1% | 94.0% | 90.7% | 93.4% | 90.7% | 90.5% | 89.5% | 87.9% | 86.1% |
| Anc81 | | ID | 95.9% | 93.6% | 97.4% | 95.6% | 93.9% | 95.1% | 92.1% | 94.7% | 91.4% | 88.6% | 88.3% | 86.7% | 86.5% |
| Anc126 | | | ID | 97.4% | 93.4% | 92.0% | 90.7% | 92.5% | 89.1% | 91.8% | 88.8% | 91.9% | 91.5% | 89.2% | 85.8% |
| Anc127 | | | | ID | 91.7% | 90.7% | 89.7% | 90.7% | 88.3% | 89.8% | 87.3% | 94.4% | 89.4% | 90.7% | 86.0% |
| Anc82 | | | | | ID | 98.2% | 96.2% | 97.4% | 94.7% | 92.8% | 89.7% | 86.8% | 86.4% | 85.2% | 87.8% |
| Anc83 | | | | | | ID | 97.8% | 95.6% | 96.0% | 91.7% | 89.3% | 86.1% | 85.3% | 84.8% | 87.1% |
| Anc84 | | | | | | | ID | 93.7% | 94.5% | 91.3% | 89.1% | 85.5% | 85.0% | 84.1% | 86.3% |
| Anc110 | | | | | | | | ID | 92.5% | 90.5% | 88.2% | 86.3% | 86.5% | 85.6% | 89.0% |
| AAV8 | | | | | | | | | ID | 89.7% | 96.4% | 85.9% | 86.5% | 82.9% | 85.2% |
| Anc113 | | | | | | | | | | ID | 87.8% | 85.3% | 84.0% | 83.8% | 83.3% |
| AAV7 | | | | | | | | | | | ID | 84.2% | 86.7% | 82.3% | 81.8% |
| AAV3 | | | | | | | | | | | | ID | 86.4% | 87.3% | 83.7% |
| AAV1 | | | | | | | | | | | | | ID | 83.2% | 82.4% |
| AAV2 | | | | | | | | | | | | | | ID | 81.9% |
| AAV9 | | | | | | | | | | | | | | | ID |

| | Anc81 | Anc126 | Anc127 | Anc82 | Anc83 | Anc84 | Anc110 | AAV8 | AAV3 | Anc113 | AAV7 | AAV2 | AAV1 | AAV9 |
|---|---|---|---|---|---|---|---|---|---|---|---|---|---|---|
| L0065 | 97.3% | 96.6% | 94.9% | 94.3% | 92.1% | 90.2% | 92.1% | 88.5% | 90.6% | 92.1% | 88.7% | 86.8% | 84.1% | — |
| Anc81 | ID | 94.7% | 92.7% | 96.6% | 94.3% | 92.7% | 93.6% | 90.4% | 88.4% | 93.4% | 89.7% | 87.4% | 85.2% | 84.4% |
| Anc126 | | ID | 97.5% | 91.5% | 89.7% | 88.7% | 89.9% | 86.7% | 88.4% | 89.9% | 86.5% | 90.8% | 89.5% | 83.3% |
| Anc127 | | | ID | 90.2% | 88.7% | 88.0% | 89.9% | 86.3% | 92.6% | 88.2% | 86.5% | 92.1% | 87.6% | 83.1% |
| Anc82 | | | | ID | 97.7% | 95.7% | 97.0% | 86.3% | 94.9% | 90.6% | 85.2% | 85.6% | 82.8% | 86.3% |
| Anc83 | | | | | ID | 97.7% | 94.7% | 93.8% | 86.1% | 89.3% | 87.1% | 85.6% | 81.4% | 85.6% |
| Anc84 | | | | | | ID | 92.8% | 95.5% | 85.0% | 88.4% | 86.3% | 84.8% | 81.6% | 84.6% |
| Anc110 | | | | | | | ID | 93.4% | 84.8% | 88.0% | 85.8% | 84.4% | 81.6% | 87.8% |
| AAV8 | | | | | | | | ID | 91.4% | 88.0% | 85.6% | 85.7% | 82.4% | 82.4% |
| AAV3 | | | | | | | | | ID | 84.5% | 86.7% | 84.5% | 80.1% | 80.9% |
| Anc113 | | | | | | | | | | ID | 85.4% | 82.8% | 85.7% | 80.5% |
| AAV7 | | | | | | | | | | | ID | 95.8% | 83.5% | 80.5% |
| AAV2 | | | | | | | | | | | | ID | 82.4% | 78.9% |
| AAV1 | | | | | | | | | | | | | ID | 81.4% |
| AAV9 | | | | | | | | | | | | | | ID |

FIG. 11B

| Viral Production Relative to AAV8 (%) | |
|---|---|
| Anc80-L0065 | 21.75% |
| Anc81 | 54.14% |
| Anc82 | 100.99% |
| Anc83 | 76.86% |
| Anc84 | 91.20% |
| Anc110 | 118.97% |
| Anc113 | 183.10% |
| Anc126 | 2.71% |
| Anc127 | 25.34% |
| AAV2 | 32.56% |
| Neg | 0.27% |

FIG. 13

| | Viral Infectivity Relative to AAV8 (%) |
|---|---|
| Anc80-L0065 | 850.83% |
| Anc81 | 102.26% |
| Anc82 | 28.31% |
| Anc83 | 47.36% |
| Anc84 | 68.78% |
| Anc110 | 24.56% |
| Anc113 | 117.12% |
| Anc127 | 113.78% |
| AAV2 | 5225.61% |
| Neg | 0.35% |

FIG. 16

| | AAV8 | AAV2 | Anc80-L0065 | Anc81 | Anc82 | Anc83 | Anc84 | Anc110 | Anc113 | Anc126 | Anc127 |
|---|---|---|---|---|---|---|---|---|---|---|---|
| Infectivity | = | +++ | +++ | = | - | - | - | -- | = | ND | = |
| Production | = | - | -- | - | = | = | = | = | ++ | -- | - |

Key
+++ : > 225%
++ : 175% - 224.5%
+ : 125% - 174.9%
= : 75% - 124.9%
- : 25-74.9%
-- : 0-24.9%
ND : Not Determined

FIG. 17

METHODS OF PREDICTING ANCESTRAL VIRUS SEQUENCES AND USES THEREOF

CROSS REFERENCE TO RELATED APPLICATIONS

This application is a Divisional application of, and claims the benefit under 35 U.S.C. § 121 to, U.S. application Ser. No. 16/179,524, filed Nov. 2, 2018, which is a Divisional application of, and claims the benefit under 35 U.S.C. § 121 to, U.S. application Ser. No. 15/633,292, filed Jun. 26, 2017, now U.S. Pat. No. 10,119,125, which is a Divisional application of, and claims the benefit under 35 U.S.C. § 121 to, U.S. application Ser. No. 15/291,470, filed Oct. 12, 2016, now U.S. Pat. No. 9,719,070, which is a Divisional application of, and claims the benefit under 35 U.S.C. § 121 to, U.S. application Ser. No. 15/095,856, filed Apr. 11, 2016, now U.S. Pat. No. 9,695,220, which is a Continuation-In-Part of International Application No. PCT/US2014/060163 filed Oct. 10, 2014, which claims the benefit of priority under 35 U.S.C. § 119(e) to U.S. Application No. 61/889,827, filed Oct. 11, 2013, the contents of all of which are incorporated herein by reference in their entireties.

TECHNICAL FIELD

This disclosure generally relates to viruses.

BACKGROUND

Circumventing and avoiding a neutralizing or toxic immune response against a gene therapy vector is a major challenge with all gene transfer vector types. Gene transfer to date is most efficiently achieved using vectors based on viruses circulating in humans and animals, e.g., adenovirus and adeno-associated virus (AAV). However, if subjects have been naturally infected with a virus, a subsequent treatment with a vector based on that virus leads to increased safety risks and decreased efficiency of gene transfer due to cellular and humoral immune responses. Capsid antigens are primarily responsible for the innate and/or adaptive immunity toward virus particles, however, viral gene-encoded polypeptides also can be immunogenic.

SUMMARY

This disclosure describes methods of predicting and synthesizing ancestral viral sequences or portions thereof, and also describes virus particles containing such ancestral viral sequences. The methods described herein were applied to adeno-associated virus (AAV); thus, this disclosure describes predicted ancestral AAV sequences and AAV virus particles containing such ancestral AAV sequences. This disclosure also describes the reduced seroprevalance exhibited by virus particles containing ancestral sequences relative to virus particles containing contemporary sequences.

In one aspect, this disclosure includes adeno-associated virus (AAV) capsid polypeptides, e.g., synthetic and/or artificial AAV capsid polypeptides, having an amino acid sequence selected from the group consisting of SEQ ID NOs: 1, 3, 5, 7, 9, 11, 13, 15 and 17. In some implementations, the AAV capsid polypeptides or virus particles comprising the AAV capsid polypeptides exhibit a lower seroprevalence than do an AAV2 capsid polypeptide or a virus particle comprising an AAV2 capsid polypeptide, and the AAV capsid polypeptides or virus particles comprising the AAV capsid polypeptides exhibit about the same or a lower seroprevalence than do an AAV8 capsid polypeptide or a virus particle comprising an AAV8 capsid polypeptide. In some embodiments, the AAV capsid polypeptides or virus particles comprising the AAV capsid polypeptides are neutralized to a lesser extent by human serum than is an AAV2 capsid polypeptide or a virus particle comprising an AAV2 capsid polypeptide, and the AAV capsid polypeptides or virus particles comprising the AAV capsid polypeptides are neutralized to a similar or lesser extent by human serum as is an AAV8 capsid polypeptide or a virus particle comprising an AAV8 capsid polypeptide. In some embodiments, the AAV capsid polypeptides are purified. The AAV capsid polypeptides provided herein can be encoded by a nucleic acid sequence selected from the group consisting of SEQ ID NOs: 2, 4, 6, 8, 10, 12, 14, 16, and 18.

In one aspect, the disclosure provides nucleic acid molecules, e.g., synthetic and/or artificial nucleic acid molecules, encoding an adeno-associated virus (AAV) capsid polypeptide having a nucleic acid sequence selected from the group consisting of SEQ ID NOs: 2, 4, 6, 8, 10, 12, 14, 16, and 18. Also provided are vectors that includes such a nucleic acid, and a host cell that includes such a vector.

In another aspect, the disclosure provides purified virus particles that include an AAV capsid polypeptide described herein. In some embodiments, the virus particles include a transgene.

In other aspects, the disclosure provides adeno-associated virus (AAV) capsid polypeptides, e.g., synthetic and/or artificial AAV capsid polypeptides, having at least 95% (e.g., 97, 98, 99, or 100%) sequence identity to an amino acid sequence selected from the group consisting of SEQ ID NOs: 19, 20, 21, 22, 23, 24, 25 and 26. In some embodiments, the AAV capsid polypeptides or virus particles comprising the AAV capsid polypeptide exhibit a lower seroprevalence than does an AAV2 capsid polypeptide or a virus particle comprising an AAV2 capsid polypeptide, and the AAV capsid polypeptide or a virus particle comprising the AAV capsid polypeptide exhibit about the same or a lower seroprevalence than does an AAV8 capsid polypeptide or a virus particle comprising an AAV8 capsid polypeptide. In some embodiments, the AAV capsid polypeptides or virus particles comprising the AAV capsid polypeptide are neutralized to a lesser extent by human serum than is an AAV2 capsid polypeptide or a virus particle comprising an AAV2 capsid polypeptide, and the AAV capsid polypeptide and a virus particle comprising the AAV capsid polypeptide is neutralized to a similar or lesser extent by human serum as is an AAV8 capsid polypeptide or a virus particle comprising an AAV8 capsid polypeptide. In some embodiments, the AAV capsid polypeptides are purified.

In another aspect, the AAV capsid polypeptides described herein can be encoded by nucleic acid sequences as described herein. In one implementation, the disclosure provides nucleic acid molecules encoding an adeno-associated virus (AAV) capsid polypeptide, wherein the nucleic acid molecules have at least 95% (e.g., 97, 98, 99, or 100%) sequence identity to a nucleic acid sequence as shown herein. The disclosure also provides vectors including such nucleic acid molecules, as are host cells that include such a vector.

In one aspect, the disclosure provides virus particles that include at least one of the AAV capsid polypeptides described herein. In some embodiments, the virus particles include a transgene.

In certain aspects, the disclosure provides methods of administering a virus particle as described herein to a subject in need of gene transfer or vaccination. In some embodiments, the virus particles exhibit less seroprevalence than does an AAV2 virus particle. In some embodiments, the virus particles exhibit about the same or less seroprevalence than does an AAV8 virus particle. In some embodiments, the virus particles are neutralized to a lesser extent by human serum than is an AAV2 virus particle, and the AAV virus particles are neutralized to a similar or lesser extent by human serum than is an AAV8 virus particle.

In one aspect, the disclosure provides methods of administering a target antigen operably linked to an AAV capsid polypeptide as described herein to a subject in need of vaccination. In some embodiments, the AAV capsid polypeptides exhibit less seroprevalence than does an AAV2 capsid polypeptide. In some embodiments, the AAV capsid polypeptide exhibits about the same or less seroprevalence than does an AAV8 capsid polypeptide. In some embodiments, the AAV capsid polypeptides are neutralized to a lesser extent by human serum than is an AAV2 capsid polypeptide, and the AAV capsid polypeptide is neutralized to a similar or lesser extent by human serum than is an AAV8 capsid polypeptide.

In another aspect, the disclosure provides in silico methods of predicting a sequence of an ancestral virus or portion thereof. Such methods typically include providing nucleotide or amino acid sequences from a plurality of contemporary viruses or portions thereof; aligning the sequences using a multiple sequence alignment (MSA) algorithm; modeling evolution to obtain a predicted ancestral phylogeny of the plurality of contemporary viruses or portions thereof; estimating, at a phylogenic node of the predicted ancestral phylogeny, the evolutionary probability of a particular nucleotide or amino acid residue at each position of the sequence; and predicting, based on the estimated probability at each position, a sequence of an ancestral virus or portion thereof.

In some embodiments, one or more, or all, of the steps are performed using a computer processor. In some embodiments, the MSA algorithm uses phylogenetic information to predict if a gap in the alignment is a result of a deletion or an insertion. In some embodiments, the MSA algorithm is a Probabilistic Alignment Kit (PRANK). In some embodiments, the model used for modeling evolution is selected using Aikake Information Criterion (AIC). In some embodiments, the predicted ancestral phylogeny is obtained using a JTT model with a Gamma distribution model ("+G") and a frequency calculation of πi ("+F"). In some embodiments, the modeling the evolution step is performed using a JTT+G+F model. In some embodiments, the methods include synthesizing, based on the predicted sequence, the ancestral virus or portion thereof. In some embodiments, the methods include assembling the ancestral virus or portion thereof into an ancestral virus particle.

In some embodiments, the methods also include screening the ancestral virus particle for at least one of the following: (a) replication; (b) gene transfer properties; (c) receptor binding; or (d) seroprevalence. In some embodiments, the ancestral virus particles exhibit less seroprevalence than does a virus particle assembled from at least one of the plurality of contemporary viruses or portions thereof. In some embodiments, the ancestral virus particle is neutralized to a lesser extent by human serum than is a virus particle assembled from at least one of the plurality of contemporary viruses or portions thereof. In some embodiments, the plurality of contemporary viruses or portions thereof belong to a family selected from the group consisting of adenovirus (AV), human immunodeficiency virus (HIV), retrovirus, lentivirus, herpes simplex virus (HSV), vaccinia virus, pox virus, influenza virus, respiratory syncytial virus, parainfluenza virus, and foamy virus.

Thus, the present disclosure provides ancestral viruses or portions thereof that exhibit reduced susceptibility to pre-existing immunity in current day human populations than do contemporary viruses or portions thereof. Generally, the reduced susceptibility to pre-existing immunity exhibited by the ancestral viruses or portions thereof in current day human populations is reflected as a reduced susceptibility to neutralizing antibodies.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

The patent or application file contains at least one drawing executed in color. Copies of this patent or patent application publication with color drawings will be provided by the Office upon request and payment of the necessary fee.

FIG. 1 is a schematic showing the relationships between ancestral/contemporary viral infections and ancestral/contemporary host immune response.

FIGS. 2A to 2D are a series of schematics showing an example of an ancestral reconstruction procedure. Data shown are excerpted from a full dataset and represent residues 564-584 (AAV2-VP1 numbering; SEQ ID NOs: 37-43 (top to bottom)).

FIG. 3 illustrates a phylogenetic tree of AAV contemporary sequences generated using the methods described herein.

FIG. 4 illustrates an alignment of ancestral AAV VP1 polypeptides (SEQ ID NOs: 23, 19, 24, 25, 26, 20, 21 and 22, top to bottom).

FIGS. 5A and 5B together illustrate an alignment of functional ancestral AAV VP1 polypeptides and contemporary AAV VP1 polypeptides (SEQ ID NOs: 23, 19, 24, 25 21, 22, 26, 20, 27, 28, 29, 30, 31, 32, 33 and 34, top to bottom).

FIG. 6 is an electrophoretic gel demonstrating that ancestral AAV VP1 sequences are transcribed and alternately spliced in a manner similar to that for contemporary AAV VP1 sequences.

FIG. 7 is a graph showing the luciferase activity in HEK293 cells transduced with ancestral AAV vectors.

FIG. 8 is a graph showing the sequence comparison (% up from diagonal, # of aa differences below) between the Anc80 library and Anc80L65.

FIGS. 9A-D are images of experimental results demonstrating that Anc80L65 is capable of assembling and yielding particles of high titer. Panel A shows that Anc80L65 is able to produce vector yields equivalent to AAV2; Panel B is a TEM image of virus particles that include Anc80L65; Panel C shows that virus particles that include Anc80L65 are able to produce AAV cap VP1, 2 and 3 proteins based on SDS-PAGE gel under denaturing conditions; and Panel D shows a Western blot of Anc80L65 using the AAV capsid antibody, B1.

FIGS. 10A-C are images of experimental results demonstrating that Anc80L65 is able to infect cells in vitro on HEK293 cells using GFP as readout (Panel A) or luciferase (Panel B) versus AAV2 and/or AAV8 controls and also is efficient at targeting liver following an IV injection of AAV encoding a nuclear LacZ transgene (top row, Panel C: liver), following direct IM injection of an AAV encoding GFP (middle row, Panel C: muscle), and following sub-retinal injection with AAV encoding GFP (bottom row, Panel C: retina).

FIGS. 11A and 11B are sequence identity matrices producing using MAFFT that show the amino acid sequences of the VP1 proteins of ancestral vectors aligned with those of representative extant AAVs (FIG. 11A), and the amino acid sequences of the VP3 proteins of ancestral vectors aligned with those of representative extant AAVs (FIG. 11B).

FIG. 13 is a table showing the titers of each vector, averaged and compared, to those of AAV8.

FIG. 16 is a table showing the luminescence of cells transduced by each vector, which were averaged and compared to those of AAV8.

FIG. 17 is a chart that provides a summary of in vitro experiments to determine the relative production and infectivity of the ancestral AAV vectors described herein.

DETAILED DESCRIPTION

Gene transfer, either for experimental or therapeutic purposes, relies upon a vector or vector system to shuttle genetic information into target cells. The vector or vector system is considered the major determinant of efficiency, specificity, host response, pharmacology, and longevity of the gene transfer reaction. Currently, the most efficient and effective way to accomplish gene transfer is through the use of vectors or vector systems based on viruses that have been made replication-defective.

Seroprevalence studies, however, indicate that significant proportions of worldwide human populations have been pre-exposed (e.g., by natural infection) to a large number of the viruses currently used in gene transfer and, therefore, harbor pre-existing immunity. Neutralizing antibodies toward the viral vector in these pre-exposed individuals are known to limit, sometimes significantly, the extent of gene transfer or even re-direct the virus away from the target. See, for example, Calcedo et al. (2009, J. Infect. Dis., 199:381-90) and Boutin et al. (2010, Human Gene Ther., 21:704-12). Thus, the present disclosure is based on the recognition that ancestral viruses or portions thereof exhibit reduced susceptibility to pre-existing immunity (e.g., reduced susceptibility to neutralizing antibodies) in current day human populations than do contemporary viruses or portions thereof.

Figure 1:
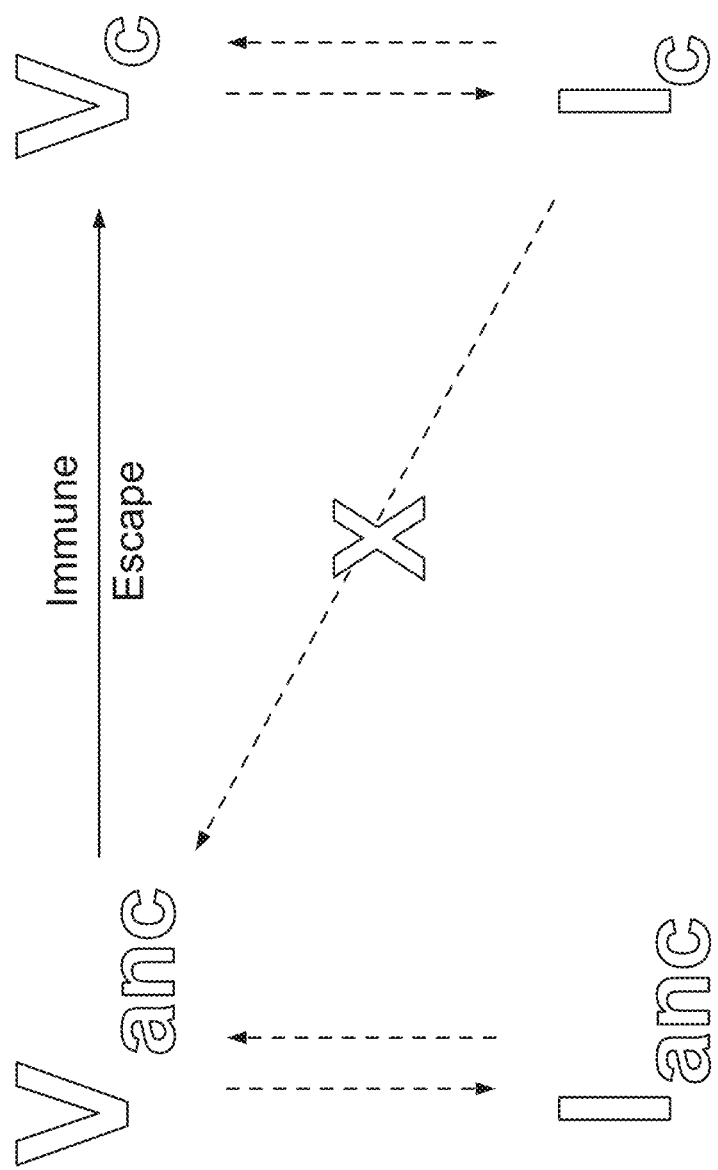

FIG. 1 is a schematic showing the relationships between ancestral and contemporary viral infections and ancestral and contemporary host immune response. FIG. 1 shows how ancestral AAVs can be refractory to contemporary pre-existing immunity. A contemporary, extant virus (Vc) is presumed to have evolved from an ancestral species (Vanc), primarily under evolutionary pressures of host immunity through mechanisms of immune escape. Each of these species, Vanc and Vc, have the ability to induce adaptive immunity including B and T cell immunity (Ianc and Ic, respectively). It was hypothesized, and confirmed herein, that immunity induced by contemporary viruses does not necessarily cross-react with an ancestral viral species, which can be substantially different in terms of epitope composition than the extant virus.

This disclosure provides methods of predicting the sequence of an ancestral virus or a portion thereof. One or more of the ancestral virus sequences predicted using the methods described herein can be generated and assembled into a virus particle. As demonstrated herein, virus particles assembled from predicted ancestral viral sequences can exhibit less, sometimes significantly less, seroprevalence than current-day, contemporary virus particles. Thus, the ancestral virus sequences disclosed herein are suitable for use in vectors or vector systems for gene transfer.

Methods of Predicting and Synthesizing an Ancestral Viral Sequence

To predict an ancestral viral sequence, nucleotide or amino acid sequences first are compiled from a plurality of contemporary viruses or portions thereof. While the methods described herein were exemplified using adeno-associated virus (AAV) capsid sequences, the same methods can be applied to other sequences from AAV (e.g., the entire genome, rep sequences, ITR sequences) or to any other virus or portion thereof. Viruses other than AAV include, without limitation, adenovirus (AV), human immunodeficiency virus (HIV), retrovirus, lentivirus, herpes simplex virus (HSV), measles, vaccinia virus, pox virus, influenza virus, respiratory syncytial virus, parainfluenza virus, foamy virus, or any other virus to which pre-existing immunity is considered a problem.

Sequences from as few as two contemporary viruses or portions thereof can be used, however, it is understood that a larger number of sequences of contemporary viruses or portions thereof is desirable so as to include as much of the landscape of modern day sequence diversity as possible, but also because a larger number of sequences can increase the predictive capabilities of the algorithms described and used. For example, sequences from 10 or more contemporary viruses or portions thereof can be used, sequences from 50 or more contemporary viruses or portions thereof can be used, or sequences from 100 or more contemporary viruses or portions thereof can be used.

Such sequences can be obtained, for example, from any number of public databases including, without limitation, GenBank, UniProt, EMBL, International Nucleotide Sequence Database Collaboration (INSDC), or European Nucleotide Archive. Additionally or alternatively, such sequences can be obtained from a database that is specific to a particular organism (e.g., HIV database). The contemporary sequences can correspond to the entire genome, or only a portion of the genome can be used such as, without limitation, sequences that encode one or more components of the viral capsid, the replication protein, or the ITR sequences.

Next, the contemporary sequences are aligned using a multiple sequence alignment (MSA) algorithm. FIG. 2A is a schematic showing an alignment of multiple sequences. MSA algorithms are well known in the art and generally are designed to be applied to different size datasets and different inputs (e.g., nucleic acid or protein), and to align the sequences in a particular manner (e.g., dynamic programming, progressive, heuristic) and apply different scoring schemes in the alignment (e.g., matrix-based or consistency-based, e.g., minimum entropy, sum of pairs, similarity matrix, gap scores). Well known MSA algorithms include, for example, ClustalW (Thompson et al., 1994, Nuc. Acids Res., 22:4673-90), Kalign (Lassmann et al., 2006, Nuc. Acids Res., 34:W596-99), MAFFT (Katoh et al., 2005, Nuc. Acids Res., 33:511-8), MUSCLE (Edgar, 2004, BMC Bioinform., 5:113), and T-Coffee (Notredame et al., 2000, J. Mol. Biol., 302:205-17).

As described herein, one of the main features when selecting a MSA algorithm for use in the methods described herein is the manner in which the algorithm treats a gap in the alignment. Gaps in a sequence alignment can be assigned a penalty value that is either dependent or independent on the size of the gap. In the present methods, it is preferred that the MSA algorithm used in the methods described herein apply phylogenetic information to predict whether a gap in the alignment is a result of a deletion or an insertion as opposed to a biased, non-phylogenetic treatment of gaps due to, e.g., insertions and/or deletions. A suitable method of treating gaps in alignments and evolutionary analysis is described in Loytynoja and Goldman, 2008, Science, 320: 1632-5, and commercially available algorithms that apply gaps in alignments in a manner that is suitable for use in the methods described herein is a Probabilistic Alignment Kit (PRANK; Goldman Group Software; Loytynoja and Goldman, 2005, PNAS USA, 102:10557-62), and variations of the PRANK algorithm.

An evolutionary model is then applied to the resulting alignment to obtain a predicted ancestral phylogeny (see FIG. 2B). There are a number of evolutionary models available in the art, each of which apply slightly different matrices of replacement rates for amino acids. Without limitation, algorithms for applying models of evolution include the Dayhoff models (e.g., PAM120, PAM160, PAM250; Dayhoff et al., 1978, In *Atlas of Protein Sequence and Structure* (ed. Dayhoff), pp. 345-52, National Biomedical Research Foundation, Washington D.C.), the JTT model (Jones et al., 1992, Comp. Appl. Biosci., 8:275-82), the WAG model (Whelan and Goldman, 2001, Mol. Biol. Evol., 18:691-9), and the Blosum models (e.g., Blosum45, Blosum62, Blosum80; Henikoff and Henikoff, 1992, PNAS USA, 89:10915-9).

In addition, the constraints that structure and function impose on an evolutionary model can themselves be modeled, for example, by considering that some positions are invariant ("+I"; Reeves, 1992, J. Mol. Evol., 35:17-31), that some positions undergo different rates of change ("+G"; Yang, 1993, Mol. Biol. Evol., 10:1396-1401), and/or that equilibrium frequencies of nucleotides or amino acids are the same as those in the alignment ("+F"; Cao et al., 1994, J. Mol. Evol., 39:519-27).

The fitness of one or more models of evolution can be evaluated using the Aikake Information Criterion (AIC; Akaike, 1973, In *Second International Symposium on Information Theory*, Petrov and Csaki, eds., pp 267-81, Budapest, Akademiai Kiado), the Bayesian Information Criterion (BIC; Schwarz, 1978, Ann. Statist. 6:461-4), or variations or combinations thereof. In addition, AIC, BIC, or variations or combinations thereof can be used to evaluate the relative importance of including one or more parameters (e.g., the constraints discussed above) in the evolutionary model.

As explained in the Example section below, ProTest3 (Darriba et al., 2011, Bioinformatics, 27(8):1164-5) can be used to determine, based on the lowest AIC, that a JTT+G+F algorithm was the most suitable model for AAV evolution. It would be understood by a skilled artisan that a JTT+G+F algorithm also may be used to predict ancestral viral sequences other than AAV capsid polypeptides, however, it also would be understood by a skilled artisan that, depending on the dataset and the fitness score, a different model of evolution may be more suitable.

Once a model of evolution has been selected and its fitness determined, a phylogenetic tree of the virus sequences or portions thereof can be constructed. Constructing phylogenetic trees is known in the art and typically employs maximum likelihood methods such as those implemented by PhyML (Guindon and Gascuel, 2003, Systematic Biology, 52:696-704)), MOLPHY (Adachi and Hasegawa, 1996, ed. Tokyo Institute of Statistical Mathematics), BioNJ (Gascuel, 1997, Mol. Biol. Evol., 14:685-95), or PHYLIP (Felsenstein, 1973, Systematic Biology, 22:240-9). A skilled artisan would understand that a balance between computational complexity and the goodness of fit is desirable in a model of amino acid substitutions.

If desired, the phylogenetic tree can be assessed for significance. A number of statistical methods are available and routinely used to evaluate the significance of a model including, without limitation, bootstrap, jackknife, cross-validation, permutation tests, or combinations or variations thereof. Significance also can be evaluated using, for example, an approximate likelihood-ratio test (aLRT; Anisimova and Gascuel, 2006, Systematic Biology, 55:539-52)).

At any phylogenetic node of the phylogeny (e.g., an interior phylogenetic node), the sequence can be reconstructed by estimating the evolutionary probability of a particular nucleotide or amino acid residue at each position of the sequence (FIG. 2C). A phylogenic node refers to an intermediate evolutionary branch point within the predicted ancestral phylogeny. As used herein, "evolutionary probability" refers to the probability of the presence of a particular nucleotide or amino acid at a particular position based on an evolutionary model as opposed to a model that does not take into account, for example, an evolutionary shift in the codon usage. Exemplary models that take into account the evolutionary probability of a particular nucleotide or amino acid residue at a particular position can be estimated using, for example, any number of maximum likelihood methods including, without limitation, Phylogenetic Analysis by Maximum Likelihood (PAML; Yang, 1997, Comp. Applic. BioSci., 13:555-6) or Phylogenetic Analysis Using Parsimony (PAUP; Sinauer Assoc., Inc., Sunderland, Mass.).

Based on the estimated evolutionary probability of a particular nucleotide or amino acid residue at each position, the predicted sequence of an ancestral virus or portion thereof can be assembled to form a complete or partial synthetic nucleic acid or polypeptide sequence. If desired, the likelihood that any residue was in a given state at a given node along the node can be calculated, and any position along the sequence having a calculated posterior probability beneath a particular threshold can be identified (FIG. 2D). In this manner, an ancestral scaffold sequence can be generated, which can include variations at those positions having a probability below the particular threshold.

If the ancestral sequence that is predicted using the methods herein is a nucleic acid sequence, the sequence then can be codon optimized so that it can be efficiently translated into an amino acid sequence. Codon usage tables for different organisms are known in the art. Optionally, however, a codon usage table can be designed based on one or more contemporary sequences that has homology (e.g., at least 90% sequence identity) to the ancestral scaffold sequence, and an ancestral sequence as described herein can be codon optimized toward mammalian (e.g., human) codon usage.

Any or all of the steps outlined herein for predicting an ancestral viral sequence can be performed or simulated on a computer (e.g., in silico) using a processor or a microprocessor.

Ancestral Adeno-Associated Virus (AAV) Scaffold Sequences

Figure 3:
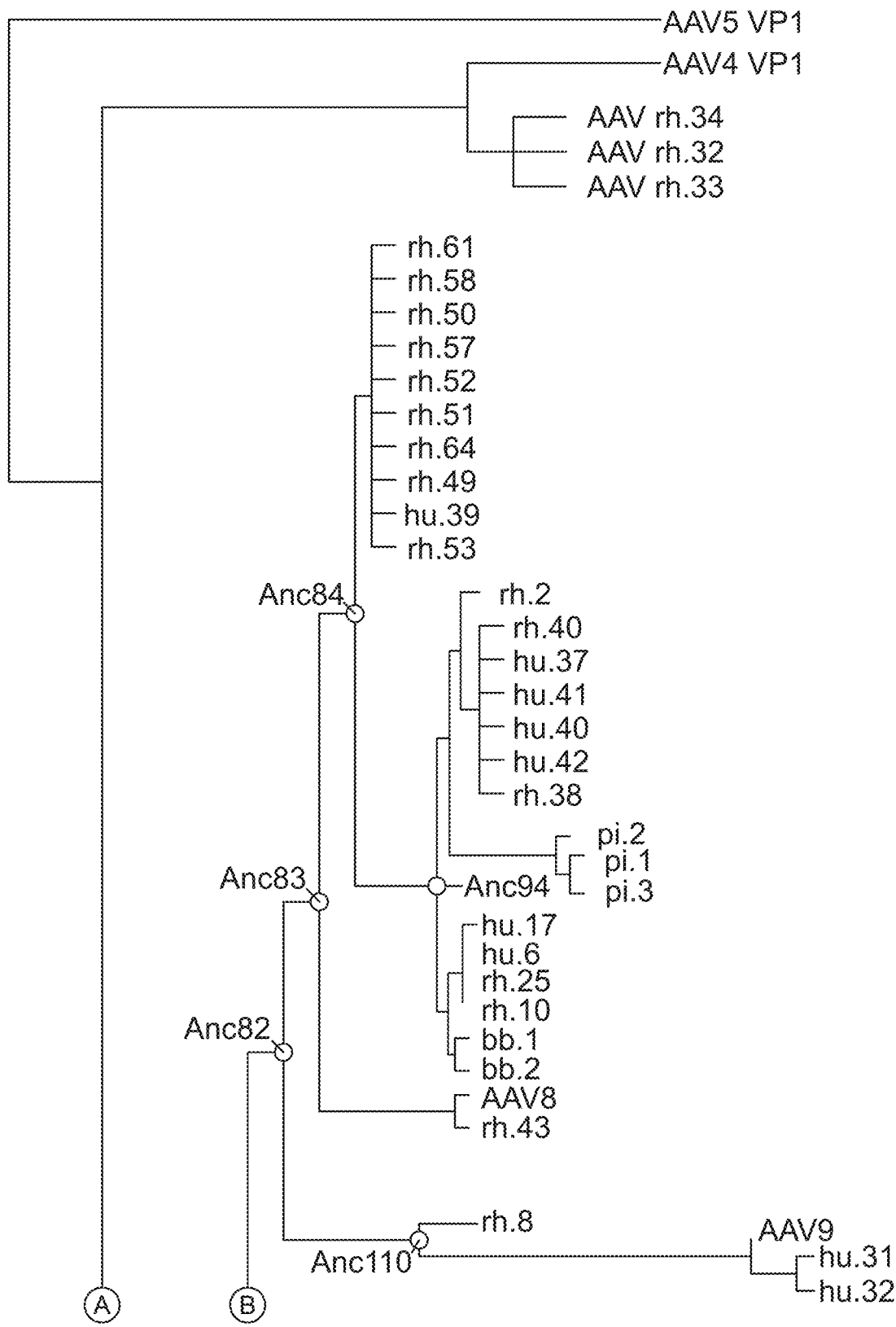
Figure 3:
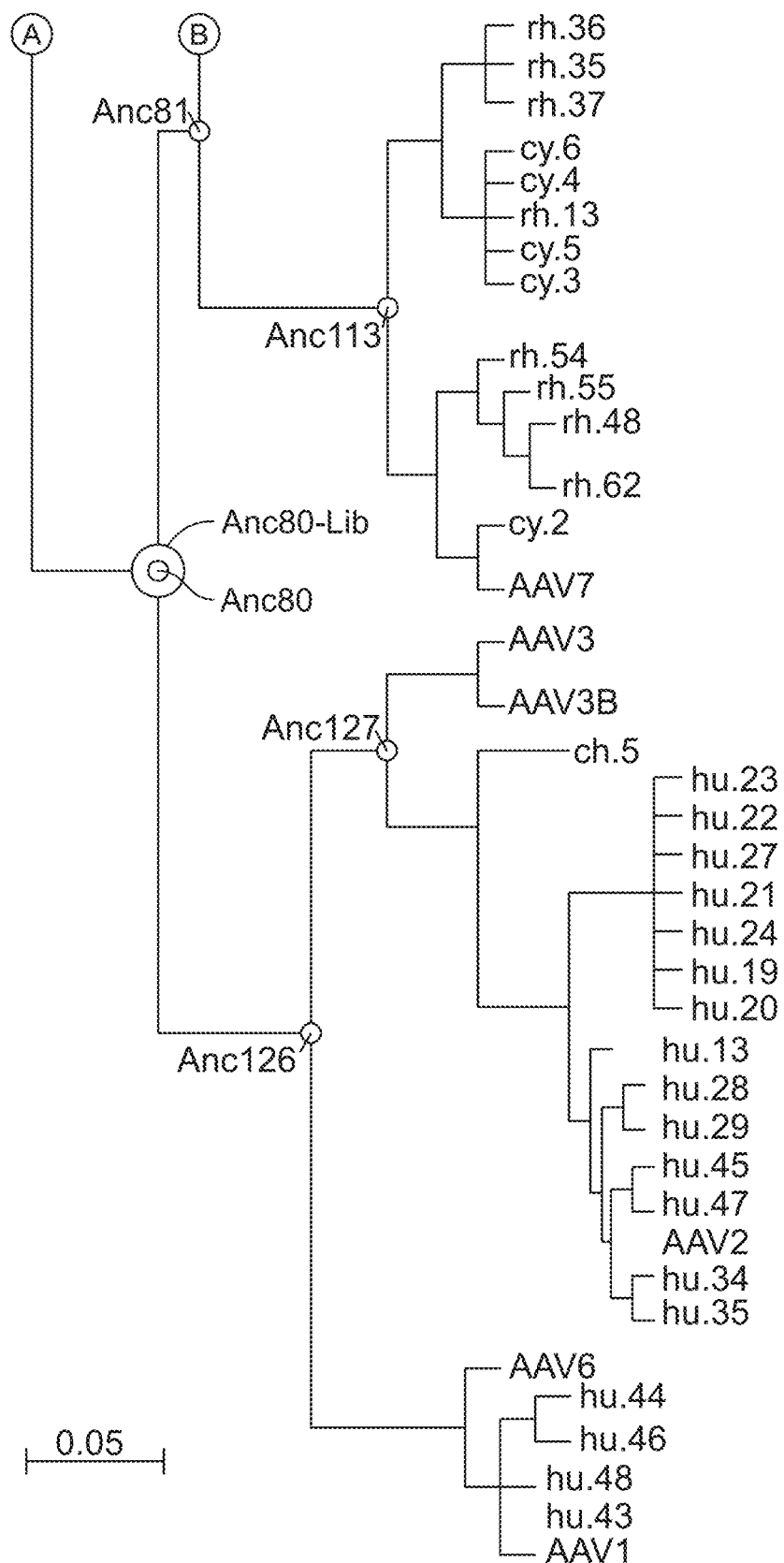

The methods described herein were applied to adeno-associated virus (AAV) using contemporary capsid sequences (described in detail in the Examples below). AAV is widely considered as a therapeutic gene transfer vector and a genetic vaccine vehicle, but exhibits a high seroprevalence in human populations. Using the methods described herein, a phylogenetic tree was assembled using contemporary AAV sequences (see FIGS. 3A-3C) and predicted ancestral scaffold sequences were obtained at the designated phylogenic node (Table 1). As used herein, an ancestral scaffold sequence refers to a sequence that is constructed using the methods described herein (e.g., using evolutionary probabilities and evolutionary modeling) and is not known to have existed in nature. As used herein, the ancestral scaffold sequences are different from consensus sequences, which are typically constructed using the frequency of nucleotides or amino acid residues at a particular position.

TABLE 1

| Node | Polypeptide (SEQ ID NO) | Nucleic Acid (SEQ ID NO) |
| --- | --- | --- |
| Anc80 | 1 | 2 |
| Anc81 | 3 | 4 |
| Anc82 | 5 | 6 |
| Anc83 | 7 | 8 |
| Anc84 | 9 | 10 |
| Anc94 | 11 | 12 |
| Anc113 | 13 | 14 |
| Anc126 | 15 | 16 |
| Anc127 | 17 | 18 |

The scaffold sequence of the Anc80 polypeptide is shown in SEQ ID NO:1, which is encoded by the scaffold sequence of the Anc80 nucleic acid shown in SEQ ID NO:2. The scaffold sequence of Anc80 contains 11 positions at which either of two residues were probable. Therefore, the Anc80 scaffold sequence represents 2048 ($2^{11}$) different sequences.

To demonstrate the effectiveness of the methods described herein for predicting the ancestral sequence of a virus or portion thereof, a library of the 2048 predicted ancestral sequences at the AAV Anc80 node was generated and, as described herein, demonstrated to form viable virus particles exhibiting less seroprevalence, in some instances, significantly less seroprevalance, than virus particles assembled with contemporary capsid polypeptides.

Methods of Making Ancestral Virus Particles

After the predicted ancestral sequence of a virus or portion thereof has been obtained, the actual nucleic acid molecule and/or polypeptide(s) can be generated, e.g., synthesized. Methods of generating an artificial nucleic acid molecule or polypeptide based on a sequence obtained, for example, in silico, are known in the art and include, for example, chemical synthesis or recombinant cloning. Additional methods for generating nucleic acid molecules or polypeptides are known in the art and are discussed in more detail below.

Once an ancestral polypeptide has been produced, or once an ancestral nucleic acid molecule has been generated and expressed to produce an ancestral polypeptide, the ancestral polypeptide can be assembled into an ancestral virus particle using, for example, a packaging host cell. The components of a virus particle (e.g., rep sequences, cap sequences, inverted terminal repeat (ITR) sequences) can be introduced, transiently or stably, into a packaging host cell using one or more vectors as described herein. One or more of the components of a virus particle can be based on a predicted ancestral sequence as described herein, while the remaining components can be based on contemporary sequences. In some instances, the entire virus particle can be based on predicted ancestral sequences.

Such ancestral virus particles can be purified using routine methods. As used herein, "purified" virus particles refer to virus particles that are removed from components in the mixture in which they were made such as, but not limited to, viral components (e.g., rep sequences, cap sequences), packaging host cells, and partially- or incompletely-assembled virus particles.

Once assembled, the ancestral virus particles can be screened for, e.g., the ability to replicate; gene transfer properties; receptor binding ability; and/or seroprevalence in a population (e.g., a human population). Determining whether a virus particle can replicate is routine in the art and typically includes infecting a host cell with an amount of virus particles and determining if the virus particles increase in number over time. Determining whether a virus particle is capable of performing gene transfer also is routine in the art and typically includes infecting host cells with virus particles containing a transgene (e.g., a detectable transgene such as a reporter gene, discussed in more detail below). Following infection and clearance of the virus, the host cells can be evaluated for the presence or absence of the transgene. Determining whether a virus particle binds to its receptor is routine in the art, and such methods can be performed in vitro or in vivo.

Determining the seroprevalence of a virus particle is routinely performed in the art and typically includes using an immunoassay to determine the prevalence of one or more antibodies in samples (e.g., blood samples) from a particular population of individuals. Seroprevalence is understood in the art to refer to the proportion of subjects in a population that is seropositive (i.e., has been exposed to a particular pathogen or immunogen), and is calculated as the number of subjects in a population who produce an antibody against a particular pathogen or immunogen divided by the total number of individuals in the population examined. Immunoassays are well known in the art and include, without limitation, an immunodot, Western blot, enzyme immunoassays (EIA), enzyme-linked immunosorbent assay (ELISA), or radioimmunoassay (RIA). As indicated herein, ancestral virus particles exhibit less seroprevalence than do contemporary virus particles (i.e., virus particles assembled using contemporary virus sequences or portions thereof). Simply by way of example, see Xu et al. (2007, Am. J. Obstet. Gynecol., 196:43.e1-6); Paul et al. (1994, J. Infect. Dis., 169:801-6); Sauerbrei et al. (2011, Eurosurv., 16(44): 3); and Sakhria et al. (2013, PLoS Negl. Trop. Dis., 7:e2429), each of which determined seroprevalence for a particular antibody in a given population.

As described herein, ancestral virus particles are neutralized by a person's, e.g., patient's, immune system to a lesser extent than are contemporary virus particles. Several methods to determine the extent of neutralizing antibodies in a serum sample are available. For example, a neutralizing antibody assay measures the titer at which an experimental sample contains an antibody concentration that neutralizes infection by 50% or more as compared to a control sample without antibody. See, also, Fisher et al. (1997, Nature Med., 3:306-12) and Manning et al. (1998, Human Gene Ther., 9:477-85).

With respect to the ancestral AAV capsid polypeptides exemplified herein, the seroprevalence and/or extent of neutralization can be compared, for example, to an AAV8 capsid polypeptide or virus particle that includes an AAV8 capsid polypeptide, or an AAV2 capsid polypeptide or virus particle that includes an AAV2 capsid polypeptide. It is generally understood in the art that AAV8 capsid polypeptides or virus particles exhibit a seroprevalance, and a resulting neutralization, in the human population that is considered low, while AAV2 capsid polypeptide or virus particles exhibit a seroprevalance, and a resulting neutralization, in the human population that is considered high. Obviously, the particular seroprevalence will depend upon the population examined as well as the immunological methods used, but there are reports that AAV8 exhibits a seroprevalence of about 22% up to about 38%, while AAV2 exhibits a seroprevalence of about 43.5% up to about 72%. See, for example, Boutin et al., 2010, "Prevalence of serum IgG and neutralizing factors against AAV types 1, 2, 5, 6, 8 and 9 in the healthy population: implications for gene therapy using AAV vectors," Hum. Gene Ther., 21:704-12. See, also, Calcedo et al., 2009, J. Infect. Dis., 199:381-90.

Predicted Adeno Associated Virus (AAV) Ancestral Nucleic Acid and Polypeptide Sequences A number of different clones from the library encoding predicted ancestral capsid polypeptides from the Anc80 node were sequenced, and the amino acid sequences of representative AAV predicted ancestral capsid polypeptides are shown in SEQ ID NO: 19 (Anc80L27); SEQ ID NO: 20 (Anc80L59); SEQ ID NO: 21 (Anc80L60); SEQ ID NO: 22 (Anc80L62); SEQ ID NO: 23 (Anc80L65); SEQ ID NO: 24 (Anc80L33); SEQ ID NO: 25 (Anc80L36); and SEQ ID NO:26 (Anc80L44). Those skilled in the art would appreciate that the nucleic acid sequence encoding each amino acid sequence can readily be determined.

In addition to the predicted ancestral capsid polypeptides having the sequences shown in SEQ ID NOs: 19, 20, 21, 22, 23, 24, 25 or 26, polypeptides are provided that have at least 95% sequence identity (e.g., at least 96%, at least 97%, at least 98%, at least 99% or 100% sequence identity) to the predicted ancestral capsid polypeptides having the sequences shown in SEQ ID NOs: 19, 20, 21, 22, 23, 24, 25, or 26. Similarly, nucleic acid molecules are provided that have at least 95% sequence identity (e.g., at least 96%, at least 97%, at least 98%, at least 99% or 100% sequence identity) to the nucleic acid molecules encoding the ancestral capsid polypeptides (i.e., having at least 95% sequence identity).

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the algorithm described by Altschul et al. (1997, Nucleic Acids Res., 25:3389 3402) as incorporated into BLAST (basic local alignment search tool) programs, available at ncbi.nlm.nih.gov on the World Wide Web. BLAST searches can be performed to determine percent sequence identity between a sequence (nucleic acid or amino acid) and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence and another sequence, the default parameters of the respective programs generally are used.

Figure 4:
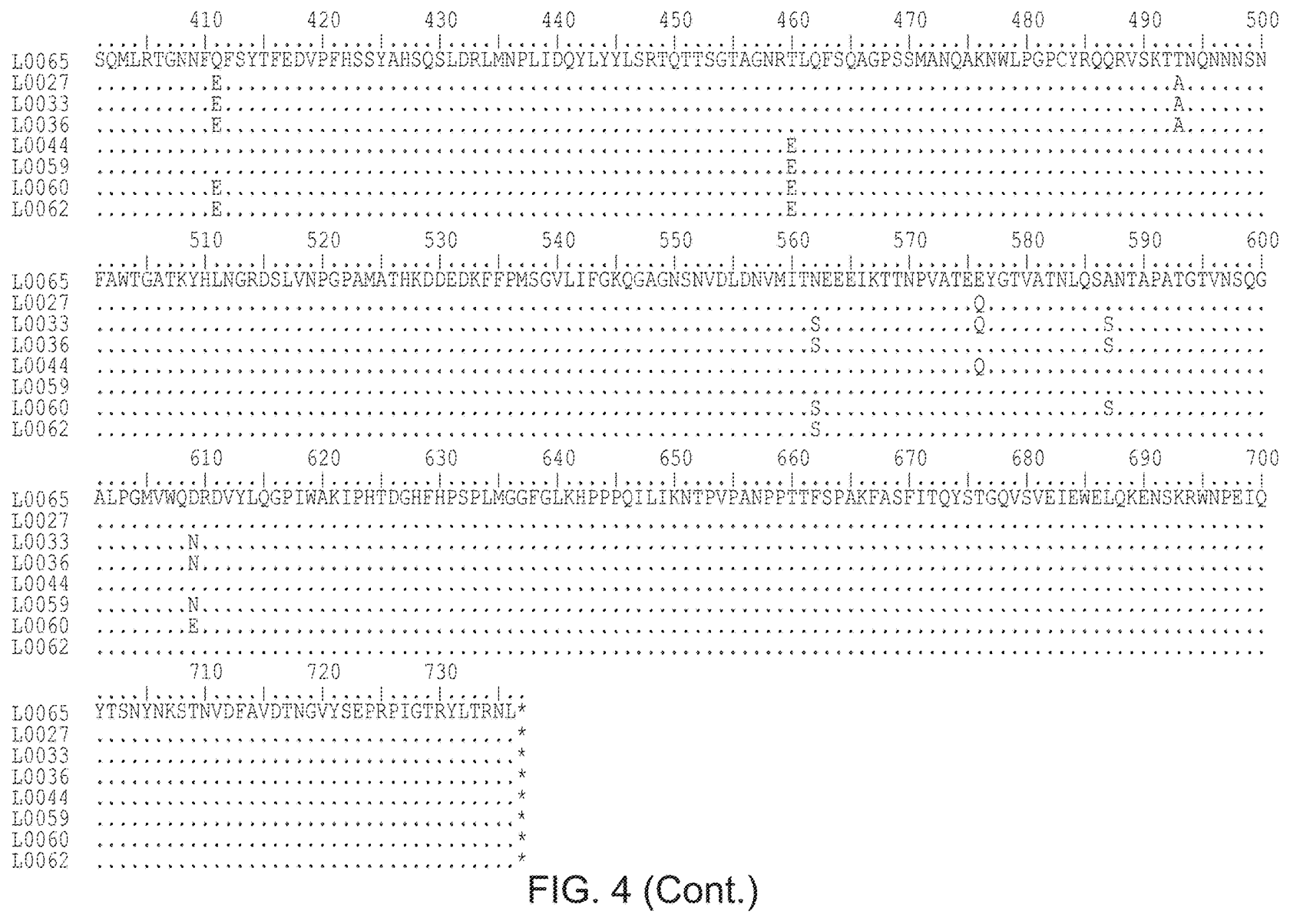
Figure 5A:
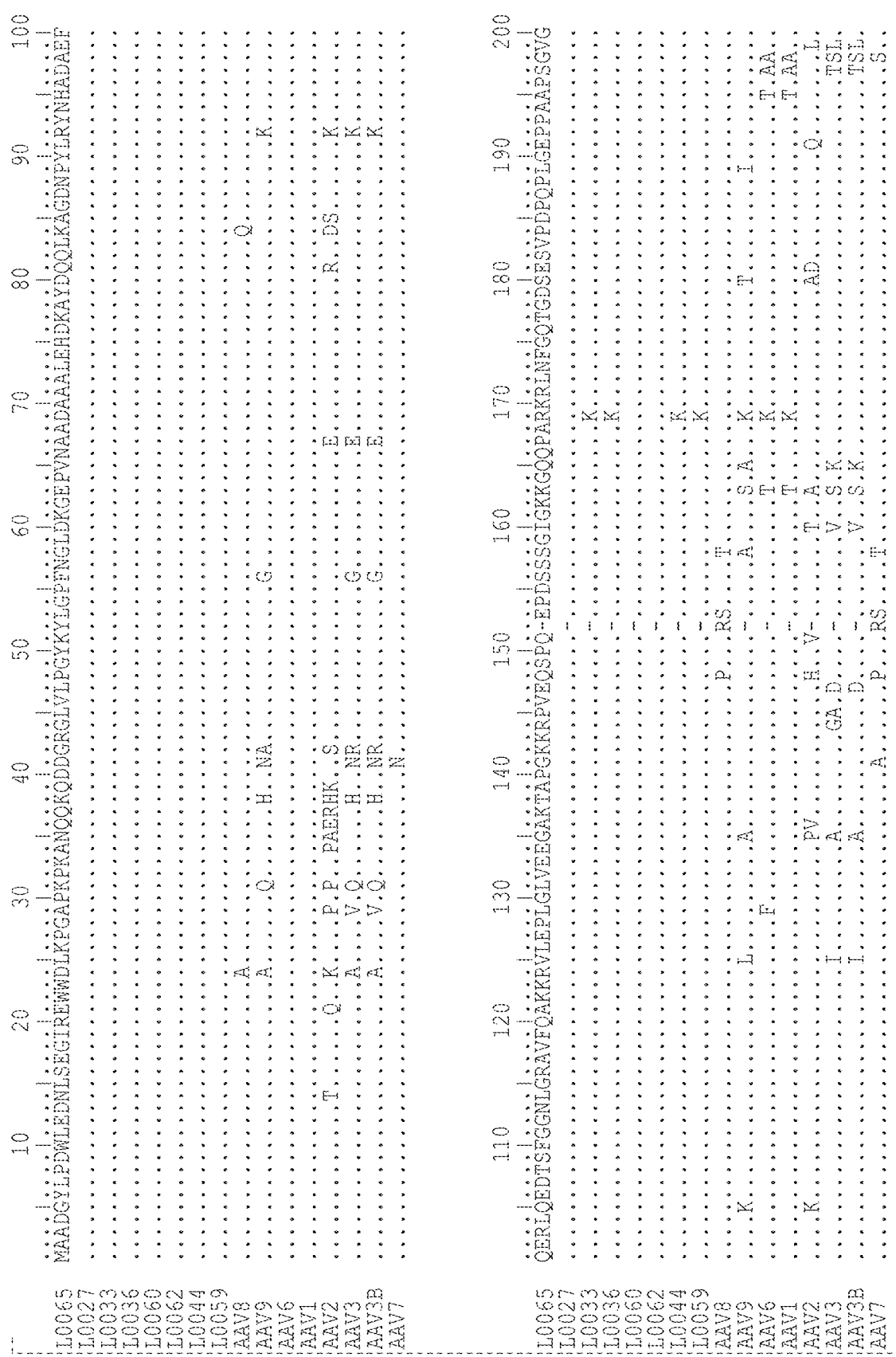
Figure 5B:
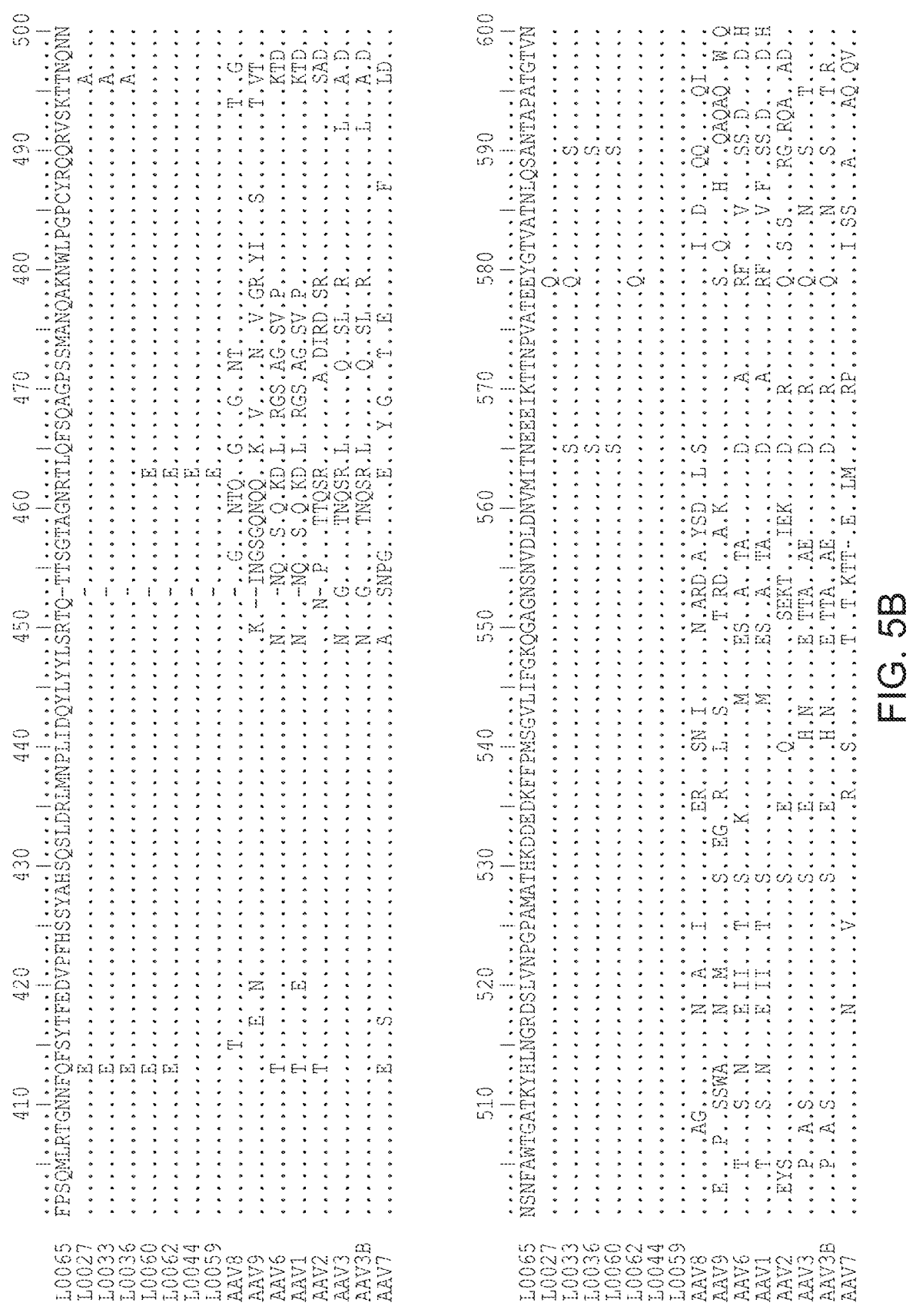
Figure 5B:
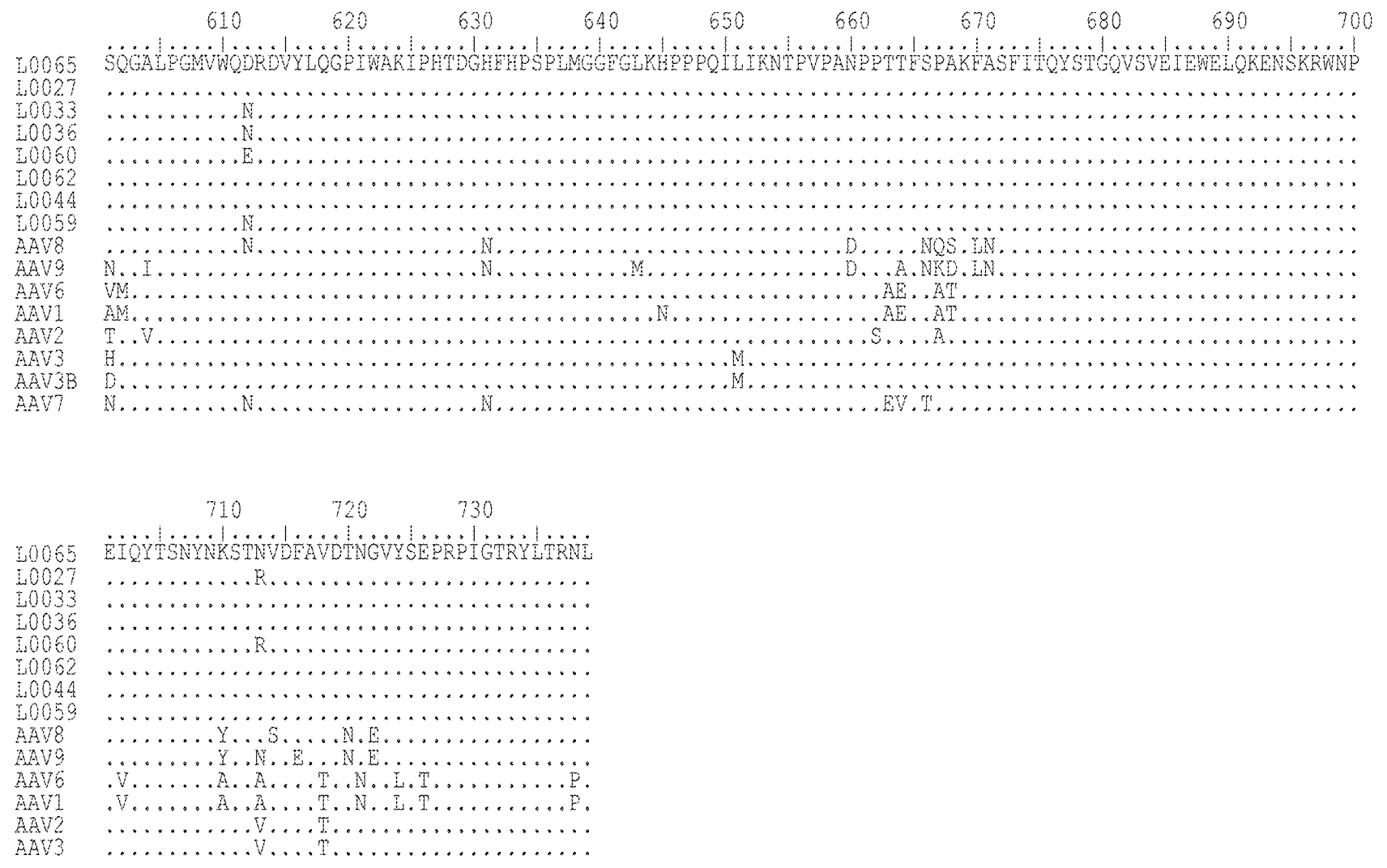

Representative alignments are shown in FIGS. 4A and 4B and FIGS. 5A and 5B. FIGS. 4A and 4B show an alignment of ancestral AAV VP1 capsid polypeptides, designated Anc80L65 (SEQ ID NO: 23), Anc80L27 (SEQ ID NO: 19), Anc80L33 (SEQ ID NO: 24), Anc80L36 (SEQ ID NO: 25), Anc80L44 (SEQ ID NO: 26), Anc80L59 (SEQ ID NO: 20), Anc80L60 (SEQ ID NO: 21), and Anc80L62 (SEQ ID NO: 22). The alignment shown in FIGS. 4A and 4B confirms the predicted variation at each of the 11 sites, and a single non-synonymous mutation at position 609E of Anc80L60 (SEQ ID NO: 21), which may be a cloning artifact. FIGS. 5A and 5B shows an alignment between ancestral AAV VP1 capsid polypeptides (Anc80L65 (SEQ ID NO: 23), Anc80L27 (SEQ ID NO: 19), Anc80L33 (SEQ ID NO: 24), Anc80L36 (SEQ ID NO: 25), Anc80L60 (SEQ ID NO: 21), Anc80L62 (SEQ ID NO: 22), Anc80L44 (SEQ ID NO: 26), and Anc80L59 (SEQ ID NO: 20)) and contemporary AAV VP1 capsid polypeptides (AAV8 (SEQ ID NO: 27), AAV9 (SEQ ID NO: 28), AAV6 (SEQ ID NO: 29), AAV1 (SEQ ID NO: 30), AAV2 (SEQ ID NO: 31), AAV3 (SEQ ID NO: 32), AAV3B (SEQ ID NO: 33), and AAV7 (SEQ ID NO: 34)). The alignment in FIGS. 5A and 5B shows that the ancestral AAV sequences have between about 85% and 91% sequence identity to contemporary AAV sequences.

Vectors containing nucleic acid molecules that encode polypeptides also are provided. Vectors, including expression vectors, are commercially available or can be produced by recombinant technology. A vector containing a nucleic acid molecule can have one or more elements for expression operably linked to such a nucleic acid molecule, and further can include sequences such as those encoding a selectable marker (e.g., an antibiotic resistance gene), and/or those that can be used in purification of a polypeptide (e.g., 6xHis tag). Elements for expression include nucleic acid sequences that direct and regulate expression of nucleic acid coding sequences. One example of an expression element is a promoter sequence. Expression elements also can include one or more of introns, enhancer sequences, response elements, or inducible elements that modulate expression of a nucleic acid molecule. Expression elements can be of bacterial, yeast, insect, mammalian, or viral origin and vectors can contain a combination of expression elements from different origins. As used herein, operably linked means that elements for expression are positioned in a vector relative to a coding sequence in such a way as to direct or regulate expression of the coding sequence.

A nucleic acid molecule, e.g., a nucleic acid molecule in a vector (e.g., an expression vector, a viral vector) can be introduced into a host cell. The term "host cell" refers not only to the particular cell(s) into which the nucleic acid molecule has been introduced, but also to the progeny or potential progeny of such a cell. Many suitable host cells are known to those skilled in the art; host cells can be prokaryotic cells (e.g., *E. coli*) or eukaryotic cells (e.g., yeast cells, insect cells, plant cells, mammalian cells). Representative host cells can include, without limitation, A549, WEHI, 3T3, 10T1/2, BHK, MDCK, COS 1, COS 7, BSC 1, BSC 40, BMT 10, VERO, WI38, HeLa, 293 cells, Saos, C2C12, L cells, HT1080, HepG2 and primary fibroblast, hepatocyte and myoblast cells derived from mammals including human, monkey, mouse, rat, rabbit, and hamster. Methods for introducing nucleic acid molecules into host cells are well known in the art and include, without limitation, calcium phosphate precipitation, electroporation, heat shock, lipofection, microinjection, and viral-mediated nucleic acid transfer (e.g., transduction).

With respect to polypeptides, "purified" refers to a polypeptide (i.e., a peptide or a polypeptide) that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is considered "purified," but further can be removed from the components used to synthesize the polypeptide (e.g., amino acid residues). With respect to nucleic acid molecules, "isolated" refers to a nucleic acid molecule that is separated from other nucleic acid molecules that are usually associated with it in the genome. In addition, an isolated nucleic acid molecule can include an engineered nucleic acid molecule such as a recombinant or a synthetic nucleic acid molecule.

Polypeptides can be obtained (e.g., purified) from natural sources (e.g., a biological sample) by known methods such as DEAE ion exchange, gel filtration, and/or hydroxyapatite chromatography. A purified polypeptide also can be obtained, for example, by expressing a nucleic acid molecule in an expression vector or by chemical synthesis. The extent of purity of a polypeptide can be measured using any appropriate method, e.g., column chromatography, polyacrylamide gel electrophoresis, or HPLC analysis. Similarly, nucleic acid molecules can be obtained (e.g., isolated) using routine methods such as, without limitation, recombinant nucleic acid technology (e.g., restriction enzyme digestion and ligation) or the polymerase chain reaction (PCR; see, for example, PCR Primer: A Laboratory Manual, Dieffenbach & Dveksler, Eds., Cold Spring Harbor Laboratory Press, 1995). In addition, isolated nucleic acid molecules can be chemically synthesized.

Methods of Using Ancestral Viruses or Portions Thereof

An ancestral virus or portion thereof as described herein, particularly those that exhibit reduced seroprevalence relative to contemporary viruses or portions thereof, can be used in a number of research and/or therapeutic applications. For example, an ancestral virus or portion thereof as described herein can be used in human or animal medicine for gene therapy (e.g., in a vector or vector system for gene transfer) or for vaccination (e.g., for antigen presentation). More specifically, an ancestral virus or portion thereof as described herein can be used for gene addition, gene augmentation, genetic delivery of a polypeptide therapeutic, genetic vaccination, gene silencing, genome editing, gene therapy, RNAi delivery, cDNA delivery, mRNA delivery, miRNA delivery, miRNA sponging, genetic immunization, optogenetic gene therapy, transgenesis, DNA vaccination, or DNA immunization.

A host cell can be transduced or infected with an ancestral virus or portion thereof in vitro (e.g., growing in culture) or in vivo (e.g., in a subject). Host cells that can be transduced or infected with an ancestral virus or portion thereof in vitro are described herein; host cells that can be transduced or infected with an ancestral virus or portion thereof in vivo include, without limitation, brain, liver, muscle, lung, eye (e.g., retina, retinal pigment epithelium), kidney, heart, gonads (e.g., testes, uterus, ovaries), skin, nasal passages, digestive system, pancreas, islet cells, neurons, lymphocytes, ear (e.g., inner ear), hair follicles, and/or glands (e.g., thyroid).

An ancestral virus or portion thereof as described herein can be modified to include a transgene (in cis or trans with other viral sequences). A transgene can be, for example, a reporter gene (e.g., beta-lactamase, beta-galactosidase (LacZ), alkaline phosphatase, thymidine kinase, green fluorescent polypeptide (GFP), chloramphenicol acetyltransferase (CAT), or luciferase, or fusion polypeptides that include an antigen tag domain such as hemagglutinin or Myc) or a therapeutic gene (e.g., genes encoding hormones or receptors thereof, growth factors or receptors thereof, differentiation factors or receptors thereof, immune system regulators (e.g., cytokines and interleukins) or receptors thereof, enzymes, RNAs (e.g., inhibitory RNAs or catalytic RNAs), or target antigens (e.g., oncogenic antigens, autoimmune antigens)).

The particular transgene will depend, at least in part, on the particular disease or deficiency being treated. Simply by way of example, gene transfer or gene therapy can be applied to the treatment of hemophilia, retinitis pigmentosa, cystic fibrosis, leber congenital amaurosis, lysosomal storage disorders, inborn errors of metabolism (e.g., inborn errors of amino acid metabolism including phenylketonuria, inborn errors of organic acid metabolism including propionic academia, inborn errors of fatty acid metabolism including medium-chain acyl-CoA dehydrogenase deficiency (MCAD)), cancer, achromatopsia, cone-rod dystrophies, macular degenerations (e.g., age-related macular degeneration), lipopolypeptide lipase deficiency, familial hypercholesterolemia, spinal muscular atrophy, Duchenne's muscular dystrophy, Alzheimer's disease, Parkinson's disease, obesity, inflammatory bowel disorder, diabetes, congestive heart failure, hypercholesterolemia, hearing loss, coronary heart disease, familial renal amyloidosis, Marfan's syndrome, fatal familial insomnia, Creutzfeldt-Jakob disease, sickle-cell disease, Huntington's disease, fronto-temporal lobar degeneration, Usher syndrome, lactose intolerance, lipid storage disorders (e.g., Niemann-Pick disease, type C), Batten disease, choroideremia, glycogen storage disease type II (Pompe disease), ataxia telangiectasia (Louis-Bar syndrome), congenital hypothyroidism, severe combined immunodeficiency (SCID), and/or amyotrophic lateral sclerosis (ALS).

A transgene also can be, for example, an immunogen that is useful for immunizing a subject (e.g., a human, an animal (e.g., a companion animal, a farm animal, an endangered animal). For example, immunogens can be obtained from an organism (e.g., a pathogenic organism) or an immunogenic portion or component thereof (e.g., a toxin polypeptide or a by-product thereof). By way of example, pathogenic organisms from which immunogenic polypeptides can be obtained include viruses (e.g., picornavirus, enteroviruses, orthomyxovirus, reovirus, retrovirus), prokaryotes (e.g., *Pneumococci, Staphylococci, Listeria, Pseudomonas*), and eukaryotes (e.g., amebiasis, malaria, leishmaniasis, nematodes). It would be understood that the methods described herein and compositions produced by such methods are not to be limited by any particular transgene.

An ancestral virus or portion thereof, usually suspended in a physiologically compatible carrier, can be administered to a subject (e.g., a human or non-human mammal).

Suitable carriers include saline, which may be formulated with a variety of buffering solutions (e.g., phosphate buffered saline), lactose, sucrose, calcium phosphate, gelatin, dextran, agar, pectin, and water. The ancestral virus or portion thereof is administered in sufficient amounts to transduce or infect the cells and to provide sufficient levels of gene transfer and expression to provide a therapeutic benefit without undue adverse effects. Conventional and pharmaceutically acceptable routes of administration include, but are not limited to, direct delivery to an organ such as, for example, the liver or lung, orally, intranasally, intratracheally, by inhalation, intravenously, intramuscularly, intraocularly, subcutaneously, intradermally, transmucosally, or by other routes of administration. Routes of administration can be combined, if desired.

The dose of the ancestral virus or portion thereof administered to a subject will depend primarily on factors such as the condition being treated, and the age, weight, and health of the subject. For example, a therapeutically effective dosage of an ancestral virus or portion thereof to be administered to a human subject generally is in the range of from about 0.1 ml to about 10 ml of a solution containing concentrations of from about $1 \times 10^1$ to $1 \times 10^{12}$ genome copies (GCs) of ancestral viruses (e.g., about $1 \times 10^3$ to $1 \times 10^9$ GCs).

Transduction and/or expression of a transgene can be monitored at various time points following administration by DNA, RNA, or protein assays. In some instances, the levels of expression of the transgene can be monitored to determine the frequency and/or amount of dosage. Dosage regimens similar to those described for therapeutic purposes also may be utilized for immunization.

The methods described herein also can be used to model forward evolution, so as to modify or ablate one or more immunogenic domains of a virus or portion thereof.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Computational Prediction of Ancestral Sequences

A set of 75 different amino acid sequences of AAV capsids was obtained from a number of public databases including GenBank, and the sequences were aligned using the PRANK-MSA algorithm, version 121002, with the option "–F".

ProtTest3 (see, for example, Darriba et al., 2011, Bioinformatics, 27(8):1164-5; available at darwin.uvigo.es/software/prottest3 on the World Wide Web) was used to evaluate different models of polypeptide evolution (e.g., those included in ProTest3, namely, JTT, LG, WAG, VT, CpRev, RtRev, Dayhoff, DCMut, FLU, Blosum62, VT, HIVb, MtArt, MtMam) under different conditions (e.g., those included in ProTest3, namely, "+I", "+F", "+G", and combinations thereof). The JTT model (Jones et al., 1992, Comp. Appl. Biosci., 8:275-82) with +G and +F (Yang, 1993, Mol. Biol. Evol., 10:1396-1401; and Cao et al., 1994, J. Mol. Evol., 39:519-27) was selected based on its Aikake Information Criterion (AIC; Hirotugu, 1974, IEEE Transactions on Automatic Control, 19:716-23) score as implemented in ProTest3.

A phylogeny of AAV evolution was constructed using PhyML (Guindon and Gascuel, 2003, Systematic Biology, 52:696-704)). See FIG. 3. The tree was generated using the JTT+F substitution model with 4 discrete substitution categories and an estimated Gamma shape parameter. The resultant trees were improved via Nearest Neighbor Interchange (NNI) and Subtree Pruning and Re-Grafting (SPR), and assessed for significance via bootstrap and approximate likelihood-ratio test (aLRT; Anisimova and Gascuel, 2006, Systematic Biology, 55:539-52)) using the "SH-Like" variant.

The phylogenic tree constructed above was then used to estimate the ancestral states of the AAV capsid at every node interior to the phylogeny. The ancestral capsid sequences were reconstructed using maximum likelihood principles through the Phylogenetic Analysis by Maximum Likelihood (PAML) software (Yang, 1997, Comp. Applic. BioSci., 13:555-6; available at abacus.gene.ucl.ac.uk/software/paml.html on the World Wide Web) wrapped in Lazarus (Sourceforge at sf.net). More specifically, the Lazarus/PAML reconstruction was set to generate an amino acid reconstruction using the JTT+F substitution model using 4 gamma-distributed categories. AAV5 was used as an outgroup. Finally, the "I" option was added to place indels (i.e., coded binarily and placed via Maximum Parsimony using Fitch's algorithm) after the PAML reconstruction was done.

Because the reconstruction was done in a maximum-likelihood fashion, the likelihood that any residue was in a given position at a given node can be calculated. To do this, an additional script was written to identify all positions along the sequence with a calculated posterior probability beneath a certain threshold. A threshold of 0.3 was selected, meaning that any amino acid with a calculated posterior probability of greater than 0.3 was included in the synthesis of the library. These residues were selected to be variants of interest in the library.

To finalize the sequence, an additional utility had to be coded to select codons. A script was written to derive codons similar to those of another AAV sequence (AVVRh10, which has about 92% sequence identity to the Anc80 scaffold sequence) and apply a novel algorithm to substitute codons where there were sequence mismatches based on a codon-substitution matrix. The novel algorithm is shown below:

Given: amino acid sequence, Pt, with corresponding nucleotide sequence, Nt, where Nt codes for Pt; and protein sequence, Pi, where Pi exhibits strong homology to Pt.

Align Pi with Pt using Needleman-Wunsch using the Blosum62 table for scoring. Generate a new nucleotide sequence, Ni, by stepping through the protein alignment, using the corresponding codon from Nt,
where the amino acid in Pt exactly matches that in Pi, the "best scoring" codon from the Codon-PAM matrix (Schneider et al., 2005, BMC Bioinform., 6:134) where there is a substitution, a gap where there exists a gap in Pi aligned against an amino-acid in Pt, and the most frequently occurring nucleotide in the Nt (coding for a given amino acid) where there exists an amino-acid in Pi aligned against a gap in Pt.

In addition, two single nucleotide changes were made to ablate transcription of assembly-activating protein (AAP), which is encoded out of frame within the AAV capsid gene in the wild type AAV. Since the coding of AAP (contemporary or ancestral) was not a part of this reconstruction, the expression of AAP was ablated by making a synonymous mutation in the cap sequence, and the AAP sequence was provided in trans during viral production.

Example 2—Expression of Ancestral AAV VP1 Sequences

Experiments were performed to determine whether predicted ancestral AAV capsid sequences can be used to make viral vectors.

A number of the predicted ancestral AAV capsid sequences were cloned. The library of ancestral capsids was transferred to a rep-cap expression plasmid to enable viral particle formation in transient transfection. To maintain appropriate expression levels and splicing of VP1, VP2, and VP3, library cap genes were cloned by cutting HindIII, located 5' of cap in the rep coding sequence, and SpeI, which was engineered between the cap stop codon and the polyadenylation signal. Consequently, to clone the ancestral capsids into a more conventional "REP/CAP" construct, the passaging-plasmid was digested with HindIII and SpeI, gel purified, and ligated into a similarly digested rep/cap plasmid.

Figure 6:
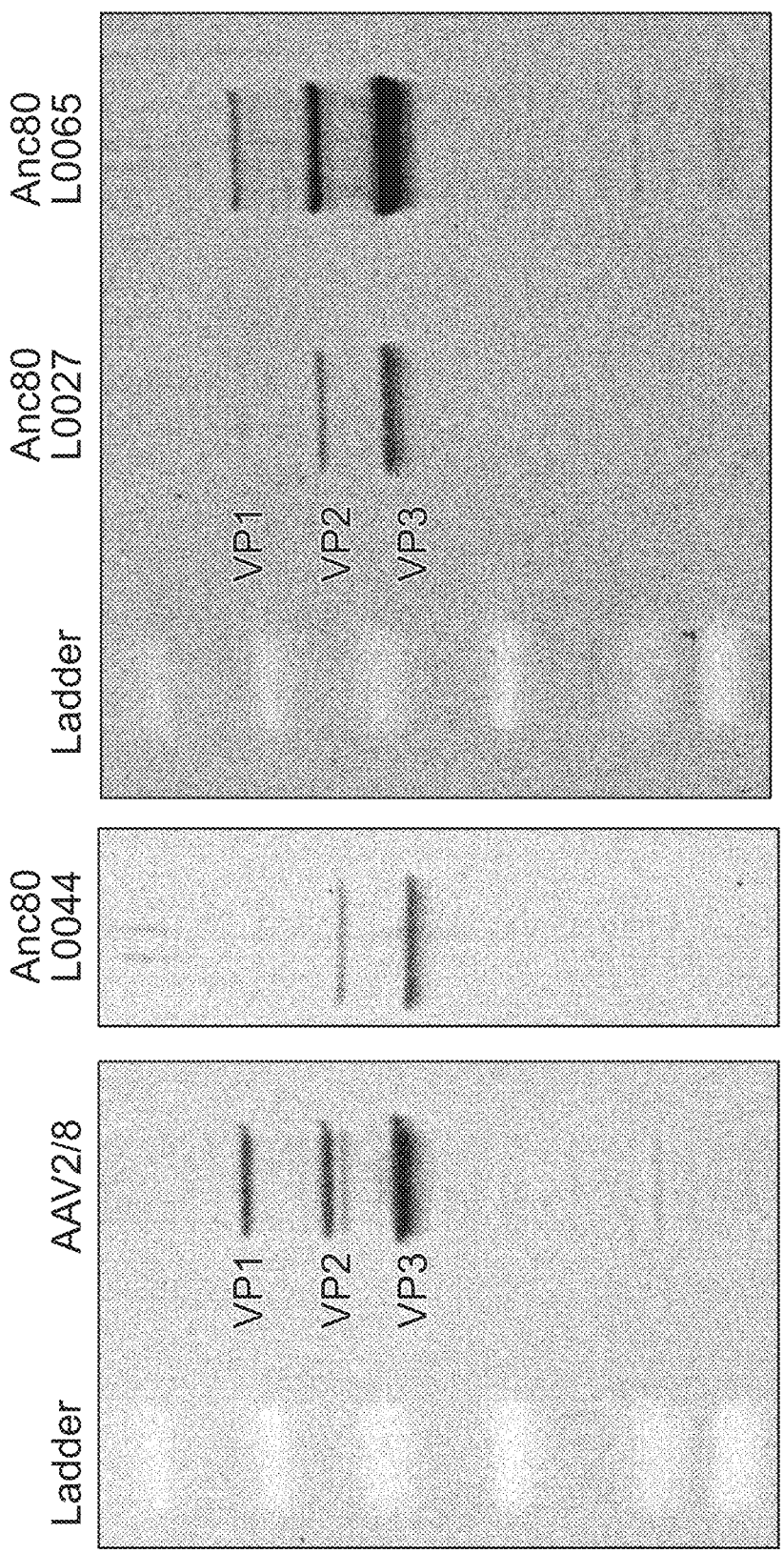

The expressed polypeptides were resolved on a 10% SDS gel. As shown in FIG. 6, the capsid polypeptides were appropriately expressed and spliced into VP1, VP2, and VP3 from a number of ancestral AAV sequences (Anc80L44, Anc80L27, and Anc80L65) as well as from a contemporary AAV sequence, AAV2/8.

Example 3—Viral Titration

AAV was produced in HEK293 cells via transient co-transfection of plasmids encoding all elements required for viral particle assembly. Briefly, HEK293 cells were grown to 90% confluency and transfected with (a) the viral genome plasmid encoding the luciferase transgene (expressed by the CMV promoter) flanked by AAV2 ITRs, (b) the AAV packaging plasmid encoding AAV2 rep and the synthesized capsid proteins disclosed herein, (c) AAV2-AAP expressing capsid, and (d) adenoviral helper genes needed for AAV packaging and assembly. Cells were incubated at 37° C. for 2 days, and cells and media were harvested and collected.

The cell-media suspension was lysed by 3 consecutive freeze-thaw cycles. Next, the lysate was cleared by centrifugation and treated with an enzyme under conditions to perform exhaustive DNA digestion, here BENZONASE™, to digest any DNA present outside of the virus particle. The AAV preparation was diluted to fall within the linear measurement range of a control DNA template, in this case linearized plasmid with identical TAQMAN™ primer and probe binding sequence as compared to the vector genome. TAQMAN™ PCR was performed with primers and probe annealing to the viral vector genome of choice. Titer was calculated based on the TAQMAN™ measurement in genome copies (GC) per milliliter (ml) as shown in Table 2 below.

TABLE 2

| Titers (GC/ml) | Small scale #1 | Small scale #2 |
|---|---|---|
| AAV2/2 | $1.12 \times 10^9$ | $1.99 \times 10^9$ |
| AAV2/8 | $4.17 \times 10^{10}$ | $5.91 \times 10^{10}$ |
| Anc80L27 | $8.01 \times 10^8$ | $1.74 \times 10^9$ |
| Anc80L44 | $1.52 \times 10^9$ | $1.43 \times 10^9$ |
| Anc80L65 | $1.42 \times 10^9$ | $2.05 \times 10^9$ |
| No capsid control | $5.23 \times 10^5$ | $7.25 \times 10^5$ |

Small scale vector production results on ancestrally reconstructed AAV capsid particles demonstrated yields that were similar to AAV2, but reduced relative to AAV8, both of which are vector preparations based on contemporary AAVs.

Example 4 In Vitro Viral Transduction

In vitro viral transductions were performed to evaluate the ability of viruses containing the predicted ancestral AAV sequences to infect cells.

Following high throughput vector production using the Anc80 library of sequences, HEK293 cells were transduced with each viral vector. In addition to an Anc80 sequence, each viral vector contained a luciferase transgene. Luciferase was measured by quantification of bioluminescence in a 96 well plate reader following addition of luciferin substrate to the transduced cells or cell lysate. Following quantification, a heat map of luciferase expression in four concatenated 96-well plates was produced (excluding a column of controls in each plate). Due to the large number of insertions, deletions, and transitions associated with the process of high throughput vector production, many of the vectors were non-functional. For purposes herein, only viruses that were functional in this assay (i.e., able to transduce HEK293 cells and express the transgene) were evaluated further.

Figure 7:
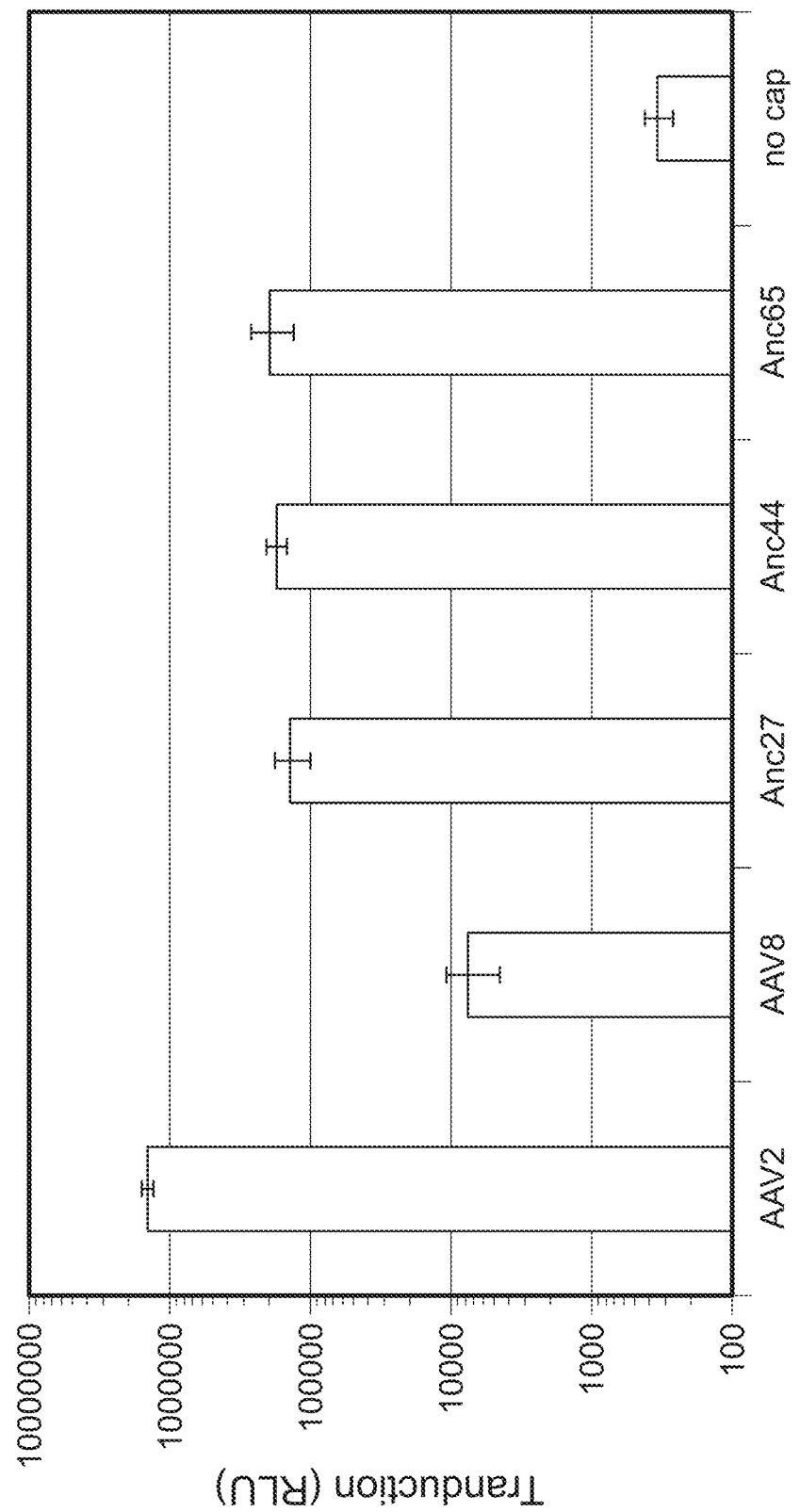

HEK293 cells were transduced, at equal multiplicity of infection (MOI) of $1 \times 10^4$ genome copies (GC) per cell, with two contemporary AAV vectors (AAV2/2 and AAV2/8) and three predicted ancestral AAV vectors (Anc80L27, Anc80L44, and Anc80L65). Each vector contained either a luciferase-encoding transgene or an eGFP-encoding transgene. Cells were imaged 60 hours later using the GFP channel of an AMG EvosFl Optical Microscope. FIG. 7 shows the luciferase expression following the in vitro transduction. Each of the ancestral AAV viruses demonstrated efficient transduction of HEK293 cells.

Example 5—In Vivo Retinal Transduction

Retinal transductions were performed to determine whether or not the ancestral AAV vectors are able to target murine retinal cells in vivo.

Murine eyes were transduced with $2 \times 10^8$ genome copies (GC) of three different ancestral AAVs (Anc80L27, Anc80L44, and Anc80L65) and a contemporary AAV (AAV2/8), all of which included an eGFP-encoding transgene. For transductions, each AAV vector was surgically delivered below the retina by generating a space between the photoreceptor and retinal pigment epithelium layer through delivery of a vector bolus with an injection device. The vector bolus was left in the sub-retinal space and the sub-retinal detachment resolved over time. GFP expression was monitored non-invasively by fundus photography of the retina of the animal following pupil dilation with TROPI-CAMIDE™. All of the presented retinas demonstrated varying degrees of successful targeting of ancestral AAVs to the retina.

Retinal histology also was performed and visualized under fluorescent microscopy to identify the transduced cell type(s). Histology was performed on a murine retina transduced with the Anc80L65 ancestral AAV vector as described above. Anc80L65-mediated eGFP expression was evident in the outer nuclear layer (ONL), the inner segments (IS), and the retinal pigment epithelium (RPE), indicating that the ancestral Anc80L65 vector targets murine photoreceptors and retinal pigment epithelial cells.

Example 6—Neutralizing Antibody Assay

Neutralizing antibody assays were performed to evaluate whether or not an ancestral AAV virus is more resistant to antibody-neutralization than a contemporary AAV virus. Neutralizing antibody assays measure the antibody concentration (or the titer at which an experimental sample contains an antibody concentration) that neutralizes an infection by 50% or more as compared to a control in the absence of the antibody.

Serum samples or IVIG stock solution (200 mg/ml) were serially diluted by 2-fold, and undiluted and diluted samples were co-incubated with an ancestral AAV virus, Anc80L65, and a contemporary AAV virus, AAV2/8, at a MOI of $10^4$ for about 30 minutes at 37° C. Each virus included a luciferase transgene. The admixed vector and an antibody sample then were transduced into HEK293 cells. For these experiments, the antibody sample used was intravenous immunoglobulin (IVIG), pooled IgGs extracted from the plasma of over one thousand blood donors (sold commercially, for example, as GAMMAGARD™ (Baxter Healthcare; Deerfield, Ill.) or GAMUNEX™ (Grifols; Los Angeles, Calif.)). 48 hours following initiation of transduction, cells were assayed by bioluminescence to detect luciferase. Neutralizing antibody titer was determined by identifying the dilution of sample for which 50% or more neutralization (transduction of sample/transduction of control virus in absence of sample) was reached.

Example 7—Characterization of Anc80

Based on the methods described herein, the most probable Anc80 sequence (as determined through posterior probability) was obtained and designated Anc80L1 (SEQ ID NO:35 shows the nucleic acid sequence of the Anc80L1 capsid and SEQ ID NO:36 shows the amino acid sequence of the Anc80L1 VP1 polypeptide). The Anc80 probabilistic library also was synthesized using the sequences described herein by a commercial company and sub-cloned into expression vectors.

The Anc80 library was clonally evaluated for vector yield and infectivity in combined assays. Out of this screening, Anc80L65 (SEQ ID NO:23), as well as several other variants, were further characterized.

The Anc80 library and Anc80L65 were compared in terms of sequence difference (FIG. 8; % up from diagonal, # of amino acid differences below). Using NCBI-BLAST, the closest publically available sequence to Anc80L65 is rh10 (GenBank Accession No. AAO88201.1).

FIG. 9 shows that Anc80L65 produced vector yields equivalent to AAV2 (Panel A), generated virus particles under Transmission Electroscopy (TEM) (Panel B), and biochemically produced the AAV cap and the VP1, 2 and 3 proteins based on SDS page under denaturing conditions (Panel C) and Western Blotting using the AAV capsid antibody, B1 (Panel D). These experiments are described in more detail in the following paragraphs.

Figure 9C:
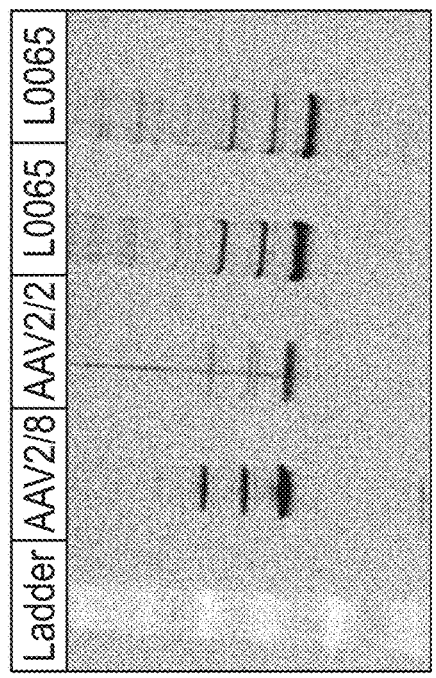
Figure 9D:
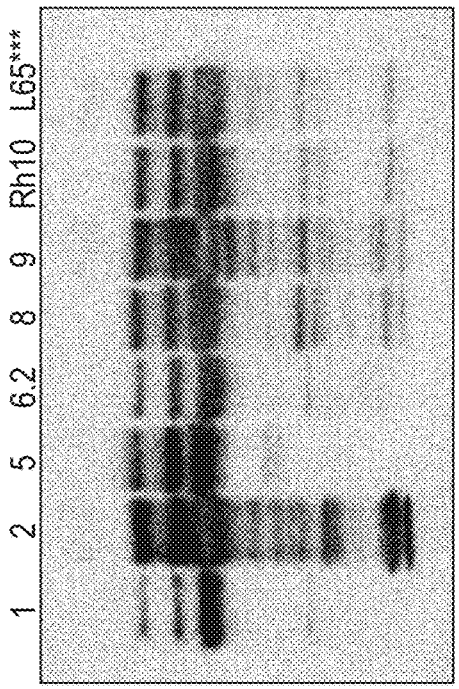
Figure 9A:
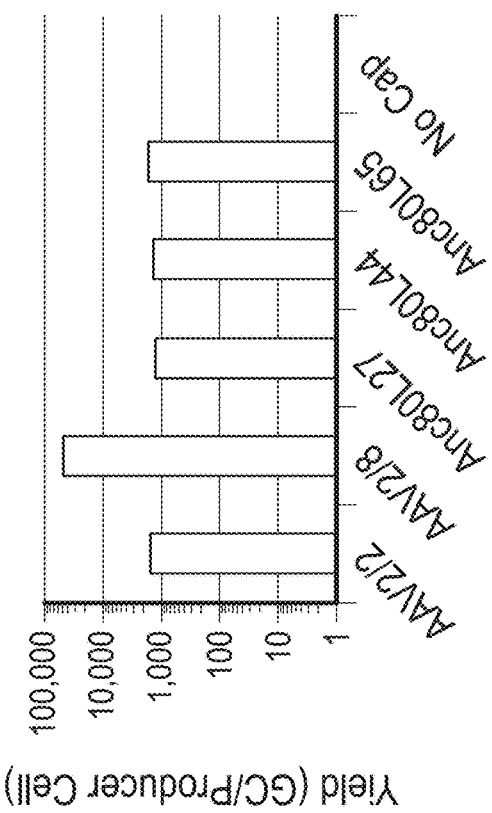

Briefly, AAV2/8, AAV2/2, AAV2/Anc80L27, AAV2/Anc80L44, and AAV2/Anc80L65 vectors were produced in small scale containing a reporter construct comprised of eGFP and firefly luciferase under a CMV promoter were produced in small scale. Titers of these small scale preparations of viruses were then obtained via qPCR. Based on these experiments, Anc80L27, Anc80L44, and Anc80L65 vectors were found to produce viral levels comparable to that of AAV2 (FIG. 9A).

Figure 9B:
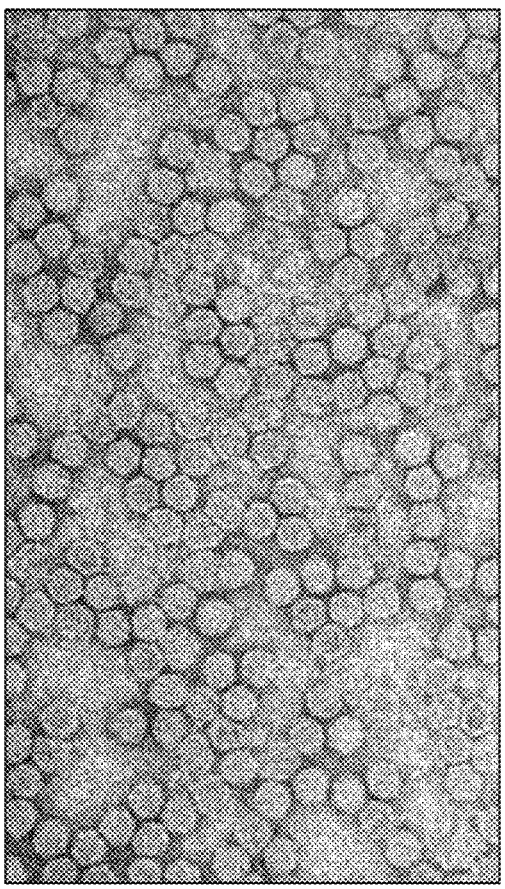

To confirm that the Anc80L65 capsid proteins assembled into intact virus-like particles of the proper size and conformation, micrographs were obtained using transmission electron microscopy (TEM). A large scale, purified preparation of Anc80-L065 was loaded onto polyvinyl formal (FORMVAR®) coated copper grids and was then stained with uranyl acetate. Micrographs revealed intact, hexagonal particles with diameters between 20 and 25 nm (FIG. 9B).

In order to determine whether the synthetic ancestral capsid genes were properly processed (i.e. spliced and expressed), large-scale purified preparations of AAV2/8, AAV2/2, and AAV2/Anc80L65 vectors were loaded onto an SDS-PAGE gel (1E10 GC/well) under denaturing conditions. Bands representing viral capsid proteins VP1, VP2, and VP3 were clearly present for each vector preparation (FIG. 9C). Western blotting with the AAV capsid antibody B1 further confirmed that these bands represented the predicted proteins (FIG. 9D).

In addition, FIG. 10 shows that Anc80L65 infected mammalian tissue and cells in vitro on HEK293 cells at MOI 10E4 GC/cell using GFP as readout (Panel A) or luciferase (Panel B) versus AAV2 and/or AAV8 controls. Anc80L65 also was efficient at targeting liver following an IV injection of the indicated AAV encoding a nuclear LacZ transgene (top row, Panel C), following direct intramuscular (IM) injection of the indicated AAV encoding GFP (middle row, Panel C), and following subretinal injection with the indicated AAV encoding GFP (bottom row, Panel C). These experiments are described in more detail in the following paragraphs.

To obtain a relative measure of the infectivity of ancestral virions, crude preparations of AAV2/2, AAV2/8, AAV2/Anc80L65, AAV2/Anc80L44, AAV2/Anc80L27, AAV2/Anc80L121, AAV2/Anc80L122, AAV2/Anc80L123, AAV2/Anc80L124, and AAV2/Anc80L125 containing a bi-cistronic reporter construct that includes an eGFP and firefly luciferase sequences under control of a CMV promoter were produced. 96-well plates confluent with HEK293 cells were then subjected to transduction with each vector at an MOI of 1E4 GC/cell (titers obtained via qPCR as above). 48 hours later, fluorescent microscopy confirmed the presence of GFP in transduced cells (FIG. 10A). Cells were then assayed for the presence of luciferase (FIG. 10B), which determined that expression of luciferase in cells transduced with Anc80-derived vectors was in-between that of cells transduced with AAV8 (lower level of transduction) and AAV2 (higher level of transduction).

To assess the relative efficiency of gene transfer in an in vivo context, purified high-titer preparations of AAV2/2, AAV2/8, and AAV2/Anc80L65 were obtained. 3.9E10 GC of each vector, encapsidating a transgene encoding nuclear LacZ under control of a TBG promoter, were injected into C57BL/6 mice (3 mice per condition) via IP injection following general anesthetization. 28 days post-injection, mice were sacrificed and tissues were collected. Livers were sectioned via standard histological techniques and stained for beta-galactosidase. Sections were then imaged under a microscope and representative images are shown in FIG. 10C, top row.

Vectors of the same serotypes were then obtained containing a bicistronic transgene encoding eGFP and hA1AT under control of a pCASI promoter. To assess the ability of Anc80L65 to transduce murine skeletal muscle, 1E10 GC of each vector was injected into skeletal muscle of C57BL/6 mice (5 mice per condition) following general anesthetization. 28 days post-injection, mice were sacrificed, tissues were cryosectioned, and the presence of eGFP was assessed using fluorescent confocal microscopy (blue is DAPI, green is eGFP). Representative images are shown in FIG. 10C, middle row. These experiments demonstrated that Anc80L65 vectors were capable of transducing murine skeletal muscle via intramuscular injection.

Vectors of the same serotypes were obtained, this time encapsidating constructs encoding only an eGFP transgene under control of a CMV promoter. 2E9 particles were injected sub-retinally into C57BL/6 mice following general anesthetization. 28 days post-injection, mice were sacrificed and the eyes were collected, cryosectioned, and the presence of eGFP was assessed using fluorescent confocal microscopy (blue is DAPI, green is eGFP). Representative images are shown in FIG. 10C, bottom row. These experiments demonstrate that Anc80L65 vectors are able to transduce murine retina at a level that is comparable to AAV8 vectors.

Briefly, purified, high titer preparations of AAV2/8, AAV2/2, AAV2/rh32.33, and AAV2/Anc80L65 viral vectors encapsidating a bicistronic transgene that includes eGFP and firefly luciferase under control of a CMV promoter were obtained. These vectors were then either incubated with two-fold serial dilutions of IVIG (10 mg, 5 mg, 2.5 mg, etc.) or incubated without IVIG (1E9 GC per condition). Following incubation, vectors were used to transduce HEK293 cells at an MOI of 1E4 per well (one dilution per well).

Example 8—Generation of Additional Ancestral AAV Capsids

The most probable ancestral AAV capsid sequences (as determined through posterior probability) were then synthesized through a commercial lab (Gen9) and provided as linear dsDNA. These amino acid sequences were then compared to those of extant AAVs in order to ascertain the degree to which they differ (FIG. 11). Each ancestral VP1 protein differs from those of selected representative extant AAVs by between 3.6% and 9.3% (FIG. 11A), while the ancestral VP3 proteins differ by between 4.2 and 9.4% (FIG. 11B). These capsids were each subcloned into AAV production plasmids (pAAVector2/Empty) via restriction enzyme digestion (HindIII & SpeI) and T4 ligation. These clones were confirmed via restriction digestion and Sanger sequencing, and medium scale preparations of plasmid DNA were then produced.

Figure 12:
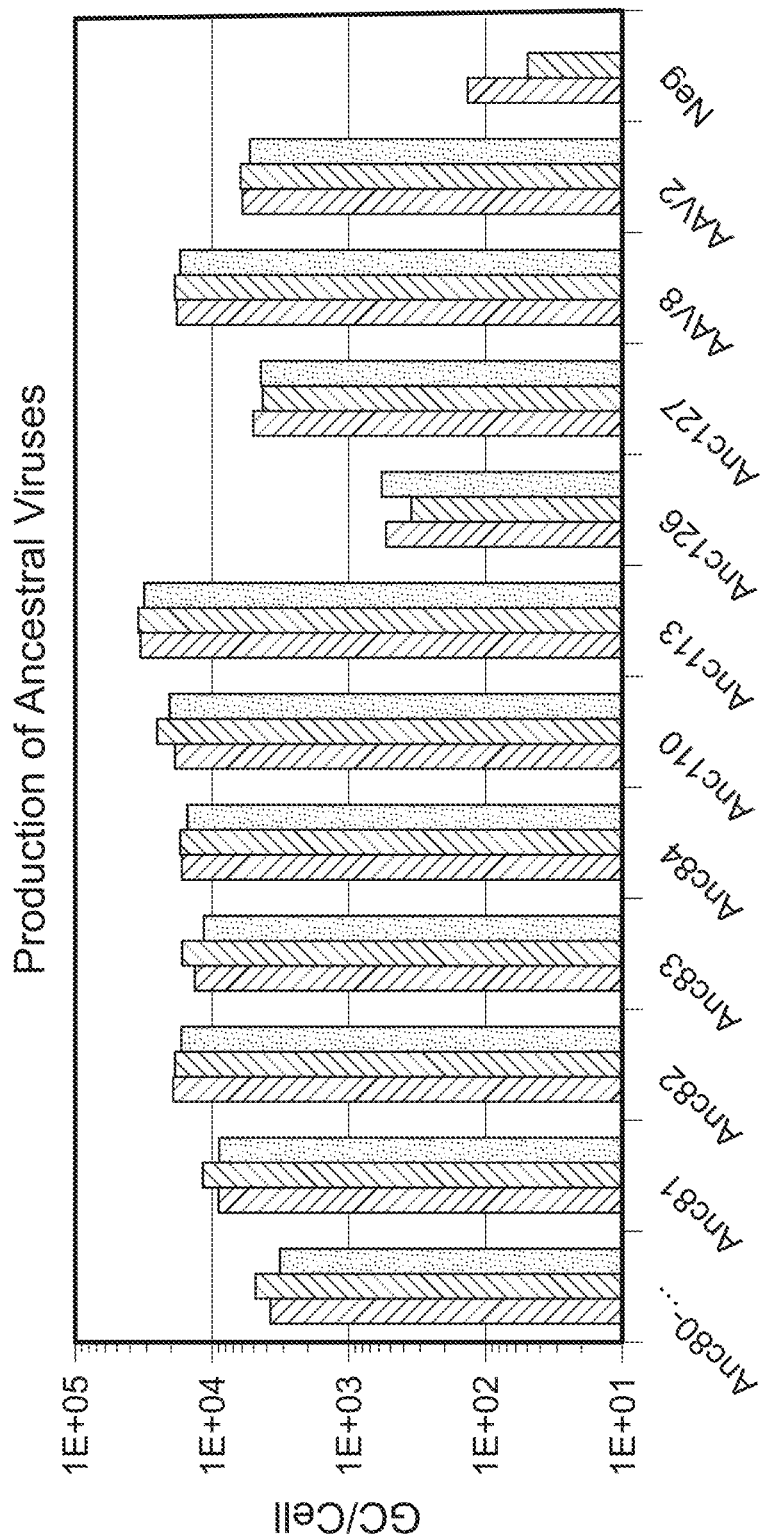
FIG. 12 is a graph that demonstrates that AAV vectors were produced in triplicate in small scale (6-well dishes). Crude viruses were assessed via qPCR to determine the absolute production of each vector.

Each of these plasmids were then used to produce AAV vectors containing a reporter gene encoding both eGFP and firefly luciferase. These vectors were produced in triplicate in small scale as previously described. Crude preparations of the virus were then titered via qPCR and were found to produce between 2.71% and 183.1% viral particles relative to AAV8 (FIGS. 12 and 13). These titers were then used to set up a titer controlled experiment to assess relative infectivity. Anc126 was not titer controlled due to its significantly depressed production, and consequently, the data regarding the infectivity of Anc126 cannot be accurately compared to the infectivity of the other viruses in the experiment. The other vectors were used to transduce HEK293 cells at a multiplicity of infection (MOI) of 1.9E3 GC/cell.

Figure 14:
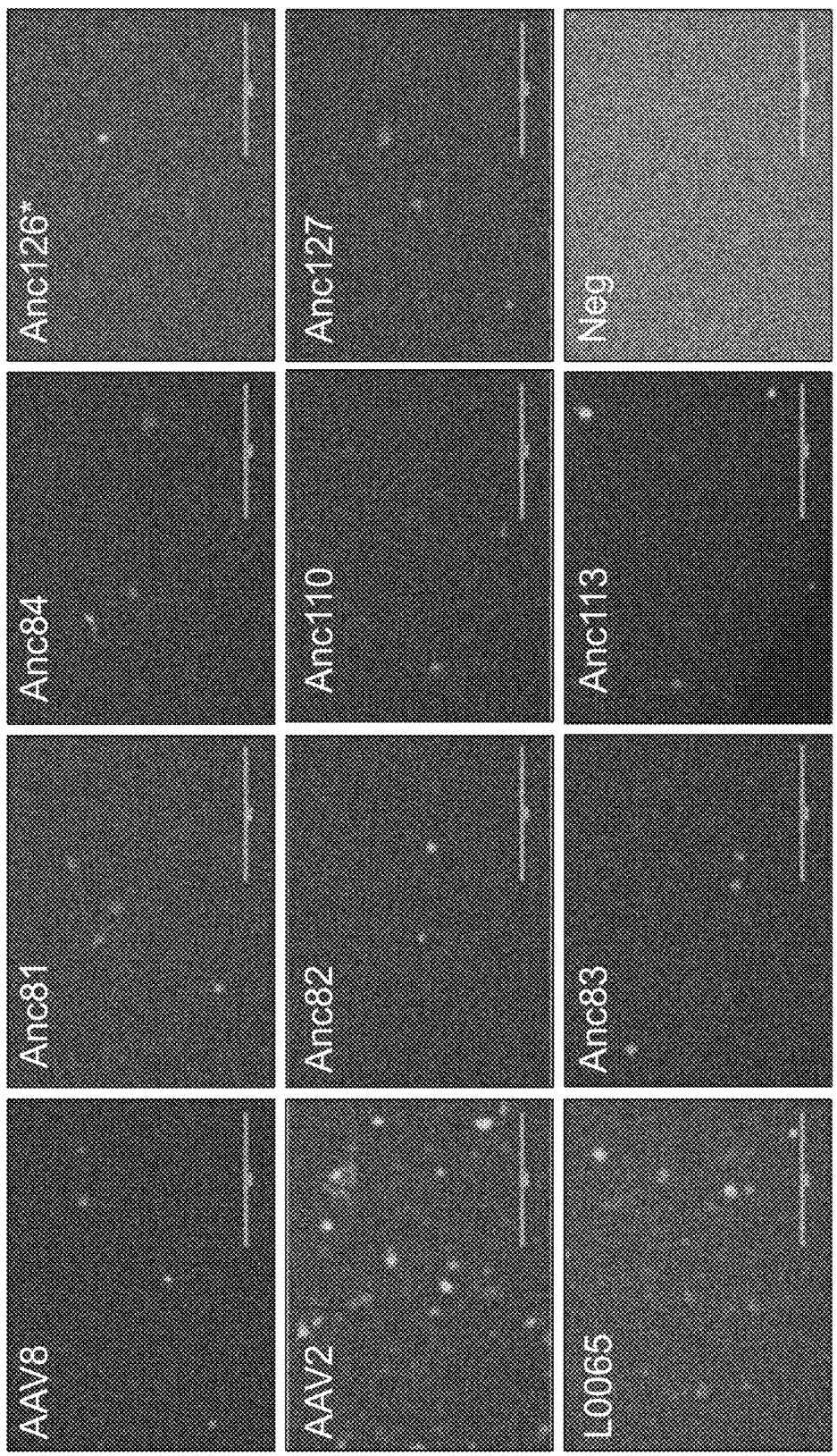
FIG. 14 are photographs that show the results of experiments in which 1.9E3 GC/cell of each vector was added to HEK293 cells (except for Anc126, in which case MOIs of 2.5E2-3.1E2 GC/cell were achieved). Sixty hours later, infectivity was assessed using fluorescence microscopy.
Figure 15:
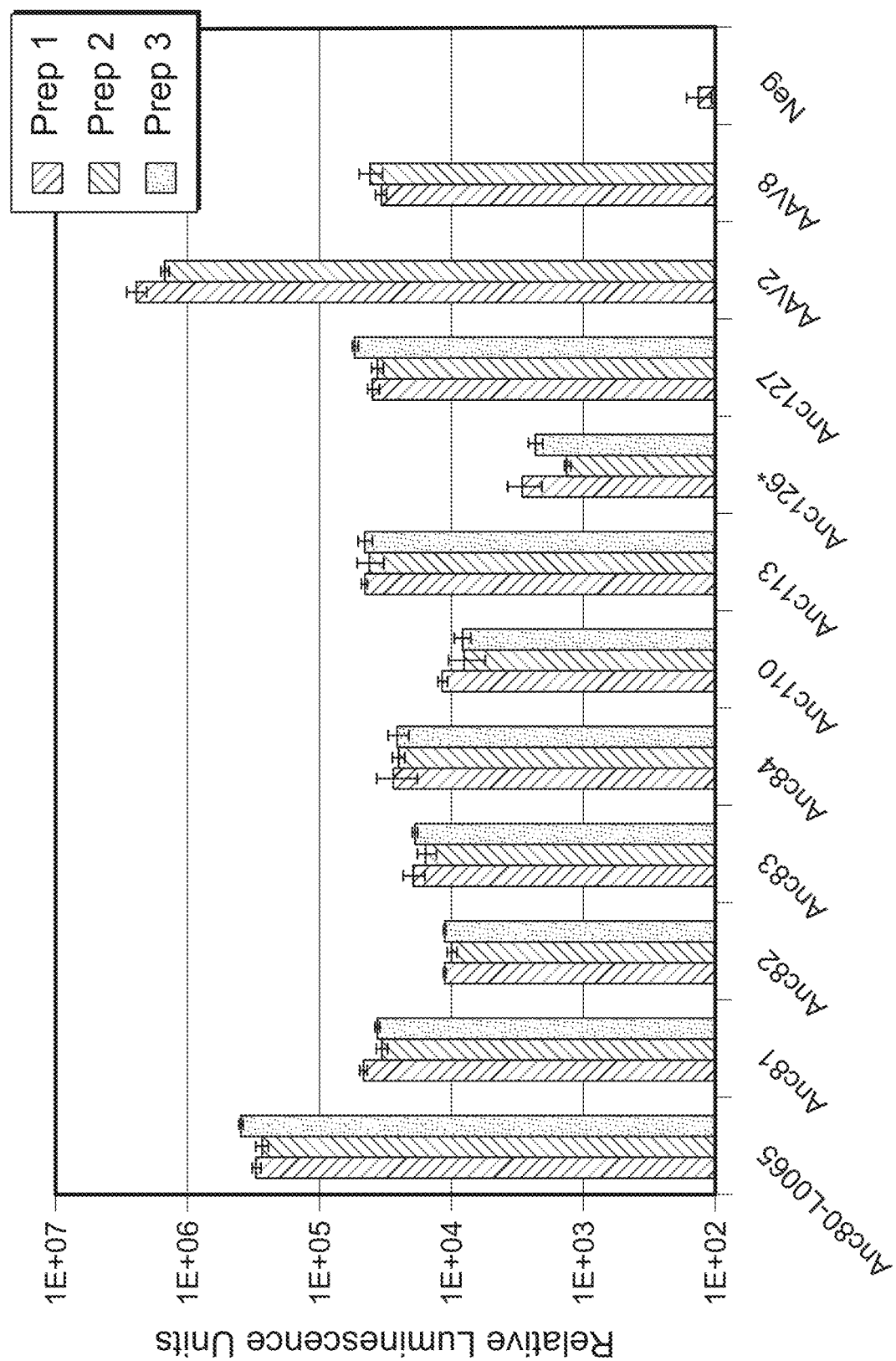
FIG. 15 is a graph showing the results of experiments in which the same cells from FIG. 16 were lysed and assayed for luciferase expression. As in FIG. 14, Anc126 was not titer controlled with the other vectors, but rather ranged from an MOI of 2.5E2-3.1E2 GC/cell.

60 hours post transduction, cells were assessed for GFP expression via fluorescence microscopy. eGFP positive cells were detected under each of the conditions except for the negative control (FIG. 14). This indicates that each of the ancestral sequences that were predicted, synthesized, and cloned is capable of producing viable, infectious virus particles. To get an idea of the relative levels of infectivity, luciferase assays also were performed on the same cells. The results indicate that each of the ancestral vectors is capable of transducing HEK293 cells between 28.3% and 850.8% relative to AAV8 (FIGS. 15 and 16). It is noted that Anc126 was excluded from the analysis of relative transduction since it was not titer-controlled.

In summary, eight novel ancestral AAV capsid genes were synthesized and used in the production of functional viral vectors along with AAV8, AAV2, and the previously described Anc80L65 vectors. Production and infectivity were assessed in vitro and a summary of those findings is shown in FIG. 17.

Example 9—Vectored Immunoprophylaxis

In vectored immunoprophylaxis, gene therapy vehicles (such as AAV) are used to deliver transgenes encoding broadly neutralizing antibodies against infectious agents. See, for example, Balazs et al. (2013, Nat. Biotechnol., 31:647-52); Limberis et al. (2013, Sci. Transl. Med., 5:187ra72); Balazs et al. (2012, Nature, 481:81-4); and Deal et al. (2014, PNAS USA, 111:12528-32). One advantage of this treatment is that the host produces the antibodies in their own cells, meaning that a single administration has the potential to confer a lifetime of protection against etiologic agents.

Example 10—Drug Delivery Vehicles

LUCENTIS® (ranibizumab) and AVASTIN® (bevacizumab) are both anti-angiogenesis agents based on the same humanized mouse monoclonal antibodies against vascular endothelial growth factor A (VEGF-A). Although bevacizumab is a full antibody and ranibizumab is a fragment (Fab), they both act to treat wet age-related macular degeneration through the same mechanism—by antagonizing VEGF. See, for example, Mao et al. (2011, Hum. Gene Ther., 22:1525-35); Xie et al. (2014, Gynecol. Oncol., doi: 10.1016/j.ygyno.2014.07.105); and Watanabe et al. (2010, Gene Ther., 17:1042-51). Because both of these molecules are proteins, they can be encoded by DNA and produced in cells transduced with vectors containing a transgene, and are small enough to be packaged into AAV vectors.

Other Embodiments

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. An adeno-associated virus (AAV) capsid polypeptide having the amino acid sequence shown in SEQ ID NO: 3.

2. The AAV capsid polypeptide of claim 1, wherein the AAV capsid polypeptide or a virus particle comprising the AAV capsid polypeptide:
   exhibits a lower seroprevalence than does an AAV2 capsid polypeptide or a virus particle comprising an AAV2 capsid polypeptide, and wherein the AAV capsid polypeptide or a virus particle comprising the AAV capsid polypeptide exhibits about the same or a lower seroprevalence than does an AAV8 capsid polypeptide or a virus particle comprising an AAV8 capsid polypeptide; and/or
   is neutralized to a lesser extent by human serum than is an AAV2 capsid polypeptide or a virus particle comprising an AAV2 capsid polypeptide, and wherein the AAV capsid polypeptide or a virus particle comprising the AAV capsid polypeptide is neutralized to a similar or lesser extent by human serum as is an AAV8 capsid polypeptide or a virus particle comprising an AAV8 capsid polypeptide.

3. The AAV capsid polypeptide of claim 1, wherein the AAV capsid polypeptide is purified.

4. The AAV capsid polypeptide of claim 1 encoded by the nucleic acid sequence shown in SEQ ID NO: 4.

5. A nucleic acid molecule encoding an adeno-associated virus (AAV) capsid polypeptide having the nucleic acid sequence shown in SEQ ID NO: 4.

6. A vector comprising the nucleic acid molecule of claim 5.

7. An isolated host cell comprising the vector of claim 6.

8. A purified virus particle comprising the AAV capsid polypeptide of claim 1.

9. The purified virus particle of claim 8, further comprising a transgene.

* * * * *

SEQUENCE LISTING

```
<160> NUMBER OF SEQ ID NOS: 44

<210> SEQ ID NO 1
<211> LENGTH: 736
<212> TYPE: PRT
<213> ORGANISM: Adeno-associated virus
<220> FEATURE:
<221> NAME/KEY: VARIANT
<222> LOCATION: (168)..(168)
<223> OTHER INFORMATION: /replace="Arg"
<220> FEATURE:
<221> NAME/KEY: VARIANT
<222> LOCATION: (204)..(204)
<223> OTHER INFORMATION: /replace="Ser"
<220> FEATURE:
<221> NAME/KEY: VARIANT
<222> LOCATION: (266)..(266)
<223> OTHER INFORMATION: /replace="Gly"
<220> FEATURE:
<221> NAME/KEY: VARIANT
<222> LOCATION: (311)..(311)
<223> OTHER INFORMATION: /replace="Lys"
<220> FEATURE:
<221> NAME/KEY: VARIANT
<222> LOCATION: (411)..(411)
<223> OTHER INFORMATION: /replace="Gln"
<220> FEATURE:
<221> NAME/KEY: VARIANT
<222> LOCATION: (460)..(460)
<223> OTHER INFORMATION: /replace="Glu"
<220> FEATURE:
<221> NAME/KEY: VARIANT
<222> LOCATION: (493)..(493)
<223> OTHER INFORMATION: /replace="Thr"
<220> FEATURE:
<221> NAME/KEY: VARIANT
<222> LOCATION: (562)..(562)
<223> OTHER INFORMATION: /replace="Asn"
<220> FEATURE:
<221> NAME/KEY: VARIANT
<222> LOCATION: (576)..(576)
<223> OTHER INFORMATION: /replace="Glu"
<220> FEATURE:
<221> NAME/KEY: VARIANT
<222> LOCATION: (587)..(587)
<223> OTHER INFORMATION: /replace="Ala"
<220> FEATURE:
<221> NAME/KEY: VARIANT
<222> LOCATION: (609)..(609)
<223> OTHER INFORMATION: /replace="Asp"
<220> FEATURE:
<221> NAME/KEY: misc_feature
<222> LOCATION: (1)..(736)
<223> OTHER INFORMATION: /note="Variant residues given in the sequence
      have no preference with respect to those in the annotations
      for variant positions"

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
```

```
            50                  55                  60
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                     85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Gly Ile Gly
145                 150                 155                 160

Lys Lys Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Ala Pro Ser Gly Val Gly Ser Asn Thr Met Ala Ala Gly Gly Gly
                195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Thr Asn Asp Asn Thr
                260                 265                 270

Tyr Phe Gly Tyr Ser Thr Pro Trp Gly Tyr Phe Asp Phe Asn Arg Phe
                275                 280                 285

His Cys His Phe Ser Pro Arg Asp Trp Gln Arg Leu Ile Asn Asn Asn
                290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Thr Thr Ile Ala Asn Asn
                325                 330                 335

Leu Thr Ser Thr Val Gln Val Phe Thr Asp Ser Glu Tyr Gln Leu Pro
                340                 345                 350

Tyr Val Leu Gly Ser Ala His Gln Gly Cys Leu Pro Pro Phe Pro Ala
                355                 360                 365

Asp Val Phe Met Ile Pro Gln Tyr Gly Tyr Leu Thr Leu Asn Asn Gly
                370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Ser Arg
                435                 440                 445

Thr Gln Thr Thr Ser Gly Thr Ala Gly Asn Arg Thr Leu Gln Phe Ser
                450                 455                 460

Gln Ala Gly Pro Ser Ser Met Ala Asn Gln Ala Lys Asn Trp Leu Pro
465                 470                 475                 480
```

Gly Pro Cys Tyr Arg Gln Arg Val Ser Lys Thr Ala Asn Gln Asn
            485                 490                 495

Asn Asn Ser Asn Phe Ala Trp Thr Gly Ala Thr Lys Tyr His Leu Asn
        500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Ser Glu Glu Glu Ile Lys Thr Thr Asn Pro Val Ala Thr Glu Gln
                565                 570                 575

Tyr Gly Thr Val Ala Thr Asn Leu Gln Ser Ser Asn Thr Ala Pro Ala
            580                 585                 590

Thr Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735

```
<210> SEQ ID NO 2
<211> LENGTH: 2208
<212> TYPE: DNA
<213> ORGANISM: Adeno-associated virus
<220> FEATURE:
<221> NAME/KEY: variation
<222> LOCATION: (502)..(504)
<223> OTHER INFORMATION: /replace="aaa"
<220> FEATURE:
<221> NAME/KEY: variation
<222> LOCATION: (610)..(612)
<223> OTHER INFORMATION: /replace="agc"
<220> FEATURE:
<221> NAME/KEY: variation
<222> LOCATION: (796)..(798)
<223> OTHER INFORMATION: /replace="ggc"
<220> FEATURE:
<221> NAME/KEY: variation
<222> LOCATION: (931)..(933)
<223> OTHER INFORMATION: /replace="aag"
<220> FEATURE:
<221> NAME/KEY: variation
<222> LOCATION: (1231)..(1233)
<223> OTHER INFORMATION: /replace="cag"
<220> FEATURE:
<221> NAME/KEY: variation
<222> LOCATION: (1378)..(1380)
<223> OTHER INFORMATION: /replace="gag"
<220> FEATURE:
```

```
<221> NAME/KEY: variation
<222> LOCATION: (1477)..(1479)
<223> OTHER INFORMATION: /replace="acc"
<220> FEATURE:
<221> NAME/KEY: variation
<222> LOCATION: (1684)..(1686)
<223> OTHER INFORMATION: /replace="aac"
<220> FEATURE:
<221> NAME/KEY: variation
<222> LOCATION: (1726)..(1728)
<223> OTHER INFORMATION: /replace="gag"
<220> FEATURE:
<221> NAME/KEY: variation
<222> LOCATION: (1759)..(1761)
<223> OTHER INFORMATION: /replace="gcc"
<220> FEATURE:
<221> NAME/KEY: variation
<222> LOCATION: (1825)..(1827)
<223> OTHER INFORMATION: /replace="gac"
<220> FEATURE:
<221> NAME/KEY: misc_feature
<222> LOCATION: (1)..(2208)
<223> OTHER INFORMATION: /note="Variation nucleotides given in the
      sequence have no preference with respect to those in the
      annotations for variation positions"

<400> SEQUENCE: 2
atggctgccg atggttatct tccagattgg ctcgaggaca acctctctga gggcattcgc      60
gagtggtggg acttgaaacc tggagccccg aaacccaaag ccaaccagca aaagcaggac     120
gacggccggg tctggtgct tcctggctac aagtacctcg acccttcaa cggactcgac      180 aaggggagc ccgtcaacgc ggcggacgca gcggccctcg agcacgacaa ggcctacgac     240
cagcagctca aagcgggtga caatccgtac ctgcggtata ccacgccga cgccgagttt     300 caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gcaatcaccc caggaaccag actcctcttc gggcatcggc     480
aagaaaggcc agcagcccgc gaagaagaga ctcaactttg gcagacagg cgactcagag     540 tcagtgcccg accctcaacc actcggagaa cccccgcag ccccctctgg tgtgggatct      600
aatacaatgg cagcaggcgg tggcgctcca atggcagaca taacgaagg cgccgacgga     660 gtgggtaacg cctcaggaaa ttggcattgc gattccacat ggctgggcga cagagtcatc     720
accaccagca cccgaacctg ggccctcccc acctacaaca accacctcta caagcaaatc     780
tccagccaat cgggagcaag caccaacgac aacacctact cggctacag cacccctgg       840 gggtattttg actttaacag attccactgc cacttctcac cacgtgactg gcagcgactc     900
atcaacaaca actggggatt ccggcccaag agactcaact tcaagctctt caacatccag     960
gtcaaggagg tcacgacgaa tgatggcacc acgaccatcg ccaataacct taccagcacg    1020
gttcaggtct ttacggactc ggaataccag ctcccgtacg tcctcggctc tgcgcaccag    1080
ggctgcctgc ctccgttccc ggcggacgtc ttcatgattc ctcagtacgg gtacctgact    1140
ctgaacaatg gcagtcaggc cgtgggccgt tcctccttct actgcctgga gtactttcct    1200
tctcaaatgc tgagaacggg caacaacttt gagttcagct acacgtttga ggacgtgcct    1260
tttcacagca gctacgcgca cagccaaagc ctggaccggc tgatgaaccc cctcatcgac    1320
cagtacctgt actacctgtc tcggactcag accacgagtg gtaccgcagg aaatcggacg    1380
ttgcaatttt ctcaggccgg gcctagtagc atggcgaatc aggccaaaaa ctggctaccc    1440 gggcctgct accggcagca acgcgtctcc aagacagcga atcaaaataa caacagcaac    1500
tttgcctgga ccggtgccac caagtatcat ctgaatggca gagactctct ggtaaatccc    1560
```

```
ggtcccgcta tggcaaccca caaggacgac gaagacaaat ttttccgat gagcggagtc      1620 ttaatatttg ggaaacaggg agctggaaat agcaacgtgg accttgacaa cgttatgata      1680
accagtgagg aagaaattaa aaccaccaac ccagtggcca cagaacagta cggcacggtg      1740
gccactaacc tgcaatcgtc aaacaccgct cctgctacag ggaccgtcaa cagtcaagga      1800
gccttacctg gcatggtctg gcagaaccgg gacgtgtacc tgcagggtcc tatctgggcc      1860
aagattcctc acacggacgg acactttcat ccctcgccgc tgatgggagg ctttggactg      1920
aaacacccgc ctcctcagat cctgattaag aatacacctg ttcccgcgaa tcctccaact      1980
accttcagtc cagctaagtt tgcgtcgttc atcacgcagt acagcaccgg acaggtcagc      2040
gtggaaattg aatgggagct gcagaaagaa aacagcaaac gctggaaccc agagattcaa      2100
tacacttcca actacaacaa atctacaaat gtggactttg ctgttgacac aaatggcgtt      2160
tattctgagc ctcgccccat cggcacccgt tacctcaccc gtaatctg               2208
```

```
<210> SEQ ID NO 3
<211> LENGTH: 737
<212> TYPE: PRT
<213> ORGANISM: Adeno-associated virus
<220> FEATURE:
<221> NAME/KEY: VARIANT
<222> LOCATION: (157)..(157)
<223> OTHER INFORMATION: /replace="Ser"
<220> FEATURE:
<221> NAME/KEY: VARIANT
<222> LOCATION: (168)..(168)
<223> OTHER INFORMATION: /replace="Arg"
<220> FEATURE:
<221> NAME/KEY: VARIANT
<222> LOCATION: (262)..(262)
<223> OTHER INFORMATION: /replace="Ser"
<220> FEATURE:
<221> NAME/KEY: VARIANT
<222> LOCATION: (263)..(263)
<223> OTHER INFORMATION: /replace="His"
<220> FEATURE:
<221> NAME/KEY: VARIANT
<222> LOCATION: (312)..(312)
<223> OTHER INFORMATION: /replace="Lys"
<220> FEATURE:
<221> NAME/KEY: VARIANT
<222> LOCATION: (412)..(412)
<223> OTHER INFORMATION: /replace="Gln"
<220> FEATURE:
<221> NAME/KEY: VARIANT
<222> LOCATION: (460)..(460)
<223> OTHER INFORMATION: /replace="Gln"
<220> FEATURE:
<221> NAME/KEY: VARIANT
<222> LOCATION: (461)..(461)
<223> OTHER INFORMATION: /replace="Glu"
<220> FEATURE:
<221> NAME/KEY: VARIANT
<222> LOCATION: (552)..(552)
<223> OTHER INFORMATION: /replace="Ser"
<220> FEATURE:
<221> NAME/KEY: VARIANT
<222> LOCATION: (556)..(556)
<223> OTHER INFORMATION: /replace="Tyr"
<220> FEATURE:
<221> NAME/KEY: VARIANT
<222> LOCATION: (557)..(557)
<223> OTHER INFORMATION: /replace="Ser"
<220> FEATURE:
<221> NAME/KEY: VARIANT
<222> LOCATION: (563)..(563)
<223> OTHER INFORMATION: /replace="Asn"
<220> FEATURE:
<221> NAME/KEY: VARIANT
<222> LOCATION: (580)..(580)
```

```
<223> OTHER INFORMATION: /replace="Ile"
<220> FEATURE:
<221> NAME/KEY: VARIANT
<222> LOCATION: (588)..(588)
<223> OTHER INFORMATION: /replace="Ser"
<220> FEATURE:
<221> NAME/KEY: VARIANT
<222> LOCATION: (664)..(664)
<223> OTHER INFORMATION: /replace="Thr"
<220> FEATURE:
<221> NAME/KEY: misc_feature
<222> LOCATION: (1)..(737)
<223> OTHER INFORMATION: /note="Variant residues given in the sequence
      have no preference with respect to those in the annotations
      for variant positions"

<400> SEQUENCE: 3
```

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Thr Gly Ile Gly
145                 150                 155                 160

Lys Lys Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ala Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Gly Ser Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Thr Thr Thr Ile Ala Asn

```
                325                 330                 335
Asn Leu Thr Ser Thr Val Gln Val Phe Thr Asp Ser Glu Tyr Gln Leu
                340                 345                 350
Pro Tyr Val Leu Gly Ser Ala His Gln Gly Cys Leu Pro Pro Phe Pro
                355                 360                 365
Ala Asp Val Phe Met Ile Pro Gln Tyr Gly Tyr Leu Thr Leu Asn Asn
                370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Glu Phe Ser Tyr Thr
                405                 410                 415
Phe Glu Asp Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Arg Thr Gln Thr Thr Gly Gly Thr Ala Gly Asn Arg Thr Leu Gln Phe
                450                 455                 460
Ser Gln Ala Gly Pro Ser Ser Met Ala Asn Gln Ala Lys Asn Trp Leu
465                 470                 475                 480
Pro Gly Pro Cys Tyr Arg Gln Gln Arg Val Ser Lys Thr Thr Asn Gln
                485                 490                 495
Asn Asn Asn Ser Asn Phe Ala Trp Thr Gly Ala Thr Lys Tyr His Leu
                500                 505                 510
Asn Gly Arg Asp Ser Leu Val Asn Pro Gly Val Ala Met Ala Thr His
                515                 520                 525
Lys Asp Asp Glu Asp Arg Phe Phe Pro Ser Ser Gly Val Leu Ile Phe
                530                 535                 540
Gly Lys Gln Gly Ala Gly Asn Asp Asn Val Asp Leu Asp Asn Val Met
545                 550                 555                 560
Ile Thr Ser Glu Glu Glu Ile Lys Thr Thr Asn Pro Val Ala Thr Glu
                565                 570                 575
Glu Tyr Gly Val Val Ala Thr Asn Leu Gln Ser Ala Asn Thr Ala Pro
                580                 585                 590
Gln Thr Gly Thr Val Asn Ser Gln Gly Ala Leu Pro Gly Met Val Trp
                595                 600                 605
Gln Asn Arg Asp Val Tyr Leu Gln Gly Pro Ile Trp Ala Lys Ile Pro
                610                 615                 620
His Thr Asp Gly Asn Phe His Pro Ser Pro Leu Met Gly Gly Phe Gly
625                 630                 635                 640
Leu Lys His Pro Pro Pro Gln Ile Leu Ile Lys Asn Thr Pro Val Pro
                645                 650                 655
Ala Asn Pro Pro Thr Thr Phe Ser Pro Ala Lys Phe Ala Ser Phe Ile
                660                 665                 670
Thr Gln Tyr Ser Thr Gly Gln Val Ser Val Glu Ile Glu Trp Glu Leu
                675                 680                 685
Gln Lys Glu Asn Ser Lys Arg Trp Asn Pro Glu Ile Gln Tyr Thr Ser
                690                 695                 700
Asn Tyr Asn Lys Ser Thr Asn Val Asp Phe Ala Val Asp Thr Glu Gly
705                 710                 715                 720
Val Tyr Ser Glu Pro Arg Pro Ile Gly Thr Arg Tyr Leu Thr Arg Asn
                725                 730                 735
Leu
```

```
<210> SEQ ID NO 4
<211> LENGTH: 2211
<212> TYPE: DNA
<213> ORGANISM: Adeno-associated virus
<220> FEATURE:
<221> NAME/KEY: variation
<222> LOCATION: (469)..(471)
<223> OTHER INFORMATION: /replace="agc"
<220> FEATURE:
<221> NAME/KEY: variation
<222> LOCATION: (502)..(504)
<223> OTHER INFORMATION: /replace="aag"
<220> FEATURE:
<221> NAME/KEY: variation
<222> LOCATION: (784)..(786)
<223> OTHER INFORMATION: /replace="agt"
<220> FEATURE:
<221> NAME/KEY: variation
<222> LOCATION: (787)..(789)
<223> OTHER INFORMATION: /replace="cac"
<220> FEATURE:
<221> NAME/KEY: variation
<222> LOCATION: (934)..(936)
<223> OTHER INFORMATION: /replace="aag"
<220> FEATURE:
<221> NAME/KEY: variation
<222> LOCATION: (1234)..(1236)
<223> OTHER INFORMATION: /replace="cag"
<220> FEATURE:
<221> NAME/KEY: variation
<222> LOCATION: (1378)..(1380)
<223> OTHER INFORMATION: /replace="cag"
<220> FEATURE:
<221> NAME/KEY: variation
<222> LOCATION: (1381)..(1383)
<223> OTHER INFORMATION: /replace="gag"
<220> FEATURE:
<221> NAME/KEY: variation
<222> LOCATION: (1654)..(1656)
<223> OTHER INFORMATION: /replace="agc"
<220> FEATURE:
<221> NAME/KEY: variation
<222> LOCATION: (1666)..(1668)
<223> OTHER INFORMATION: /replace="tac"
<220> FEATURE:
<221> NAME/KEY: variation
<222> LOCATION: (1669)..(1671)
<223> OTHER INFORMATION: /replace="agc"
<220> FEATURE:
<221> NAME/KEY: variation
<222> LOCATION: (1687)..(1689)
<223> OTHER INFORMATION: /replace="aac"
<220> FEATURE:
<221> NAME/KEY: variation
<222> LOCATION: (1738)..(1740)
<223> OTHER INFORMATION: /replace="atc"
<220> FEATURE:
<221> NAME/KEY: variation
<222> LOCATION: (1762)..(1764)
<223> OTHER INFORMATION: /replace="agc"
<220> FEATURE:
<221> NAME/KEY: variation
<222> LOCATION: (1990)..(1992)
<223> OTHER INFORMATION: /replace="acc"
<220> FEATURE:
<221> NAME/KEY: misc_feature
<222> LOCATION: (1)..(2211)
<223> OTHER INFORMATION: /note="Variation nucleotides given in the
      sequence have no preference with respect to those in the
      annotations for variation positions"

<400> SEQUENCE: 4
atggctgccg atggttatct tccagattgg ctcgaggaca acctctctga gggcattcgc     60
gagtggtggg acttgaaacc tggagccccg aaacccaaag ccaaccagca aaagcaggac    120
gacggccggg gtctggtgct tcctggctac aagtacctcg gacccttcaa cggactcgac    180
```

```
aagggggagc cgtcaacgc ggcggacgca gcggccctcg agcacgacaa ggcctacgac      240
cagcagctca aagcgggtga caatccgtac ctgcggtata accacgccga cgccgagttt      300
caggagcgtc tgcaagaaga tacgtctttt gggggcaacc tcgggcgagc agtcttccag      360
gccaagaagc gggttctcga acctctcggt ctggttgagg aaggcgctaa gacggctcct      420
ggaaagaaga gaccggtaga gcaatcaccc caggaaccag actcctctac gggcatcggc      480
aagaaaggcc agcagcccgc gaaaaagaga ctcaactttg gcagactggc gactcagag      540 tcagtgcccg accctcaacc actcggagaa ccccccgcag cccctctgg tgtgggatct       600 aatacaatgg ctgcaggcgg tggcgctcca atggcagaca taacgaagg cgccgacgga       660 gtgggtaatg cctcaggaaa ttggcattgc gattccacat ggctgggcga cagagtcatc      720
accaccagca cccgaacctg ggccctcccc acctacaaca ccacctcta caagcaaatc       780 tccaacagcc aatcgggagg aagcaccaac gacaacacct acttcggcta cagcaccccc     840
tgggggtatt ttgactttaa cagattccac tgccacttct caccacgtga ctggcagcga     900
ctcatcaaca caactgggg attccggccc aagagactca acttcaagct cttcaacatc      960
caggtcaagg aggtcacgac gaatgatggc caccgaccga tcgccaataa ccttaccagc     1020
acggttcagg tctttacgga ctcggaatac cagctcccgt acgtcctcgg ctctgcgcac     1080
cagggctgcc tgcctccgtt cccggcggac gtcttcatga ttcctcagta cgggtacctg     1140
actctgaaca atggcagtca ggccgtgggc cgttcctcct tctactgcct ggagtacttt     1200
ccttctcaaa tgctgagaac gggcaacaac tttgagttca gctacacgtt tgaggacgtg     1260 cctttttcaca gcagctacgc gcacagccaa agcctggacc ggctgatgaa ccccctcatc    1320
gaccagtacc tgtactacct gtctcggact cagaccacgg gaggtaccgc aggaaatcgg     1380
acgttgcaat tttctcaggc cgggcctagt agcatggcga atcaggccaa aaactggcta     1440
cccgggccct gctaccggca gcaacgcgtc tccaagacaa cgaatcaaaa taacaacagc     1500
aactttgcct ggaccggtgc caccaagtat catctgaatg gcagagactc tctggtaaat     1560
cccggtgtcg ctatggcaac ccacaaggac gacgaagacc gatttttcc gtccagcgga    1620 gtcttaatat ttgggaaaca gggagctgga atgacaacg tggaccttga caacgttatg     1680
ataaccagtg aggaagaaat taaaaccacc aacccagtgg ccacagaaga gtacggcgtg     1740
gtggccacta acctgcaatc ggcaaacacc gctcctcaaa cagggaccgt caacagtcaa     1800
ggagccttac ctggcatggt ctggcagaac cgggacgtgt acctgcaggg tcctatctgg     1860
gccaagattc tcacacggga cggaaacttt catccctcgc cgctgatggg aggctttgga     1920
ctgaaacacc cgcctccca gatcctgatt aagaatacac tgttcccgc gaatcctcca     1980 actaccttca gtccagctaa gtttgcgtcg ttcatcacgc agtacagcac cggacaggtc    2040
agcgtggaaa ttgaatggga gctgcagaaa gaaaacagca acgctggaa cccagagatt    2100 caatacactt ccaactacaa caatctacaa aatgtggact tgctgttga cacagaaggc    2160 gtttattctg agcctcgccc catcggcacc cgttacctca cccgtaatct g             2211
```

<210> SEQ ID NO 5
<211> LENGTH: 738
<212> TYPE: PRT
<213> ORGANISM: Adeno-associated virus
<220> FEATURE:
<221> NAME/KEY: VARIANT
<222> LOCATION: (158)..(158)
<223> OTHER INFORMATION: /replace="Ser"
<220> FEATURE:

```
<221> NAME/KEY: VARIANT
<222> LOCATION: (169)..(169)
<223> OTHER INFORMATION: /replace="Arg"
<220> FEATURE:
<221> NAME/KEY: VARIANT
<222> LOCATION: (564)..(564)
<223> OTHER INFORMATION: /replace="Asn"
<220> FEATURE:
<221> NAME/KEY: misc_feature
<222> LOCATION: (1)..(738)
<223> OTHER INFORMATION: /note="Variant residues given in the sequence
      have no preference with respect to those in the annotations
      for variant positions"

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Arg Glu Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Ser Asn Thr Met Ala Ala Gly Gly
        195                 200                 205

Gly Ala Pro Met Ala Asp Asn Asn Glu Gly Ala Asp Gly Val Gly Asn
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Thr Asn Glu Gly Thr Lys Thr Ile Ala
                325                 330                 335
```

```
Asn Asn Leu Thr Ser Thr Val Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Gly Thr Gln Thr Leu Gln
    450                 455                 460

Phe Ser Gln Ala Gly Pro Ser Ser Met Ala Asn Gln Ala Lys Asn Trp
465                 470                 475                 480

Leu Pro Gly Pro Cys Tyr Arg Gln Gln Arg Val Ser Thr Thr Thr Asn
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Gln Gly Ala Gly Asn Asp Asn Val Asp Tyr Ser Asn Val
545                 550                 555                 560

Met Ile Thr Ser Glu Glu Ile Lys Thr Thr Asn Pro Val Ala Thr
                565                 570                 575

Glu Glu Tyr Gly Val Val Ala Thr Asn Leu Gln Ser Ala Asn Thr Ala
            580                 585                 590

Pro Gln Thr Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 6
```

```
<211> LENGTH: 2214
<212> TYPE: DNA
<213> ORGANISM: Adeno-associated virus
<220> FEATURE:
<221> NAME/KEY: variation
<222> LOCATION: (472)..(474)
<223> OTHER INFORMATION: /replace="agc"
<220> FEATURE:
<221> NAME/KEY: variation
<222> LOCATION: (505)..(507)
<223> OTHER INFORMATION: /replace="aga"
<220> FEATURE:
<221> NAME/KEY: variation
<222> LOCATION: (1690)..(1692)
<223> OTHER INFORMATION: /replace="aac"
<220> FEATURE:
<221> NAME/KEY: misc_feature
<222> LOCATION: (1)..(2214)
<223> OTHER INFORMATION: /note="Variation nucleotides given in the
      sequence have no preference with respect to those in the
      annotations for variation positions"

<400> SEQUENCE: 6
atggctgccg atggttatct tccagattgg ctcgaggaca acctctctga gggcattcgc      60
gagtggtggg acctgaaacc tggagccccg aaacccaaag ccaaccagca aaagcaggac     120
gacggccggg gtctggtgct tcctggctac aagtacctcg acccttcaa cggactcgac      180 aaggggagc ccgtcaacgc ggcggacgca gcggccctcg agcacgacaa ggcctacgac     240
cagcagctca aagcgggtga caatccgtac ctgcggtata tcacgccga cgccgagttt     300 caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gcagtcacca cagcgtgagc ccgactcctc cacgggcatc     480
ggcaagaaag ccagcagcc cgccaaaaag agactcaatt tcggtcagac tggcgactca     540
gagtcagtcc ccgaccctca acctctcgga gaacctccag cagcgccctc tggtgtggga     600
tctaatacaa tggctgcagg cggtggcgca ccaatggcag acaataacga aggtgccgac     660
ggagtgggta ttcctcggg aaattggcat tgcgattcca catggctggg cgacagagtc     720
atcaccacca gcacccgaac ctgggccctg cccacctaca acaaccacct ctacaagcaa     780
atctccaacg ggacctcggg aggcagcacc aacgacaaca cctactttgg ctacagcacc     840
ccctgggggt attttgactt taacagattc cactgccact tctcaccacg tgactggcag     900
cgactcatca acaacaactg gggattccgg cccaagagac tcaacttcaa gctcttcaac     960
atccaggtca agaggtcac gacgaatgaa ggcaccaaga ccatcgccaa taacctcacc    1020
agcaccgtcc aggtgtttac ggactcggaa taccagctgc cgtacgtcct cggctctgcc    1080
caccagggct gcctgcctcc gttcccggcg gacgtcttca tgattcctca gtacggctac    1140
ctgactctca acaacggtag tcaggccgtg gacgttcct ccttctactg cctggagtac    1200
ttcccctctc agatgctgag aacgggcaac aactttcaat tcagctacac tttcgaggac    1260
gtgcctttcc acagcagcta cgcgcacagc cagagtttgg acaggctgat gaatcctctc    1320
atcgaccagt acctgtacta cctgtcaaga acccagacta cgggaggcac agcgggaacc    1380
cagacgttgc agtttctca ggccgggcct agcagcatgg cgaatcaggc caaaaactgg    1440
ctgcctggac cctgctacag acagcagcgc gtctccacga caacgaatca aaacaacaac    1500
agcaactttg cctggactgg tgccaccaag tatcatctga acggcagaga ctctctggtg    1560
aatccgggcg tcgccatggc aacccacaag gacgacgagg accgcttctt ccatccagc    1620 ggcgtcctca tatttggcaa gcagggagct ggaaatgaca acgtggacta tagcaacgtg    1680
```

```
atgataacca gcgaggaaga aatcaagacc accaacccg tggccacaga agagtatggc    1740
gtggtggcta ctaacctaca gtcggcaaac accgctcctc aaacggggac cgtcaacagc    1800
cagggagcct tacctggcat ggtctggcag aaccgggacg tgtacctgca gggtcctatt    1860
tgggccaaga ttcctcacac agatggcaac tttcacccgt ctcctttaat gggcggcttt    1920
ggacttaaac atccgcctcc tcagatcctc atcaaaaaca ctcctgttcc tgcggatcct    1980
ccaacaacgt tcaaccaggc caagctgaat tctttcatca cgcagtacag caccggacaa    2040
gtcagcgtgg agatcgagtg ggagctgcag aaggagaaca gcaagcgctg gaacccagag    2100
attcagtata cttccaacta ctacaaatct acaaatgtgg actttgctgt taatactgag    2160
ggtgtttact ctgagcctcg ccccattggc actcgttacc tcacccgtaa tctg         2214
```

<210> SEQ ID NO 7
<211> LENGTH: 738
<212> TYPE: PRT
<213> ORGANISM: Adeno-associated virus
<220> FEATURE:
<221> NAME/KEY: VARIANT
<222> LOCATION: (158)..(158)
<223> OTHER INFORMATION: /replace="Ser"
<220> FEATURE:
<221> NAME/KEY: VARIANT
<222> LOCATION: (169)..(169)
<223> OTHER INFORMATION: /replace="Lys"
<220> FEATURE:
<221> NAME/KEY: VARIANT
<222> LOCATION: (315)..(315)
<223> OTHER INFORMATION: /replace="Ser"
<220> FEATURE:
<221> NAME/KEY: VARIANT
<222> LOCATION: (413)..(413)
<223> OTHER INFORMATION: /replace="Glu"
<220> FEATURE:
<221> NAME/KEY: VARIANT
<222> LOCATION: (472)..(472)
<223> OTHER INFORMATION: /replace="Thr" or "Ser"
<220> FEATURE:
<221> NAME/KEY: VARIANT
<222> LOCATION: (534)..(534)
<223> OTHER INFORMATION: /replace="Glu"
<220> FEATURE:
<221> NAME/KEY: VARIANT
<222> LOCATION: (542)..(542)
<223> OTHER INFORMATION: /replace="Val"
<220> FEATURE:
<221> NAME/KEY: VARIANT
<222> LOCATION: (595)..(595)
<223> OTHER INFORMATION: /replace="Val"
<220> FEATURE:
<221> NAME/KEY: misc_feature
<222> LOCATION: (1)..(738)
<223> OTHER INFORMATION: /note="Variant residues given in the sequence
      have no preference with respect to those in the annotations
      for variant positions"

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

```
Gln Gln Leu Lys Ala Gly Asp Asn Pro Tyr Leu Arg Tyr Asn His Ala
             85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Gln Ser Pro Gln Arg Glu Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Ser Asn Thr Met Ala Ala Gly Gly
        195                 200                 205

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Gly Thr Gln Thr Leu Gln
450                 455                 460

Phe Ser Gln Ala Gly Pro Ser Asn Met Ala Asn Gln Ala Lys Asn Trp
465                 470                 475                 480

Leu Pro Gly Pro Cys Tyr Arg Gln Gln Arg Val Ser Thr Thr Thr Ser
                485                 490                 495
```

```
Gln Asn Asn Asn Ser Asn Phe Ala Trp Thr Gly Ala Thr Lys Tyr His
                500                 505                 510
Leu Asn Gly Arg Asp Ser Leu Val Asn Pro Gly Val Ala Met Ala Thr
            515                 520                 525
His Lys Asp Asp Glu Asp Arg Phe Phe Pro Ser Ser Gly Ile Leu Ile
        530                 535                 540
Phe Gly Lys Gln Gly Ala Gly Lys Asp Asn Val Asp Tyr Ser Asn Val
545                 550                 555                 560
Met Leu Thr Ser Glu Glu Ile Lys Thr Thr Asn Pro Val Ala Thr
                565                 570                 575
Glu Glu Tyr Gly Val Val Ala Asp Asn Leu Gln Gln Gln Asn Thr Ala
            580                 585                 590
Pro Gln Ile Gly Thr Val Asn Ser Gln Gly Ala Leu Pro Gly Met Val
        595                 600                 605
Trp Gln Asn Arg Asp Val Tyr Leu Gln Gly Pro Ile Trp Ala Lys Ile
610                 615                 620
Pro His Thr Asp Gly Asn Phe His Pro Ser Pro Leu Met Gly Gly Phe
625                 630                 635                 640
Gly Leu Lys His Pro Pro Pro Gln Ile Leu Ile Lys Asn Thr Pro Val
                645                 650                 655
Pro Ala Asp Pro Pro Thr Thr Phe Asn Gln Ala Lys Leu Asn Ser Phe
            660                 665                 670
Ile Thr Gln Tyr Ser Thr Gly Gln Val Ser Val Glu Ile Glu Trp Glu
        675                 680                 685
Leu Gln Lys Glu Asn Ser Lys Arg Trp Asn Pro Glu Ile Gln Tyr Thr
690                 695                 700
Ser Asn Tyr Tyr Lys Ser Thr Asn Val Asp Phe Ala Val Asn Thr Glu
705                 710                 715                 720
Gly Val Tyr Ser Glu Pro Arg Pro Ile Gly Thr Arg Tyr Leu Thr Arg
                725                 730                 735
Asn Leu

<210> SEQ ID NO 8
<211> LENGTH: 2214
<212> TYPE: DNA
<213> ORGANISM: Adeno-associated virus
<220> FEATURE:
<221> NAME/KEY: variation
<222> LOCATION: (472)..(474)
<223> OTHER INFORMATION: /replace="agc"
<220> FEATURE:
<221> NAME/KEY: variation
<222> LOCATION: (505)..(507)
<223> OTHER INFORMATION: /replace="aag"
<220> FEATURE:
<221> NAME/KEY: variation
<222> LOCATION: (943)..(945)
<223> OTHER INFORMATION: /replace="agc"
<220> FEATURE:
<221> NAME/KEY: variation
<222> LOCATION: (1237)..(1239)
<223> OTHER INFORMATION: /replace="gaa"
<220> FEATURE:
<221> NAME/KEY: variation
<222> LOCATION: (1414)..(1416)
<223> OTHER INFORMATION: /replace="aac" or "agc"
<220> FEATURE:
<221> NAME/KEY: variation
<222> LOCATION: (1600)..(1602)
<223> OTHER INFORMATION: /replace="gag"
<220> FEATURE:
<221> NAME/KEY: variation
<222> LOCATION: (1624)..(1626)
```

```
<223> OTHER INFORMATION: /replace="gtc"
<220> FEATURE:
<221> NAME/KEY: variation
<222> LOCATION: (1783)..(1785)
<223> OTHER INFORMATION: /replace="gta"
<220> FEATURE:
<221> NAME/KEY: misc_feature
<222> LOCATION: (1)..(2214)
<223> OTHER INFORMATION: /note="Variation nucleotides given in the
      sequence have no preference with respect to those in the
      annotations for variation positions"

<400> SEQUENCE: 8
atggctgccg atggttatct tccagattgg ctcgaggaca acctctctga gggcattcgc      60
gagtggtggg acctgaaacc tggagccccg aaacccaaag ccaaccagca aaagcaggac     120
gacggccggg gtctggtgct tcctggctac aagtacctcg acccttcaa cggactcgac     180 aagggggagc ccgtcaacgc ggcggacgca gcggccctcg agcacgacaa ggcctacgac     240
cagcagctca aagcgggtga caatccgtac ctgcggtata atcacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gcagtcacca cagcgtgagc ccgactcctc cacgggcatc     480
ggcaagaaag ccagcagcc cgccagaaag agactcaatt tcggtcagac tggcgactca     540
gagtcagtcc ccgaccctca acctctcgga gaacctccag cagcgccctc tggtgtggga     600
tctaatacaa tggctgcagg cggtggcgca ccaatggcag acaataacga aggtgccgac     660
ggagtgggta gttcctcggg aaattggcat tgcgattcca catggctggg cgacagagtc     720
atcaccacca gcacccgaac ctgggccctg cccacctaca caaccaccct ctacaagcaa     780
atctccaacg gacctcggg aggcagcacc aacgacaaca cctactttgg ctacagcacc     840
ccctgggggt attttgactt taacagattc cactgccact tctcaccacg tgactggcag     900
cgactcatca caacaactg gggattccgg cccaagagac tcaacttcaa gctcttcaac     960
atccaggtca agaggtcac gcagaatgaa ggcaccaaga ccatcgccaa taacctcacc    1020
agcaccatcc aggtgtttac ggactcggaa taccagctgc cgtacgtcct cggctctgcc    1080
caccagggct gcctgcctcc gttcccggcg gacgtcttca tgattcctca gtacggctac    1140
ctgactctca acaacggtag tcaggccgtg gacgttcct ccttctactg cctggagtac    1200
ttcccctctc agatgctgag aacgggcaac aactttcaat tcagctacac tttcgaggac    1260 gtgccttttcc acagcagcta cgcgcacagc cagagtttgg acaggctgat gaatcctctc    1320
atcgaccagt acctgtacta cctgtcaaga acccagacta cgggaggcac agcgggaacc    1380
cagacgttgc agttttctca ggccgggcct agcaacatgg cgaatcaggc caaaaactgg    1440
ctgcctggac cctgctacag acagcagcgc gtctccacga caacgtcgca aaacaacaac    1500
agcaactttg cctggactgg tgccaccaag tatcatctga acggcagaga ctctctggtg    1560
aatccgggcg tcgccatggc aacccacaag gacgacgagg accgcttctt cccatccagc    1620
ggcatcctca tatttggcaa gcagggagct ggaaaagaca cgtggacta tagcaacgtg    1680 atgctaacca gcgaggaaga aatcaagacc accaaccccg tggccacaga agagtatggc    1740
gtggtggctg ataacctaca gcagcaaaac accgctcctc aaatagggac cgtcaacagc    1800
cagggagcct acctggcat ggtctggcag aaccgggacg tgtacctgca gggtcctatt    1860
tgggccaaga ttcctcacac agatggcaac tttcacccgt ctcctttaat gggcggcttt    1920
ggacttaaac atccgcctcc tcagatcctc atcaaaaaca ctcctgttcc tgcggatcct    1980
```

-continued

```
ccaacaacgt tcaaccaggc caagctgaat tctttcatca cgcagtacag caccggacaa    2040
gtcagcgtgg agatcgagtg ggagctgcag aaggagaaca gcaagcgctg gaacccagag    2100
attcagtata cttccaacta ctacaaatct acaaatgtgg actttgctgt taatactgag    2160
ggtgtttact ctgagcctcg ccccattggc actcgttacc tcacccgtaa tctg          2214
```

<210> SEQ ID NO 9
<211> LENGTH: 738
<212> TYPE: PRT
<213> ORGANISM: Adeno-associated virus
<220> FEATURE:
<221> NAME/KEY: VARIANT
<222> LOCATION: (169)..(169)
<223> OTHER INFORMATION: /replace="Lys"
<220> FEATURE:
<221> NAME/KEY: VARIANT
<222> LOCATION: (315)..(315)
<223> OTHER INFORMATION: /replace="Ser"
<220> FEATURE:
<221> NAME/KEY: VARIANT
<222> LOCATION: (534)..(534)
<223> OTHER INFORMATION: /replace="Glu"
<220> FEATURE:
<221> NAME/KEY: VARIANT
<222> LOCATION: (542)..(542)
<223> OTHER INFORMATION: /replace="Val"
<220> FEATURE:
<221> NAME/KEY: misc_feature
<222> LOCATION: (1)..(738)
<223> OTHER INFORMATION: /note="Variant residues given in the sequence
    have no preference with respect to those in the annotations
    for variant positions"

<400> SEQUENCE: 9

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Gly Val Gly Ser Gly Thr Met Ala Ala Gly Gly
        195                 200                 205

Gly Ala Pro Met Ala Asp Asn Asn Glu Gly Ala Asp Gly Val Gly Ser
```

```
            210                 215                 220
Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
                290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
                370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Ser Thr Gly Gly Thr Ala Gly Thr Gln Gln Leu Leu
                450                 455                 460

Phe Ser Gln Ala Gly Pro Ser Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
                515                 520                 525

His Lys Asp Asp Glu Asp Arg Phe Phe Pro Ser Ser Gly Ile Leu Met
                530                 535                 540

Phe Gly Lys Gln Gly Ala Gly Lys Asp Asn Val Asp Tyr Ser Asn Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Thr Ala
                580                 585                 590

Pro Ile Val Gly Ala Val Asn Ser Gln Gly Ala Leu Pro Gly Met Val
                595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
625                 630                 635                 640
```

-continued

```
Gly Leu Lys His Pro Pro Gln Ile Leu Ile Lys Asn Thr Pro Val
                645             650                 655

Pro Ala Asp Pro Pro Thr Thr Phe Asn Gln Ala Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 10
<211> LENGTH: 2214
<212> TYPE: DNA
<213> ORGANISM: Adeno-associated virus
<220> FEATURE:
<221> NAME/KEY: variation
<222> LOCATION: (505)..(507)
<223> OTHER INFORMATION: /replace="aaa"
<220> FEATURE:
<221> NAME/KEY: variation
<222> LOCATION: (943)..(945)
<223> OTHER INFORMATION: /replace="agc"
<220> FEATURE:
<221> NAME/KEY: variation
<222> LOCATION: (1600)..(1602)
<223> OTHER INFORMATION: /replace="gag"
<220> FEATURE:
<221> NAME/KEY: variation
<222> LOCATION: (1624)..(1626)
<223> OTHER INFORMATION: /replace="gtc"
<220> FEATURE:
<221> NAME/KEY: misc_feature
<222> LOCATION: (1)..(2214)
<223> OTHER INFORMATION: /note="Variation nucleotides given in the
      sequence have no preference with respect to those in the
      annotations for variation positions"

<400> SEQUENCE: 10
atggctgccg atggttatct tccagattgg ctcgaggaca acctctctga gggcattcgc      60
gagtggtggg acctgaaacc tggagccccg aaacccaaag ccaaccagca aaagcaggac     120
gacggccggg gtctggtgct tcctggctac aagtacctcg acccttcaa cggactcgac      180 aagggggagc ccgtcaacgc ggcggacgca gcggccctcg agcacgacaa ggcctacgac     240
cagcagctca agcgggtga caatccgtac ctgcggtata tcacgccga cgccgagttt      300 caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga ccggtagag ccgtcacca cagcgttccc ccgactcctc cacgggcatc       480
ggcaagaaag ccagcagcc cgccagaaag agactcaatt tcggtcagac tggcgactca     540
gagtcagtcc ccgaccctca acctatcgga gaacctccag cagcgccctc tggtgtggga     600
tctggtacaa tggctgcagg cggtggcgca ccaatggcag acaataacga aggtgccgac     660
ggagtgggta gttcctcggg aaattggcat gcgattcca catggctggg cgacagagtc     720
atcaccacca gcacccgaac ctgggcccctg cccacctaca caaccaccct ctacaagcaa     780
atctccaacg ggaccttcgggg aggcagcacc aacgacaaca cctactttgg ctacagcacc     840
```

```
cctgggggt attttgactt taacagattc cactgccact tctcaccacg tgactggcag    900
cgactcatca acaacaactg gggattccgg cccaagagac tcaacttcaa gctcttcaac    960
atccaggtca agaggtcac gcagaatgaa ggcaccaaga ccatcgccaa taacctcacc   1020
agcaccatcc aggtgtttac ggactcggaa taccagctgc cgtacgtcct cggctctgcc   1080
caccagggct gcctgcctcc gttcccggcg gacgtcttca tgattcctca gtacggctac   1140
ctgactctca acaacggtag tcaggccgtg gacgttcct ccttctactg cctggagtac   1200
ttcccctctc agatgctgag aacgggcaac aactttgagt tcagctacac tttcgaggac   1260
gtgcctttcc acagcagcta cgcgcacagc cagagtttgg acaggctgat gaatcctctc   1320
atcgaccagt acctgtacta cctgtcaaga acccagtcta cggaggcac agcgggaacc   1380
cagcagttgc tgttttctca ggccgggcct agcaacatgt cggctcaggc caaaaactgg   1440
ctgcctggac cctgctacag acagcagcgc gtctccacga cactgtcgca aaacaacaac   1500
agcaactttg cctggactgg tgccaccaag tatcatctga acggcagaga ctctctggtg   1560
aatccgggcg tcgccatggc aacccacaag gacgacgagg accgcttctt ccatccagc   1620
ggcatcctca tgtttggcaa gcagggagct ggaaagaca acgtggacta tagcaacgtg   1680
atgctaacca gcgaggaaga aatcaagacc accaaccccg tggccacaga acagtatggc   1740
gtggtggctg ataacctaca gcagcaaaac accgctccta ttgtgggggc cgtcaacagc   1800
cagggagcct tacctggcat ggtctggcag aaccgggacg tgtacctgca gggtcctatt   1860
tgggccaaga ttcctcacac agatggcaac tttcacccgt ctcctttaat gggcggcttt   1920
ggacttaaac atccgcctcc tcagatcctc atcaaaaaca ctcctgttcc tgcggatcct   1980
ccaacaacgt tcaaccaggc caagctgaat tctttcatca cgcagtacag caccggacaa   2040
gtcagcgtgg agatcgagtg ggagctgcag aaggagaaca gcaagcgctg gaacccagag   2100
attcagtata cttccaacta ctacaaatct acaaatgtgg actttgctgt taatactgag   2160
ggtgtttact ctgagcctcg ccccattggc actcgttacc tcacccgtaa tctg         2214
```

<210> SEQ ID NO 11
<211> LENGTH: 738
<212> TYPE: PRT
<213> ORGANISM: Adeno-associated virus
<220> FEATURE:
<221> NAME/KEY: VARIANT
<222> LOCATION: (471)..(471)
<223> OTHER INFORMATION: /replace="Asn"
<220> FEATURE:
<221> NAME/KEY: misc_feature
<222> LOCATION: (1)..(738)
<223> OTHER INFORMATION: /note="Variant residues given in the sequence
      have no preference with respect to those in the annotations
      for variant positions"

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

-continued

```
Gln Gln Leu Lys Ala Gly Asp Asn Pro Tyr Leu Arg Tyr Asn His Ala
             85                  90                  95

Asp Ala Glu Phe Gln Glu Arg Leu Gln Glu Asp Thr Ser Phe Gly Gly
         100                 105                 110

Asn Leu Gly Arg Ala Val Phe Gln Ala Lys Lys Arg Val Leu Glu Pro
         115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                 165                 170                 175

Thr Gly Asp Ser Glu Ser Val Pro Asp Pro Gln Pro Ile Gly Glu Pro
             180                 185                 190

Pro Ala Gly Pro Ser Gly Leu Gly Ser Gly Thr Met Ala Ala Gly Gly
         195                 200                 205

Gly Ala Pro Met Ala Asp Asn Asn Glu Gly Ala Asp Gly Val Gly Ser
     210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                 245                 250                 255

Leu Tyr Lys Gln Ile Ser Asn Gly Thr Ser Gly Gly Ser Thr Asn Asp
             260                 265                 270

Asn Thr Tyr Phe Gly Tyr Ser Thr Pro Trp Gly Tyr Phe Asp Phe Asn
         275                 280                 285

Arg Phe His Cys His Phe Ser Pro Arg Asp Trp Gln Arg Leu Ile Asn
     290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                 325                 330                 335

Asn Asn Leu Thr Ser Thr Ile Gln Val Phe Thr Asp Ser Glu Tyr Gln
             340                 345                 350

Leu Pro Tyr Val Leu Gly Ser Ala His Gln Gly Cys Leu Pro Pro Phe
         355                 360                 365

Pro Ala Asp Val Phe Met Ile Pro Gln Tyr Gly Tyr Leu Thr Leu Asn
     370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                 405                 410                 415

Thr Phe Glu Asp Val Pro Phe His Ser Ser Tyr Ala His Ser Gln Ser
             420                 425                 430

Leu Asp Arg Leu Met Asn Pro Leu Ile Asp Gln Tyr Leu Tyr Tyr Leu
         435                 440                 445

Ser Arg Thr Gln Ser Thr Gly Gly Thr Ala Gly Thr Gln Gln Leu Leu
     450                 455                 460

Phe Ser Gln Ala Gly Pro Ser Asn Met Ser Ala Gln Ala Lys Asn Trp
465                 470                 475                 480

Leu Pro Gly Pro Cys Tyr Arg Gln Gln Arg Val Ser Thr Thr Leu Ser
                 485                 490                 495

Gln Asn Asn Asn Ser Asn Phe Ala Trp Thr Gly Ala Thr Lys Tyr His
```

```
                500             505             510
Leu Asn Gly Arg Asp Ser Leu Val Asn Pro Gly Val Ala Met Ala Thr
            515                 520             525

His Lys Asp Asp Glu Glu Arg Phe Phe Pro Ser Ser Gly Val Leu Met
            530                 535             540

Phe Gly Lys Gln Gly Ala Gly Lys Asp Asn Val Asp Tyr Ser Ser Val
545             550                 555                 560

Met Leu Thr Ser Glu Glu Glu Ile Lys Thr Thr Asn Pro Val Ala Thr
                565                 570             575

Glu Gln Tyr Gly Val Val Ala Asp Asn Leu Gln Gln Gln Asn Thr Ala
            580                 585                 590

Pro Ile Val Gly Ala Val Asn Ser Gln Gly Ala Leu Pro Gly Met Val
            595                 600             605

Trp Gln Asn Arg Asp Val Tyr Leu Gln Gly Pro Ile Trp Ala Lys Ile
            610                 615             620

Pro His Thr Asp Gly Asn Phe His Pro Ser Pro Leu Met Gly Gly Phe
625             630                 635                 640

Gly Leu Lys His Pro Pro Pro Gln Ile Leu Ile Lys Asn Thr Pro Val
                645                 650             655

Pro Ala Asp Pro Pro Thr Thr Phe Ser Gln Ala Lys Leu Ala Ser Phe
            660                 665             670

Ile Thr Gln Tyr Ser Thr Gly Gln Val Ser Val Glu Ile Glu Trp Glu
            675                 680             685

Leu Gln Lys Glu Asn Ser Lys Arg Trp Asn Pro Glu Ile Gln Tyr Thr
            690                 695             700

Ser Asn Tyr Tyr Lys Ser Thr Asn Val Asp Phe Ala Val Asn Thr Glu
705             710                 715                 720

Gly Thr Tyr Ser Glu Pro Arg Pro Ile Gly Thr Arg Tyr Leu Thr Arg
                725                 730             735

Asn Leu

<210> SEQ ID NO 12
<211> LENGTH: 2214
<212> TYPE: DNA
<213> ORGANISM: Adeno-associated virus
<220> FEATURE:
<221> NAME/KEY: variation
<222> LOCATION: (1411)..(1413)
<223> OTHER INFORMATION: /replace="aat"
<220> FEATURE:
<221> NAME/KEY: misc_feature
<222> LOCATION: (1)..(2214)
<223> OTHER INFORMATION: /note="Variation nucleotides given in the
      sequence have no preference with respect to those in the
      annotations for variation positions"

<400> SEQUENCE: 12
atggctgccg atggttatct tccagattgg ctcgaggaca acctctctga gggcattcgc     60
gagtggtggg acttgaaacc tggagccccg aaacccaaag ccaaccagca aaagcaggac    120
gacggccggg gtctggtgct tcctggctac aagtacctcg accctttcaa cggactcgac    180
aagggggagc cgtcaacgc ggcggacgca gcggccctcg agcacgacaa ggcctacgac    240
cagcagctca agcgggtga caatccgtac ctgcggtata ccacgccga cgccgagttt    300 caggagcgtc tgcaagaaga tacgtctttt gggggcaacc tcgggcgagc agtcttccag    360
gccaagaagg gggttctcga acctctcggt ctggttgagg aaggcgctaa gacggctcct    420
ggaaagaaga gaccggtaga gccatcaccc cagcgttctc cagactcctc tacgggcatc    480
```

```
ggcaagaaag gccagcagcc cgcgaaaaag agactcaact ttgggcagac tggcgactca    540
gagtcagtgc ccgaccctca accaatcgga gaaccccccg caggcccctc tggtctggga    600
tctggtacaa tggctgcagg cggtggcgct ccaatggcag acaataacga aggcgccgac    660
ggagtgggta gttcctcagg aaattggcat tgcgattcca catggctggg cgacagagtc    720
atcaccacca gcacccgaac ctgggccctc cccacctaca acaaccacct ctacaagcaa    780
atctccaacg gacttcggg aggaagcacc aacgacaaca cctacttcgg ctacagcacc    840 ccctggggt attttgactt taacagattc cactgccact tctcaccacg tgactggcag    900
cgactcatca caacaactg gggattccgg cccaagagac tcaacttcaa gctcttcaac    960
atccaggtca aggaggtcac gcagaatgaa ggcaccaaga ccatcgccaa taaccttacc   1020
agcacgattc aggtctttac ggactcggaa taccagctcc cgtacgtcct cggctctgcg   1080 caccaggct gcctgcctcc gttcccggcg gacgtcttca tgattcctca gtacgggtac   1140
ctgactctga acaatggcag tcaggccgtg gccgttcct ccttctactg cctggagtac   1200
tttccttctc aaatgctgag aacgggcaac aactttgagt tcagctacac gtttgaggac   1260
gtgccttttc acagcagcta cgcgcacagc caaagcctgg accggctgat gaacccctc    1320 atcgaccagt acctgtacta cctgtctcgg actcagtcca cgggaggtac cgcaggaact   1380
cagcagttgc tattttctca ggccgggcct agtaacatgt cggctcaggc caaaaactgg   1440 ctacccggc cctgctaccg gcagcaacgc gtctccacga cactgtcgca aaataacaac   1500
agcaactttg cctggaccgg tgccaccaag tatcatctga atggcagaga ctctctggta   1560
aatcccggtg tcgctatggc aacccacaag gacgacgaag agcgattttt tccgtccagc   1620
ggagtcttaa tgtttgggaa acagggagct ggaaaagaca cgtggacta tagcagcgtt   1680 atgctaacca gtgaggaaga aattaaaacc accaacccag tggccacaga acagtacggc   1740
gtggtggccg ataacctgca acagcaaaac accgctccta ttgtaggggc gtcaacagt   1800 caaggagcct tacctggcat ggtctggcag aaccgggacg tgtacctgca gggtcctatc   1860
tgggccaaga ttcctcacac ggacggaaac tttcatccct cgccgctgat gggaggcttt   1920
ggactgaaac acccgcctcc tcagatcctg attaagaata cacctgttcc cgcggatcct   1980
ccaactacct tcagtcaagc taagctggcg tcgttcatca cgcagtacag caccggacag   2040
gtcagcgtgg aaattgaatg ggagctgcag aaagaaaaca gcaaacgctg gaacccagag   2100
attcaataca cttccaacta ctacaaatct acaaatgtgg actttgctgt taacacagaa   2160
ggcacttatt ctgagcctcg cccatcggc acccgttacc tcacccgtaa tctg          2214
```

<210> SEQ ID NO 13
<211> LENGTH: 737
<212> TYPE: PRT
<213> ORGANISM: Adeno-associated virus
<220> FEATURE:
<221> NAME/KEY: VARIANT
<222> LOCATION: (148)..(148)
<223> OTHER INFORMATION: /replace="Gln"
<220> FEATURE:
<221> NAME/KEY: VARIANT
<222> LOCATION: (169)..(169)
<223> OTHER INFORMATION: /replace="Arg"
<220> FEATURE:
<221> NAME/KEY: VARIANT
<222> LOCATION: (314)..(314)
<223> OTHER INFORMATION: /replace="Asn"
<220> FEATURE:
<221> NAME/KEY: VARIANT
<222> LOCATION: (466)..(466)

```
<223> OTHER INFORMATION: /replace="His"
<220> FEATURE:
<221> NAME/KEY: VARIANT
<222> LOCATION: (563)..(563)
<223> OTHER INFORMATION: /replace="Ser"
<220> FEATURE:
<221> NAME/KEY: VARIANT
<222> LOCATION: (580)..(580)
<223> OTHER INFORMATION: /replace="Ile"
<220> FEATURE:
<221> NAME/KEY: VARIANT
<222> LOCATION: (588)..(588)
<223> OTHER INFORMATION: /replace="Ser"
<220> FEATURE:
<221> NAME/KEY: misc_feature
<222> LOCATION: (1)..(737)
<223> OTHER INFORMATION: /note="Variant residues given in the sequence
      have no preference with respect to those in the annotations
      for variant positions"

<400> SEQUENCE: 13
```

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Ser Gly Thr Met Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

```
Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Thr Thr Gly Gly Thr Ala Gly Asn Arg Glu Leu Gln
450                 455                 460

Phe Tyr Gln Ala Gly Pro Ser Thr Met Ala Glu Gln Ala Lys Asn Trp
465                 470                 475                 480

Leu Pro Gly Pro Cys Tyr Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
530                 535                 540

Phe Gly Lys Thr Gly Ala Ala Asn Lys Thr Thr Leu Glu Asn Val Leu
545                 550                 555                 560

Met Thr Asn Glu Glu Glu Ile Lys Thr Thr Asn Pro Val Ala Thr Glu
                565                 570                 575

Glu Tyr Gly Val Val Ser Ser Asn Leu Gln Ser Ala Asn Thr Ala Pro
            580                 585                 590

Gln Thr Gln Thr Val Asn Ser Gln Gly Ala Leu Pro Gly Met Val Trp
        595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
690                 695                 700

Asn Tyr Asp Lys Ser Thr Asn Val Asp Phe Ala Val Asp Ser Glu Gly
705                 710                 715                 720

Val Tyr Ser Glu Pro Arg Pro Ile Gly Thr Arg Tyr Leu Thr Arg Asn
```

Leu

<210> SEQ ID NO 14
<211> LENGTH: 2211
<212> TYPE: DNA
<213> ORGANISM: Adeno-associated virus
<220> FEATURE:
<221> NAME/KEY: variation
<222> LOCATION: (442)..(444)
<223> OTHER INFORMATION: /replace="cag"
<220> FEATURE:
<221> NAME/KEY: variation
<222> LOCATION: (505)..(507)
<223> OTHER INFORMATION: /replace="aga"
<220> FEATURE:
<221> NAME/KEY: variation
<222> LOCATION: (940)..(942)
<223> OTHER INFORMATION: /replace="aac"
<220> FEATURE:
<221> NAME/KEY: variation
<222> LOCATION: (1396)..(1398)
<223> OTHER INFORMATION: /replace="cac"
<220> FEATURE:
<221> NAME/KEY: variation
<222> LOCATION: (1687)..(1689)
<223> OTHER INFORMATION: /replace="agt"
<220> FEATURE:
<221> NAME/KEY: variation
<222> LOCATION: (1738)..(1740)
<223> OTHER INFORMATION: /replace="ata"
<220> FEATURE:
<221> NAME/KEY: variation
<222> LOCATION: (1762)..(1764)
<223> OTHER INFORMATION: /replace="tct"
<220> FEATURE:
<221> NAME/KEY: misc_feature
<222> LOCATION: (1)..(2211)
<223> OTHER INFORMATION: /note="Variation nucleotides given in the sequence have no preference with respect to those in the annotations for variation positions"

<400> SEQUENCE: 14

| | | | | |
|---|---|---|---|---|
| atggctgccg | atggttatct | tccagattgg | ctcgaggaca | acctctctga gggcattcgc | 60 |
| gagtggtggg | acctgaaacc | tggagccccg | aaacccaaag | ccaaccagca aaagcaggac | 120 |
| gacggccggg | gtctggtgct | tcctggctac | aagtacctcg | acccttcaa cggactcgac | 180 |
| aagggggagc | ccgtcaacgc | ggcggacgca | gcggccctcg | agcacgacaa ggcctacgac | 240 |
| cagcagctca | aagcgggtga | caatccgtac | ctgcggtata | accacgccga cgccgagttt | 300 |
| caggagcgtc | tgcaagaaga | tacgtcattt | gggggcaacc | tcgggcgagc agtcttccag | 360 |
| gccaagaagc | gggttctcga | acctctcggt | ctggttgagg | aaggcgctaa gacggctcct | 420 |
| ggaaagaaga | gaccggtaga | gccgtcacct | cagcgttccc | ccgactcctc cacgggcatc | 480 |
| ggcaagaaag | gccagcagcc | cgccaaaaag | agactcaatt | tcggtcagac tggcgactca | 540 |
| gagtcagtcc | ccgaccctca | acctctcgga | gaacctccag | cagcgccctc tggtgtggga | 600 |
| tctggtacaa | tggctgcagg | cggtggcgca | ccaatggcag | acaataacga aggtgccgac | 660 |
| ggagtgggta | atgcctcagg | aaattggcat | tgcgattcca | catggctggg cgacagagtc | 720 |
| attaccacca | gcacccgaac | ctgggccctg | cccacctaca | acaaccacct ctacaagcaa | 780 |
| atctccagtc | aaagtgcagg | tagtaccaac | gacaacacct | acttcggcta cagcaccccc | 840 |
| tgggggtatt | ttgactttaa | cagattccac | tgccacttct | caccacgtga ctggcagcga | 900 |
| ctcatcaaca | acaactgggg | attccggccc | aagaagctgc | ggttcaagct cttcaacatc | 960 |
| caggtcaagg | aggtcacgac | gaatgacggc | gttacgacca | tcgctaataa ccttaccagc | 1020 |

-continued

```
acggttcagg tattctcgga ctcggaatac cagctgccgt acgtcctcgg ctctgcgcac    1080
cagggctgcc tgcctccgtt cccggcggac gtcttcatga ttcctcagta cggctacctg    1140
actctcaaca atggcagtca gtctgtggga cgttcctcct tctactgcct ggagtacttc    1200
ccctctcaga tgctgagaac gggcaacaac tttgagttca gctacacctt cgaggacgtg    1260
cctttccaca gcagctacgc acacagccag agcctggacc ggctgatgaa tcccctcatc    1320
gaccagtact tgtactacct ggccagaaca cagagtacca caggaggcac agctggcaat    1380
cgggaactgc agttttacca ggccgggcct tcaactatgg ccgaacaagc caagaattgg    1440
ttacctggac cttgctaccg gcaacaaaga gtctccaaaa cgctggatca aaacaacaac    1500
agcaactttg cttggactgg tgccaccaaa tatcacctga acggcagaaa ctcgttggtt    1560
aatcccggcg tcgccatggc aactcacaag gacgacgagg accgcttttt cccatccagc    1620
ggagtcctga ttttggaaa actggagca gctaacaaaa ctacattgga aaatgtgtta    1680
atgacaaatg aagaagaaat taaaactact aatcctgtag ccacgaaaga atacggggta    1740
gtcagcagca acttacaatc ggctaatact gcaccccaga cacaaactgt caacagccag    1800
ggagccttac ctggcatggt ctggcagaac cgggacgtgt acctgcaggg tcccatctgg    1860
gccaagattc ctcacacgga tggcaacttt caccctctc ctttgatggg cggctttgga    1920
cttaaacatc cgcctcctca gatcctgatc aagaacactc ccgttcccgc taatcctccg    1980
gaggtgttta ctcctgccaa gtttgcttcg ttcatcacac agtacagcac cggacaagtc    2040
agcgtggaaa tcgagtggga gctgcagaag gaaaacagca gcgctggaa cccggagatt    2100 cagtacacct ccaactatga taagtcgact aatgtggact ttgccgttga cagcgagggt    2160
gtttactctg agcctcgccc tattggcact cgttacctca cccgtaatct g              2211
```

```
<210> SEQ ID NO 15
<211> LENGTH: 735
<212> TYPE: PRT
<213> ORGANISM: Adeno-associated virus
<220> FEATURE:
<221> NAME/KEY: VARIANT
<222> LOCATION: (162)..(162)
<223> OTHER INFORMATION: /replace="Thr"
<220> FEATURE:
<221> NAME/KEY: VARIANT
<222> LOCATION: (168)..(168)
<223> OTHER INFORMATION: /replace="Arg"
<220> FEATURE:
<221> NAME/KEY: VARIANT
<222> LOCATION: (224)..(224)
<223> OTHER INFORMATION: /replace="Ser"
<220> FEATURE:
<221> NAME/KEY: VARIANT
<222> LOCATION: (310)..(310)
<223> OTHER INFORMATION: /replace="Lys"
<220> FEATURE:
<221> NAME/KEY: VARIANT
<222> LOCATION: (410)..(410)
<223> OTHER INFORMATION: /replace="Gln"
<220> FEATURE:
<221> NAME/KEY: VARIANT
<222> LOCATION: (446)..(446)
<223> OTHER INFORMATION: /replace="Asn"
<220> FEATURE:
<221> NAME/KEY: VARIANT
<222> LOCATION: (461)..(461)
<223> OTHER INFORMATION: /replace="Leu"
<220> FEATURE:
<221> NAME/KEY: VARIANT
<222> LOCATION: (471)..(471)
<223> OTHER INFORMATION: /replace="Ser"
<220> FEATURE:
```

<221> NAME/KEY: VARIANT
<222> LOCATION: (708)..(708)
<223> OTHER INFORMATION: /replace="Thr"
<220> FEATURE:
<221> NAME/KEY: misc_feature
<222> LOCATION: (1)..(735)
<223> OTHER INFORMATION: /note="Variant residues given in the sequence have no preference with respect to those in the annotations for variant positions"

<400> SEQUENCE: 15

```
Met Ala Ala Asp Gly Tyr Leu Pro Asp Trp Leu Glu Asp Asn Leu Ser
 1               5                  10                  15

Glu Gly Ile Arg Glu Trp Trp Asp Leu Lys Pro Gly Ala Pro Lys Pro
             20                  25                  30

Lys Ala Asn Gln Gln Lys Gln Asp Asp Gly Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Thr Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
```

```
                355                 360                 365
Val Phe Met Ile Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Gln Thr Thr Ser Gly Thr Ala Gln Asn Arg Glu Leu Gln Phe Ser Gln
    450                 455                 460

Ala Gly Pro Ser Ser Met Ala Asn Gln Ala Lys Asn Trp Leu Pro Gly
465                 470                 475                 480

Pro Cys Tyr Arg Gln Gln Arg Val Ser Lys Thr Ala Asn Asp Asn Asn
                485                 490                 495

Asn Ser Asn Phe Ala Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Asp Lys Phe Phe Pro Met Ser Gly Val Leu Ile Phe Gly Lys
    530                 535                 540

Gln Gly Ala Gly Ala Ser Asn Val Asp Leu Asp Asn Val Met Ile Thr
545                 550                 555                 560

Asp Glu Glu Glu Ile Lys Thr Thr Asn Pro Val Ala Thr Glu Gln Tyr
                565                 570                 575

Gly Thr Val Ala Thr Asn Leu Gln Ser Ser Asn Thr Ala Pro Ala Thr
            580                 585                 590

Gly Thr Val Asn Ser Gln Gly Ala Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Pro Thr Thr Phe Ser Pro Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Ala Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 16
<211> LENGTH: 2205
<212> TYPE: DNA
<213> ORGANISM: Adeno-associated virus
<220> FEATURE:
<221> NAME/KEY: variation
<222> LOCATION: (484)..(486)
```

| | | |
|---|---|---|
| <223> | OTHER INFORMATION: /replace="aca" | |
| <220> | FEATURE: | |
| <221> | NAME/KEY: variation | |
| <222> | LOCATION: (502)..(504) | |
| <223> | OTHER INFORMATION: /replace="aga" | |
| <220> | FEATURE: | |
| <221> | NAME/KEY: variation | |
| <222> | LOCATION: (670)..(672) | |
| <223> | OTHER INFORMATION: /replace="tcc" | |
| <220> | FEATURE: | |
| <221> | NAME/KEY: variation | |
| <222> | LOCATION: (928)..(930) | |
| <223> | OTHER INFORMATION: /replace="aaa" | |
| <220> | FEATURE: | |
| <221> | NAME/KEY: variation | |
| <222> | LOCATION: (1228)..(1230) | |
| <223> | OTHER INFORMATION: /replace="cag" | |
| <220> | FEATURE: | |
| <221> | NAME/KEY: variation | |
| <222> | LOCATION: (1336)..(1338) | |
| <223> | OTHER INFORMATION: /replace="aac" | |
| <220> | FEATURE: | |
| <221> | NAME/KEY: variation | |
| <222> | LOCATION: (1381)..(1383) | |
| <223> | OTHER INFORMATION: /replace="ctg" | |
| <220> | FEATURE: | |
| <221> | NAME/KEY: variation | |
| <222> | LOCATION: (1411)..(1413) | |
| <223> | OTHER INFORMATION: /replace="tct" | |
| <220> | FEATURE: | |
| <221> | NAME/KEY: variation | |
| <222> | LOCATION: (2122)..(2124) | |
| <223> | OTHER INFORMATION: /replace="acc" | |
| <220> | FEATURE: | |
| <221> | NAME/KEY: misc_feature | |
| <222> | LOCATION: (1)..(2205) | |
| <223> | OTHER INFORMATION: /note="Variation nucleotides given in the sequence have no preference with respect to those in the annotations for variation positions" | |

<400> SEQUENCE: 16

```
atggctgccg atggttatct tccagattgg ctcgaggaca acctctctga gggcattcgc      60
gagtggtggg acttgaaacc tggagccccg aaacccaaag ccaaccagca aaagcaggac     120
gacggccggg gtctggtgct tcctggctac aagtacctcg acccttcaa cggactcgac      180 aagggggagc ccgtcaacgc ggcggatgca gcggccctcg agcacgacaa ggcctacgac     240
cagcagctca aagcgggtga caatccgtac ctgcggtata ccacgccga cgccgagttt     300 caggagcgtc tgcaagaaga tacgtctttt gggggcaacc tcgggcgagc agtcttccag    360
gccaagaaga gggttctcga acctcttggt ctggttgagg aaggtgctaa gacggctcct    420
ggaaagaaac gtccggtaga gcagtcgcca caagagccag actcctcctc gggcattggc    480
aagtcaggcc agcagcccgc taaaaagaga ctcaattttg gtcagactgg cgactcagag    540
tcagtccccg acccacaacc tctcggagaa cctccagcag cccctctgg tgtgggatct     600 aatacaatgg cttcaggcgg tggcgcacca atggcagaca taacgaagg cgccgacgga    660 gtgggtaatg cctcaggaaa ttggcattgc gattccacat ggctgggcga cagagtcatc    720
accaccagca cccgaacatg ggccttgccc acctataaca accacctcta caagcaaatc    780
tccagtcaat caggggccag caacgacaac cactacttcg gctacagcac ccctggggg    840 tattttgatt tcaacagatt ccactgccat ttctcaccac gtgactggca gcgactcatc    900
aacaacaatt ggggattccg gcccaagaga ctcaacttca gctcttcaa catccaagtc    960 aaggaggtca cgacgaatga tggcaccacg accatcgcta ataaccttac cagcacggtt   1020
caagtcttca cggactcgga gtaccagttg ccgtacgtcc tcggctctgc gcaccagggc   1080
tgcctccctc cgttcccggc ggacgtgttc atgattccgc agtacggcta cctaacgctc   1140
```

-continued

```
aacaatggca gccaggcagt gggacggtca tccttttact gcctggaata tttcccatcg    1200
cagatgctga gaacgggcaa taactttacc ttcagctaca ccttcgagga cgtgcctttc    1260
cacagcagct acgcgcacag ccagagcctg gaccggctga tgaatcctct catcgaccag    1320
tacctgtatt acctgagcag aactcagact acgtccggaa ctgcccaaaa cagggagttg    1380
cagtttagcc aggcgggtcc atctagcatg gctaatcagg ccaaaaactg gctacctgga    1440
ccctgttacc ggcagcagcg cgtttctaaa acagcaaatg acaacaacaa cagcaacttt    1500
gcctggactg gtgctacaaa atatcacctt aatgggcgtg attctttagt caaccctggc    1560
cctgctatgg cctcacacaa agacgacgaa gacaagttct ttcccatgag cggtgtcttg    1620 attttggaa agcagggcgc cggagcttca aacgttgatt tggacaatgt catgatcaca    1680
gacgaagagg aaatcaaaac cactaacccc gtggccaccg aacaatatgg gactgtggca    1740
accaatctcc agagcagcaa cacagcccct gcgaccggaa ctgtgaattc tcagggagcc    1800
ttacctggaa tggtgtggca agacagagac gtatacctgc agggtcctat ttgggccaaa    1860
attcctcaca cggatggaca ctttcacccg tctcctctca tgggcggctt tggacttaag    1920
cacccgcctc ctcagatcct catcaaaaac acgcctgttc ctgcgaatcc tccgacaacg    1980
ttttcgcctg caaagtttgc ttcattcatc acccagtatt ccacaggaca agtgagcgtg    2040
gagattgaat gggagctgca gaaagaaaac agcaaacgct ggaatcccga aatacagtat    2100
acatctaact ataataaatc tgccaacgtt gatttcactg tggacaccaa tggagtttat    2160
agtgagcctc gccccattgg cacccgttac ctcacccgta acctg                    2205
```

```
<210> SEQ ID NO 17
<211> LENGTH: 735
<212> TYPE: PRT
<213> ORGANISM: Adeno-associated virus
<220> FEATURE:
<221> NAME/KEY: VARIANT
<222> LOCATION: (42)..(42)
<223> OTHER INFORMATION: /replace="Ser"
<220> FEATURE:
<221> NAME/KEY: VARIANT
<222> LOCATION: (168)..(168)
<223> OTHER INFORMATION: /replace="Lys"
<220> FEATURE:
<221> NAME/KEY: VARIANT
<222> LOCATION: (310)..(310)
<223> OTHER INFORMATION: /replace="Arg"
<220> FEATURE:
<221> NAME/KEY: VARIANT
<222> LOCATION: (410)..(410)
<223> OTHER INFORMATION: /replace="Gln"
<220> FEATURE:
<221> NAME/KEY: VARIANT
<222> LOCATION: (446)..(446)
<223> OTHER INFORMATION: /replace="Arg"
<220> FEATURE:
<221> NAME/KEY: VARIANT
<222> LOCATION: (461)..(461)
<223> OTHER INFORMATION: /replace="Leu"
<220> FEATURE:
<221> NAME/KEY: VARIANT
<222> LOCATION: (471)..(471)
<223> OTHER INFORMATION: /replace="Ser"
<220> FEATURE:
<221> NAME/KEY: VARIANT
<222> LOCATION: (475)..(475)
<223> OTHER INFORMATION: /replace="Arg"
<220> FEATURE:
<221> NAME/KEY: VARIANT
<222> LOCATION: (504)..(504)
<223> OTHER INFORMATION: /replace="Ala"
<220> FEATURE:
```

<220> FEATURE:
<221> NAME/KEY: VARIANT
<222> LOCATION: (539)..(539)
<223> OTHER INFORMATION: /replace="Asn"
<220> FEATURE:
<221> NAME/KEY: misc_feature
<222> LOCATION: (1)..(735)
<223> OTHER INFORMATION: /note="Variant residues given in the sequence have no preference with respect to those in the annotations for variant positions"

<400> SEQUENCE: 17

```
Met Ala Ala Asp Gly Tyr Leu Pro Asp Trp Leu Glu Asp Asn Leu Ser
  1               5                  10                  15

Glu Gly Ile Arg Glu Trp Trp Asp Leu Lys Pro Gly Ala Pro Gln Pro
             20                  25                  30

Lys Ala Asn Gln Gln His Gln Asp Asp Gly Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Glu Ala Asp Ala Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Ser Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
```

```
                     355                 360                 365
Val Phe Met Ile Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Gln Thr Thr Ser Gly Thr Thr Gln Gln Ser Arg Leu Gln Phe Ser Gln
450                 455                 460

Ala Gly Pro Ser Ser Met Ala Gln Gln Ala Lys Asn Trp Leu Pro Gly
465                 470                 475                 480

Pro Cys Tyr Arg Gln Gln Arg Val Ser Lys Thr Ala Asn Asp Asn Asn
                485                 490                 495

Asn Ser Asn Phe Ala Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Met His Gly Val Leu Ile Phe Gly Lys
530                 535                 540

Gln Gly Thr Gly Ala Ser Asn Val Asp Leu Asp Asn Val Met Ile Thr
545                 550                 555                 560

Asp Glu Glu Glu Ile Arg Thr Thr Asn Pro Val Ala Thr Glu Gln Tyr
                565                 570                 575

Gly Thr Val Ala Thr Asn Leu Gln Ser Ser Asn Thr Ala Pro Ala Thr
                580                 585                 590

Gly Thr Val Asn Ser Gln Gly Ala Leu Pro Gly Met Val Trp Gln Asp
                595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Pro Thr Thr Phe Ser Pro Ala Lys Phe Ala Ser Phe Ile Thr Gln
                660                 665                 670

Tyr Ser Thr Gly Gln Val Ser Val Glu Ile Glu Trp Glu Leu Gln Lys
                675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 18
<211> LENGTH: 2205
<212> TYPE: DNA
<213> ORGANISM: Adeno-associated virus
<220> FEATURE:
<221> NAME/KEY: variation
<222> LOCATION: (124)..(126)
```

```
<223> OTHER INFORMATION: /replace="agt"
<220> FEATURE:
<221> NAME/KEY: variation
<222> LOCATION: (502)..(504)
<223> OTHER INFORMATION: /replace="aaa"
<220> FEATURE:
<221> NAME/KEY: variation
<222> LOCATION: (928)..(930)
<223> OTHER INFORMATION: /replace="aga"
<220> FEATURE:
<221> NAME/KEY: variation
<222> LOCATION: (1228)..(1230)
<223> OTHER INFORMATION: /replace="cag"
<220> FEATURE:
<221> NAME/KEY: variation
<222> LOCATION: (1336)..(1338)
<223> OTHER INFORMATION: /replace="aga"
<220> FEATURE:
<221> NAME/KEY: variation
<222> LOCATION: (1381)..(1383)
<223> OTHER INFORMATION: /replace="ctc"
<220> FEATURE:
<221> NAME/KEY: variation
<222> LOCATION: (1411)..(1413)
<223> OTHER INFORMATION: /replace="tct"
<220> FEATURE:
<221> NAME/KEY: variation
<222> LOCATION: (1423)..(1425)
<223> OTHER INFORMATION: /replace="aga"
<220> FEATURE:
<221> NAME/KEY: variation
<222> LOCATION: (1510)..(1512)
<223> OTHER INFORMATION: /replace="gcg"
<220> FEATURE:
<221> NAME/KEY: variation
<222> LOCATION: (1615)..(1617)
<223> OTHER INFORMATION: /replace="gac"
<220> FEATURE:
<221> NAME/KEY: misc_feature
<222> LOCATION: (1)..(2205)
<223> OTHER INFORMATION: /note="Variation nucleotides given in the
      sequence have no preference with respect to those in the
      annotations for variation positions"

<400> SEQUENCE: 18
atggctgctg acggttatct tccagattgg ctcgaggaca acctttctga aggcattcgt      60
gagtggtggg atctgaaacc tggagcccct caacccaaag cgaaccaaca acaccaggac     120
gacggtcggg gtcttgtgct tccgggttac aaataccctcg gacccttaa cggactcgac     180 aaaggagagc cggtcaacga ggcggacgcg gcagccctcg aacacgacaa agcttacgac     240
cagcagctca aggccggtga caacccgtac ctcaagtaca ccacgccga cgccgagttt     300 caggagcgtc ttcaagaaga tacgtctttt gggggcaacc ttggcagagc agtcttccag     360
gccaaaaaga gggtccttga gcctcttggt ctggttgagg aagcagctaa acggctcct     420 ggaaagaaga ggcctgtaga acagtctcct caggaaccgg actcatcatc tggtattggc     480
aaatcgggcc aacagcctgc cagaaaaaga ctaaatttcg gtcagactgg agactcagag     540
tcagtcccag accctcaacc tctcggagaa ccaccagcag cccctcagg tgtgggatct     600 aatacaatgg cttcaggcgg tggcgcacca atggcagaca taacgaggg tgccgatgga     660 gtgggtaatt cctcaggaaa ttggcattgc gattccacat ggctgggcga cagagtcatc     720
accaccagca ccagaacctg ggccctgccc acttacaaca accatctcta caagcaaatc     780
tccagccaat caggagcttc aaacgacaac cactactttg ctacagcac ccttgggggg     840 tattttgact ttaacagatt ccactgccac ttctcaccac gtgactggca gcgactcatt     900
aacaacaact ggggattccg gcccaagaaa ctcaacttca gctcttcaa catccaagtt     960 aaagaggtca cgcagaacga tggcacgacg actattgcca ataaccttac cagcacggtt    1020
```

-continued

```
caagtgttta cggactcgga gtatcagctc ccgtacgtgc tcgggtcggc gcaccaaggc      1080
tgtctcccgc cgtttccagc ggacgtcttc atgatccctc agtatggata cctcaccctg      1140
aacaacggaa gtcaagcggt gggacgctca tccttttact gcctggagta cttcccttcg      1200
cagatgctaa ggactggaaa taacttcaca ttcagctata ccttcgagga tgtacctttt      1260
cacagcagct acgctcacag ccagagtttg gatcgcttga tgaatcctct tattgatcag      1320
tatctgtact acctgagcag aacgcaaaca acctctggaa caacccaaca atcacggctg      1380
caatttagcc aggctgggcc ttcgtctatg gctcagcagg ccaaaaattg gctacctggg      1440
ccctgctacc ggcaacagag agtttcaaag actgctaacg acaacaacaa cagtaacttt      1500
gcttggacag gggccaccaa atatcatctc aatggccgcg actcgctggt gaatccagga      1560
ccagctatgg ccagtcacaa ggacgatgaa gaaaaatttt tccctatgca cggcgttcta      1620
atatttggca acaagggac aggggcaagt aacgtagatt tagataatgt aatgattacg      1680
gatgaagaag agattcgtac caccaatcct gtggcaacag agcagtatgg aactgtggca      1740
actaacttgc agagctcaaa tacagctccc gcgactggaa ctgtcaatag tcaggggcc      1800
ttacctggca tggtgtggca agatcgtgac gtgtaccttc aaggacctat ctgggcaaag      1860
attcctcaca cggatggaca ctttcatcct tctcctctga tgggaggctt tggactgaaa      1920
catccgcctc ctcaaatctt gatcaaaaat actccggtac cggcaaatcc tccgacgact      1980
ttcagcccgg ccaagtttgc ttcatttatc actcagtact ccactggaca ggtcagcgtg      2040
gaaattgagt gggagctaca gaaagaaaac agcaaacgtt ggaatccaga gattcagtac      2100
acttccaact acaacaagtc tgttaatgtg gactttactg tagacactaa tggtgtttat      2160
agtgaacctc gccctattgg aacccggtat ctcacacgaa acttg                      2205
```

<210> SEQ ID NO 19
<211> LENGTH: 736
<212> TYPE: PRT
<213> ORGANISM: Adeno-associated virus

<400> SEQUENCE: 19

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Gly Ile Gly
145                 150                 155                 160
```

-continued

```
Lys Lys Gly Gln Gln Pro Ala Arg Lys Arg Leu Asn Phe Gly Gln Thr
            165                 170                 175
Gly Asp Ser Glu Ser Val Pro Asp Pro Gln Pro Leu Gly Glu Pro Pro
        180                 185                 190
Ala Ala Pro Ser Gly Val Gly Ser Asn Thr Met Ala Ala Gly Gly Gly
        195                 200                 205
Ala Pro Met Ala Asp Asn Asn Glu Gly Ala Asp Gly Val Gly Asn Ala
        210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Gly Ser Thr Asn Asp Asn Thr
            260                 265                 270
Tyr Phe Gly Tyr Ser Thr Pro Trp Gly Tyr Phe Asp Phe Asn Arg Phe
        275                 280                 285
His Cys His Phe Ser Pro Arg Asp Trp Gln Arg Leu Ile Asn Asn Asn
        290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Thr Thr Thr Ile Ala Asn Asn
                325                 330                 335
Leu Thr Ser Thr Val Gln Val Phe Thr Asp Ser Glu Tyr Gln Leu Pro
            340                 345                 350
Tyr Val Leu Gly Ser Ala His Gln Gly Cys Leu Pro Pro Phe Pro Ala
        355                 360                 365
Asp Val Phe Met Ile Pro Gln Tyr Gly Tyr Leu Thr Leu Asn Asn Gly
        370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Glu Phe Ser Tyr Thr Phe
                405                 410                 415
Glu Asp Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Ser Arg
        435                 440                 445
Thr Gln Thr Thr Ser Gly Thr Ala Gly Asn Arg Thr Leu Gln Phe Ser
        450                 455                 460
Gln Ala Gly Pro Ser Ser Met Ala Asn Gln Ala Lys Asn Trp Leu Pro
465                 470                 475                 480
Gly Pro Cys Tyr Arg Gln Gln Arg Val Ser Lys Thr Ala Asn Gln Asn
                485                 490                 495
Asn Asn Ser Asn Phe Ala Trp Thr Gly Ala Thr Lys Tyr His Leu Asn
            500                 505                 510
Gly Arg Asp Ser Leu Val Asn Pro Gly Pro Ala Met Ala Thr His Lys
        515                 520                 525
Asp Asp Glu Asp Lys Phe Phe Pro Met Ser Gly Val Leu Ile Phe Gly
        530                 535                 540
Lys Gln Gly Ala Gly Asn Ser Asn Val Asp Leu Asp Asn Val Met Ile
545                 550                 555                 560
Thr Asn Glu Glu Glu Ile Lys Thr Thr Asn Pro Val Ala Thr Glu Gln
                565                 570                 575
Tyr Gly Thr Val Ala Thr Asn Leu Gln Ser Ala Asn Thr Ala Pro Ala
```

```
                580                 585                 590
Thr Gly Thr Val Asn Ser Gln Gly Ala Leu Pro Gly Met Val Trp Gln
            595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys His Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 20
<211> LENGTH: 736
<212> TYPE: PRT
<213> ORGANISM: Adeno-associated virus

<400> SEQUENCE: 20

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Gly Ile Gly
145                 150                 155                 160

Lys Lys Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ala
    210                 215                 220
```

```
Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Thr Asn Asp Asn Thr
                260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
                340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Ser Arg
            435                 440                 445

Thr Gln Thr Thr Ser Gly Thr Ala Gly Asn Arg Glu Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Thr Asn Gln Asn
            485                 490                 495

Asn Asn Ser Asn Phe Ala Trp Thr Gly Ala Thr Lys Tyr His Leu Asn
                500                 505                 510

Gly Arg Asp Ser Leu Val Asn Pro Gly Pro Ala Met Ala Thr His Lys
            515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Asn Glu Glu Glu Ile Lys Thr Thr Asn Pro Val Ala Thr Glu Glu
            565                 570                 575

Tyr Gly Thr Val Ala Thr Asn Leu Gln Ser Ala Asn Thr Ala Pro Ala
                580                 585                 590

Thr Gly Thr Val Asn Ser Gln Gly Ala Leu Pro Gly Met Val Trp Gln
            595                 600                 605

Asn Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
```

```
                     645                 650                 655
Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 21
<211> LENGTH: 736
<212> TYPE: PRT
<213> ORGANISM: Adeno-associated virus

<400> SEQUENCE: 21

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ala Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Gly Ser Thr Asn Asp Asn Thr
            260                 265                 270

Tyr Phe Gly Tyr Ser Thr Pro Trp Gly Tyr Phe Asp Phe Asn Arg Phe
        275                 280                 285
```

```
His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Thr Thr Ile Ala Asn Asn
                325                 330                 335

Leu Thr Ser Thr Val Gln Val Phe Thr Asp Ser Glu Tyr Gln Leu Pro
                340                 345                 350

Tyr Val Leu Gly Ser Ala His Gln Gly Cys Leu Pro Pro Phe Pro Ala
                355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Ser Arg
                435                 440                 445

Thr Gln Thr Thr Ser Gly Thr Ala Gly Asn Arg Glu Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Thr Asn Gln Asn
                485                 490                 495

Asn Asn Ser Asn Phe Ala Trp Thr Gly Ala Thr Lys Tyr His Leu Asn
                500                 505                 510

Gly Arg Asp Ser Leu Val Asn Pro Gly Pro Ala Met Ala Thr His Lys
    515                 520                 525

Asp Asp Glu Asp Lys Phe Phe Pro Met Ser Gly Val Leu Ile Phe Gly
530                 535                 540

Lys Gln Gly Ala Gly Asn Ser Asn Val Asp Leu Asp Asn Val Met Ile
545                 550                 555                 560

Thr Ser Glu Glu Glu Ile Lys Thr Thr Asn Pro Val Ala Thr Glu Glu
                565                 570                 575

Tyr Gly Thr Val Ala Thr Asn Leu Gln Ser Ser Asn Thr Ala Pro Ala
                580                 585                 590

Thr Gly Thr Val Asn Ser Gln Gly Ala Leu Pro Gly Met Val Trp Gln
                595                 600                 605

Glu Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
```

```
                       705                 710                 715                 720
Tyr Ser Glu Pro Arg Pro Ile Gly Thr Arg Tyr Leu Thr Arg Asn Leu
                725                 730                 735

<210> SEQ ID NO 22
<211> LENGTH: 736
<212> TYPE: PRT
<213> ORGANISM: Adeno-associated virus

<400> SEQUENCE: 22

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Gly Ser Thr Asn Asp Asn Thr
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Lys Leu Asn Phe Lys Leu Phe Asn Ile Gln
305                 310                 315                 320

Val Lys Glu Val Thr Thr Asn Asp Gly Thr Thr Ile Ala Asn Asn
                325                 330                 335

Leu Thr Ser Thr Val Gln Val Phe Thr Asp Ser Glu Tyr Gln Leu Pro
            340                 345                 350
```

```
Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Glu Leu Gln Phe Ser
450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Thr Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
530                 535                 540

Lys Gln Gly Ala Gly Asn Ser Asn Val Asp Leu Asp Asn Val Met Ile
545                 550                 555                 560

Thr Ser Glu Glu Glu Ile Lys Thr Thr Asn Pro Val Ala Thr Glu Glu
                565                 570                 575

Tyr Gly Thr Val Ala Thr Asn Leu Gln Ser Ala Asn Thr Ala Pro Ala
            580                 585                 590

Thr Gly Thr Val Asn Ser Gln Gly Ala Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Asn Lys Ser Thr Asn Val Asp Phe Ala Val Asp Thr Asn Gly Val
                705                 710                 715                 720

Tyr Ser Glu Pro Arg Pro Ile Gly Thr Arg Tyr Leu Thr Arg Asn Leu
            725                 730                 735
```

<210> SEQ ID NO 23
<211> LENGTH: 736
<212> TYPE: PRT
<213> ORGANISM: Adeno-associated virus

<400> SEQUENCE: 23

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65              70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Arg Lys Arg Leu Asn Phe Gly Gln Thr
            165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ala Gly Gly Gly
            195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Gly Ser Thr Asn Asp Asn Thr
            260                 265                 270

Tyr Phe Gly Tyr Ser Thr Pro Trp Gly Tyr Phe Asp Phe Asn Arg Phe
    275                 280                 285

His Cys His Phe Ser Pro Arg Asp Trp Gln Arg Leu Ile Asn Asn Asn
    290                 295                 300

Trp Gly Phe Arg Pro Lys Lys Leu Asn Phe Lys Leu Phe Asn Ile Gln
305                 310                 315                 320

Val Lys Glu Val Thr Thr Asn Asp Gly Thr Thr Thr Ile Ala Asn Asn
            325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
    355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
            405                 410                 415
```

-continued

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
            435                 440                 445

Thr Gln Thr Thr Ser Gly Thr Ala Gly Asn Arg Thr Leu Gln Phe Ser
450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Thr Asn Gln Asn
            485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
            515                 520                 525

Asp Asp Glu Asp Lys Phe Phe Pro Met Ser Gly Val Leu Ile Phe Gly
530                 535                 540

Lys Gln Gly Ala Gly Asn Ser Asn Val Asp Leu Asp Asn Val Met Ile
545                 550                 555                 560

Thr Asn Glu Glu Glu Ile Lys Thr Thr Asn Pro Val Ala Thr Glu Glu
            565                 570                 575

Tyr Gly Thr Val Ala Thr Asn Leu Gln Ser Ala Asn Thr Ala Pro Ala
            580                 585                 590

Thr Gly Thr Val Asn Ser Gln Gly Ala Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
            725                 730                 735

<210> SEQ ID NO 24
<211> LENGTH: 736
<212> TYPE: PRT
<213> ORGANISM: Adeno-associated virus

<400> SEQUENCE: 24

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60

-continued

```
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Gly Ile Gly
145                 150                 155                 160

Lys Lys Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ala Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Gly Ser Thr Asn Asp Asn Thr
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Lys Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Glu Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Thr Leu Gln Phe Ser
    450                 455                 460

Gln Ala Gly Pro Ser Ser Met Ala Asn Gln Ala Lys Asn Trp Leu Pro
465                 470                 475                 480
```

-continued

```
Gly Pro Cys Tyr Arg Gln Gln Arg Val Ser Lys Thr Ala Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Ser Glu Glu Glu Ile Lys Thr Thr Asn Pro Val Ala Thr Glu Gln
                565                 570                 575

Tyr Gly Thr Val Ala Thr Asn Leu Gln Ser Ser Asn Thr Ala Pro Ala
            580                 585                 590

Thr Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 25
<211> LENGTH: 736
<212> TYPE: PRT
<213> ORGANISM: Adeno-associated virus

<400> SEQUENCE: 25

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Leu Gly Leu Val Glu Glu Gly Ala Lys Thr Ala Pro Gly Lys Lys Arg
        130                 135                 140
Pro Val Glu Gln Ser Pro Gln Glu Pro Asp Ser Ser Ser Gly Ile Gly
145                 150                 155                 160
Lys Lys Gly Gln Gln Pro Ala Lys Lys Arg Leu Asn Phe Gly Gln Thr
                    165                 170                 175
Gly Asp Ser Glu Ser Val Pro Asp Pro Gln Pro Leu Gly Glu Pro Pro
                180                 185                 190
Ala Ala Pro Ser Gly Val Gly Ser Asn Thr Met Ala Ser Gly Gly Gly
            195                 200                 205
Ala Pro Met Ala Asp Asn Asn Glu Gly Ala Asp Gly Val Gly Asn Ala
210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Gly Ser Thr Asn Asp Asn Thr
                260                 265                 270
Tyr Phe Gly Tyr Ser Thr Pro Trp Gly Tyr Phe Asp Phe Asn Arg Phe
            275                 280                 285
His Cys His Phe Ser Pro Arg Asp Trp Gln Arg Leu Ile Asn Asn Asn
        290                 295                 300
Trp Gly Phe Arg Pro Lys Lys Leu Asn Phe Lys Leu Phe Asn Ile Gln
305                 310                 315                 320
Val Lys Glu Val Thr Thr Asn Asp Gly Thr Thr Thr Ile Ala Asn Asn
                325                 330                 335
Leu Thr Ser Thr Val Gln Val Phe Thr Asp Ser Glu Tyr Gln Leu Pro
            340                 345                 350
Tyr Val Leu Gly Ser Ala His Gln Gly Cys Leu Pro Pro Phe Pro Ala
        355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Glu Phe Ser Tyr Thr Phe
                405                 410                 415
Glu Asp Val Pro Phe His Ser Ser Tyr Ala His Ser Gln Ser Leu Asp
                420                 425                 430
Arg Leu Met Asn Pro Leu Ile Asp Gln Tyr Leu Tyr Tyr Leu Ser Arg
            435                 440                 445
Thr Gln Thr Thr Ser Gly Thr Ala Gly Asn Arg Thr Leu Gln Phe Ser
        450                 455                 460
Gln Ala Gly Pro Ser Ser Met Ala Asn Gln Ala Lys Asn Trp Leu Pro
465                 470                 475                 480
Gly Pro Cys Tyr Arg Gln Gln Arg Val Ser Lys Thr Ala Asn Gln Asn
                485                 490                 495
Asn Asn Ser Asn Phe Ala Trp Thr Gly Ala Thr Lys Tyr His Leu Asn
                500                 505                 510
Gly Arg Asp Ser Leu Val Asn Pro Gly Pro Ala Met Ala Thr His Lys
            515                 520                 525
Asp Asp Glu Asp Lys Phe Phe Pro Met Ser Gly Val Leu Ile Phe Gly
530                 535                 540
```

-continued

```
Lys Gln Gly Ala Gly Asn Ser Asn Val Asp Leu Asp Asn Val Met Ile
545                 550                 555                 560

Thr Ser Glu Glu Glu Ile Lys Thr Thr Asn Pro Val Ala Thr Glu Glu
                565                 570                 575

Tyr Gly Thr Val Ala Thr Asn Leu Gln Ser Ser Asn Thr Ala Pro Ala
            580                 585                 590

Thr Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 26
<211> LENGTH: 736
<212> TYPE: PRT
<213> ORGANISM: Adeno-associated virus

<400> SEQUENCE: 26

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190
```

-continued

```
Ala Ala Pro Ser Gly Val Gly Ser Asn Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Gly Ser Thr Asn Asp Asn Thr
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Lys Leu Asn Phe Lys Leu Phe Asn Ile Gln
305                 310                 315                 320

Val Lys Glu Val Thr Thr Asn Asp Gly Thr Thr Ile Ala Asn Asn
                325                 330                 335

Leu Thr Ser Thr Val Gln Val Phe Thr Asp Ser Glu Tyr Gln Leu Pro
                340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Glu Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Asn Glu Glu Glu Ile Lys Thr Thr Asn Pro Val Ala Thr Glu Gln
                565                 570                 575

Tyr Gly Thr Val Ala Thr Asn Leu Gln Ser Ala Asn Thr Ala Pro Ala
            580                 585                 590

Thr Gly Thr Val Asn Ser Gln Gly Ala Leu Pro Gly Met Val Trp Gln
        595                 600                 605
```

-continued

```
Asp Arg Asp Val Tyr Leu Gln Gly Pro Ile Trp Ala Lys Ile Pro His
    610                 615                 620
Thr Asp Gly His Phe His Pro Ser Pro Leu Met Gly Gly Phe Gly Leu
625                 630                 635                 640
Lys His Pro Pro Gln Ile Leu Ile Lys Asn Thr Pro Val Pro Ala
                645                 650                 655
Asn Pro Pro Thr Thr Phe Ser Pro Ala Lys Phe Ala Ser Phe Ile Thr
            660                 665                 670
Gln Tyr Ser Thr Gly Gln Val Ser Val Glu Ile Glu Trp Glu Leu Gln
                675                 680                 685
Lys Glu Asn Ser Lys Arg Trp Asn Pro Glu Ile Gln Tyr Thr Ser Asn
690                 695                 700
Tyr Asn Lys Ser Thr Asn Val Asp Phe Ala Val Asp Thr Asn Gly Val
705                 710                 715                 720
Tyr Ser Glu Pro Arg Pro Ile Gly Thr Arg Tyr Leu Thr Arg Asn Leu
                725                 730                 735

<210> SEQ ID NO 27
<211> LENGTH: 738
<212> TYPE: PRT
<213> ORGANISM: Adeno-associated virus

<400> SEQUENCE: 27

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Lys Pro
                20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Ala Ala Asp Ala Ala Ala Leu Glu His Asp Lys Ala Tyr Asp
65                  70                  75                  80
Gln Gln Leu Gln Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
        130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Ala Pro Ser Gly Val Gly Pro Asn Thr Met Ala Ala Gly Gly
        195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
```

```
Leu Tyr Lys Gln Ile Ser Asn Gly Thr Ser Gly Gly Ala Thr Asn Asp
                260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
        450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670
```

```
Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 28
<211> LENGTH: 736
<212> TYPE: PRT
<213> ORGANISM: Adeno-associated virus

<400> SEQUENCE: 28

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300
```

-continued

```
Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
        340                 345                 350

Pro Tyr Val Leu Gly Ser Ala His Glu Gly Cys Leu Pro Pro Phe Pro
    355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
```

<210> SEQ ID NO 29
<211> LENGTH: 736
<212> TYPE: PRT
<213> ORGANISM: Adeno-associated virus

<400> SEQUENCE: 29

```
Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
                20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Phe Gly Leu Val Glu Glu Gly Ala Lys Thr Ala Pro Gly Lys Lys Arg
130                 135                 140
Pro Val Glu Gln Ser Pro Gln Glu Pro Asp Ser Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Thr Pro Ala Ala Val Gly Pro Thr Thr Met Ala Ser Gly Gly Gly
        195                 200                 205
Ala Pro Met Ala Asp Asn Asn Glu Gly Ala Asp Gly Val Gly Asn Ala
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
            260                 265                 270
Tyr Phe Gly Tyr Ser Thr Pro Trp Gly Tyr Phe Asp Phe Asn Arg Phe
        275                 280                 285
His Cys His Phe Ser Pro Arg Asp Trp Gln Arg Leu Ile Asn Asn Asn
    290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
        355                 360                 365
```

-continued

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
                580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 30
<211> LENGTH: 736
<212> TYPE: PRT
<213> ORGANISM: Adeno-associated virus

<400> SEQUENCE: 30

Met Ala Ala Asp Gly Tyr Leu Pro Asp Trp Leu Glu Asp Asn Leu Ser
1               5                   10                  15

```
Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430
```

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 31
<211> LENGTH: 735
<212> TYPE: PRT
<213> ORGANISM: Adeno-associated virus

<400> SEQUENCE: 31

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

```
Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Pro Val Lys Thr Ala Pro Gly Lys Lys Arg
130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
                180                 185                 190

Ala Ala Pro Ser Gly Leu Gly Thr Asn Thr Met Ala Thr Gly Ser Gly
                195                 200                 205

Ala Pro Met Ala Asp Asn Asn Glu Gly Ala Asp Gly Val Gly Asn Ser
                210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
                450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495
```

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 32
<211> LENGTH: 736
<212> TYPE: PRT
<213> ORGANISM: Adeno-associated virus

<400> SEQUENCE: 32

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
    130                 135                 140

```
Ala Val Asp Gln Ser Pro Gln Glu Pro Asp Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Ala Pro Thr Ser Leu Gly Ser Asn Thr Met Ala Ser Gly Gly Gly
                195                 200                 205

Ala Pro Met Ala Asp Asn Asn Glu Gly Ala Asp Gly Val Gly Asn Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
            450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
            515                 520                 525

Asp Asp Glu Glu Lys Phe Phe Pro Met His Gly Asn Leu Ile Phe Gly
            530                 535                 540

Lys Glu Gly Thr Thr Ala Ser Asn Ala Glu Leu Asp Asn Val Met Ile
545                 550                 555                 560
```

-continued

```
Thr Asp Glu Glu Ile Arg Thr Thr Asn Pro Val Ala Thr Glu Gln
            565                 570                 575

Tyr Gly Thr Val Ala Asn Asn Leu Gln Ser Ser Asn Thr Ala Pro Thr
            580                 585                 590

Thr Gly Thr Val Asn His Gln Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
            645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
            725                 730                 735

<210> SEQ ID NO 33
<211> LENGTH: 736
<212> TYPE: PRT
<213> ORGANISM: Adeno-associated virus

<400> SEQUENCE: 33

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205
```

```
Ala Pro Met Ala Asp Asn Asn Glu Gly Ala Asp Gly Val Gly Asn Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
                    260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
    290                 295                 300
Gly Phe Arg Pro Lys Lys Leu Ser Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Asn Arg Thr
    435                 440                 445
Gln Gly Thr Thr Ser Gly Thr Thr Asn Gln Ser Arg Leu Leu Phe Ser
450                 455                 460
Gln Ala Gly Pro Gln Ser Met Ser Leu Gln Ala Arg Asn Trp Leu Pro
465                 470                 475                 480
Gly Pro Cys Tyr Arg Gln Gln Arg Leu Ser Lys Thr Ala Asn Asp Asn
                485                 490                 495
Asn Asn Ser Asn Phe Pro Trp Thr Ala Ala Ser Lys Tyr His Leu Asn
            500                 505                 510
Gly Arg Asp Ser Leu Val Asn Pro Gly Pro Ala Met Ala Ser His Lys
    515                 520                 525
Asp Asp Glu Glu Lys Phe Phe Pro Met His Gly Asn Leu Ile Phe Gly
530                 535                 540
Lys Glu Gly Thr Thr Ala Ser Asn Ala Glu Leu Asp Asn Val Met Ile
545                 550                 555                 560
Thr Asp Glu Glu Glu Ile Arg Thr Thr Asn Pro Val Ala Thr Glu Gln
                565                 570                 575
Tyr Gly Thr Val Ala Asn Asn Leu Gln Ser Ser Asn Thr Ala Pro Thr
            580                 585                 590
Thr Arg Thr Val Asn Asp Gln Gly Ala Leu Pro Gly Met Val Trp Gln
    595                 600                 605
Asp Arg Asp Val Tyr Leu Gln Gly Pro Ile Trp Ala Lys Ile Pro His
610                 615                 620
```

```
Thr Asp Gly His Phe His Pro Ser Pro Leu Met Gly Gly Phe Gly Leu
625                 630                 635                 640

Lys His Pro Pro Gln Ile Met Ile Lys Asn Thr Pro Val Pro Ala
        645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
        690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
            725                 730                 735
```

<210> SEQ ID NO 34
<211> LENGTH: 737
<212> TYPE: PRT
<213> ORGANISM: Adeno-associated virus

<400> SEQUENCE: 34

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Gly Ala Lys Thr Ala Pro Ala Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
            165                 170                 175

Thr Gly Asp Ser Glu Ser Val Pro Asp Pro Gln Pro Leu Gly Glu Pro
        180                 185                 190

Pro Ala Ala Pro Ser Ser Val Gly Ser Gly Thr Val Ala Ala Gly Gly
    195                 200                 205

Gly Ala Pro Met Ala Asp Asn Asn Glu Gly Ala Asp Gly Val Gly Asn
210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Ser Glu Thr Ala Gly Ser Thr Asn Asp Asn
        260                 265                 270
```

```
Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
            435                 440                 445

Arg Thr Gln Ser Asn Pro Gly Gly Thr Ala Gly Asn Arg Glu Leu Gln
            450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
            515                 520                 525

His Lys Asp Asp Glu Asp Arg Phe Phe Pro Ser Ser Gly Val Leu Ile
            530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
            595                 600                 605

Gln Asn Arg Asp Val Tyr Leu Gln Gly Pro Ile Trp Ala Lys Ile Pro
            610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
            675                 680                 685
```

```
Gln Lys Glu Asn Ser Lys Arg Trp Asn Pro Glu Ile Gln Tyr Thr Ser
        690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 35
<211> LENGTH: 2211
<212> TYPE: DNA
<213> ORGANISM: Adeno-associated virus

<400> SEQUENCE: 35
atggctgccg atggttatct tccagattgg ctcgaggaca acctctctga gggcattcgc      60
gagtggtggg acttgaaacc tggagccccg aacccaaag ccaaccagca aaagcaggac     120
gacggccggg gtctggtgct tcctggctac aagtacctcg acccttcaa cggactcgac     180 aaggggagc ccgtcaacgc ggcggacgca gcggccctcg agcacgacaa ggcctacgac     240
cagcagctca aagcgggtga caatccgtac ctgcggtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gcaatcaccc caggaaccag actcctcttc gggcatcggc     480
aagaaaggcc agcagcccgc gaaaaagaga ctcaactttg gcagacagg cgactcagag     540 tcagtgcccg accctcaacc actcggagaa cccccgcag cccctctgg tgtgggatct     600 aatacaatgg ctgcaggcgg tggcgctcca atggcagaca taacgaagg cgccgacgga     660 gtgggtaacg cctcaggaaa ttggcattgc gattccacat ggctgggcga cagagtcatc     720
accaccagca cccgaacctg gccctcccc acctacaaca accacctcta caagcaaatc     780
tccagccaat cgggagcaag caccaacgac aacacctact cggctacag caccccctgg     840 gggtattttg actttaacag attccactgc cacttctcac cacgtgactg gcagcgactc     900
atcaacaaca actggggatt ccggcccaag agactcaact tcaagctctt caacatccag     960
gtcaaggagg tcacgacgaa tgatggcacc acgaccatcg ccaataacct taccagcacg    1020
gttcaggtct ttacggactc ggaataccag ctcccgtacg tcctcggctc tgcgcaccag    1080
ggctgcctgc ctccgttccc ggcggacgtc ttcatgattc ctcagtacgg gtacctgact    1140
ctgaacaatg gcagtcaggc cgtgggccgt tcctccttct actgcctgga gtactttcct    1200
tctcaaatgc tgagaacggg caacaacttt gagttcagct acacgtttga ggacgtgcct    1260
tttcacagca gctacgcgca gccaaaagc tggaccggc tgatgaaccc cctcatcgac    1320
cagtacctgt actacctgtc tcggactcag accacgagtg gtaccgcagg aaatcggacg    1380
ttgcaatttt ctcaggccgg gcctagtagc atggcgaatc aggccaaaaa ctggctaccc    1440 gggcccctgct accggcagca acgcgtctcc aagacagcga atcaaaataa caacagcaac    1500
tttgcctgga ccggtgccac caagtatcat ctgaatggca gagactctct ggtaaatccc    1560
ggtcccgcta tggcaaccca aaggacgac gaagacaaat ttttccgat gagcggagtc    1620 ttaatatttg gaaacaggg agctggaaat agcaacgtgg accttgacaa cgttatgata    1680
accagtgagg aagaaattaa aaccaccaac ccagtggcca cagaacagta cggcacggtg    1740
gccactaacc tgcaatcgtc aaacaccgct cctgctacag ggaccgtcaa cagtcaagga    1800
```

-continued

```
gccttacctg gcatggtctg gcagaaccgg gacgtgtacc tgcagggtcc tatctgggcc    1860
aagattcctc acacggacgg acactttcat ccctcgccgc tgatgggagg ctttggactg    1920
aaacacccgc tcctcagat cctgattaag aatacacctg ttcccgcgaa tcctccaact     1980
accttcagtc cagctaagtt tgcgtcgttc atcacgcagt acagcaccgg acaggtcagc    2040
gtggaaattg aatgggagct gcagaaagaa aacagcaaac gctggaaccc agagattcaa    2100
tacacttcca actacaacaa atctacaaat gtggactttg ctgttgacac aaatggcgtt    2160
tattctgagc ctcgccccat cggcacccgt tacctcaccc gtaatctgta a             2211
```

<210> SEQ ID NO 36
<211> LENGTH: 738
<212> TYPE: PRT
<213> ORGANISM: Adeno-associated virus

<400> SEQUENCE: 36

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300
```

```
Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
            325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
```

-continued

```
                725                 730                 735
Asn Leu

<210> SEQ ID NO 37
<211> LENGTH: 21
<212> TYPE: PRT
<213> ORGANISM: Adeno-associated virus

<400> SEQUENCE: 37

Glu Ile Lys Ala Thr Asn Pro Val Ala Thr Glu Arg Phe Gly Thr Val
1               5                   10                  15

Ala Val Asn Phe Gln
            20

<210> SEQ ID NO 38
<211> LENGTH: 21
<212> TYPE: PRT
<213> ORGANISM: Adeno-associated virus

<400> SEQUENCE: 38

Glu Ile Lys Ala Thr Asn Pro Val Ala Thr Glu Arg Phe Gly Thr Val
1               5                   10                  15

Ala Val Asn Leu Gln
            20

<210> SEQ ID NO 39
<211> LENGTH: 21
<212> TYPE: PRT
<213> ORGANISM: Adeno-associated virus

<400> SEQUENCE: 39

Glu Ile Arg Thr Thr Asn Pro Val Ala Thr Glu Gln Tyr Gly Ser Val
1               5                   10                  15

Ser Thr Asn Leu Gln
            20

<210> SEQ ID NO 40
<211> LENGTH: 21
<212> TYPE: PRT
<213> ORGANISM: Adeno-associated virus

<400> SEQUENCE: 40

Glu Ile Arg Thr Thr Asn Pro Val Ala Thr Glu Gln Tyr Gly Thr Val
1               5                   10                  15

Ala Asn Asn Leu Gln
            20

<210> SEQ ID NO 41
<211> LENGTH: 21
<212> TYPE: PRT
<213> ORGANISM: Adeno-associated virus

<400> SEQUENCE: 41

Glu Ile Arg Thr Thr Asn Pro Val Ala Thr Glu Gln Tyr Gly Thr Val
1               5                   10                  15

Ala Thr Asn Leu Gln
            20

<210> SEQ ID NO 42
<211> LENGTH: 21
<212> TYPE: PRT
<213> ORGANISM: Adeno-associated virus
```

-continued

```
<400> SEQUENCE: 42

Glu Ile Lys Thr Thr Asn Pro Val Ala Thr Glu Gln Tyr Gly Thr Val
1               5                   10                  15

Ala Thr Asn Leu Gln
            20

<210> SEQ ID NO 43
<211> LENGTH: 21
<212> TYPE: PRT
<213> ORGANISM: Adeno-associated virus
<220> FEATURE:
<221> NAME/KEY: VARIANT
<222> LOCATION: (12)..(12)
<223> OTHER INFORMATION: /replace="Glu"
<220> FEATURE:
<221> NAME/KEY: misc_feature
<222> LOCATION: (1)..(21)
<223> OTHER INFORMATION: /note="Variant residues given in the sequence
      have no preference with respect to those in the annotations
      for variant positions"

<400> SEQUENCE: 43

Glu Ile Lys Thr Thr Asn Pro Val Ala Thr Glu Gln Tyr Gly Thr Val
1               5                   10                  15

Ala Thr Asn Leu Gln
            20

<210> SEQ ID NO 44
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 44

His His His His His His
1               5
```